United States Patent
Dominguez et al.

(10) Patent No.: US 9,260,422 B2
(45) Date of Patent: Feb. 16, 2016

(54) CERTAIN KYNURENINE-3-MONOOXYGENASE INHIBITORS, PHARMACEUTICAL COMPOSITIONS, AND METHODS OF USE THEREOF

(75) Inventors: Celia Dominguez, Los Angeles, CA (US); Leticia M. Toledo-Sherman, Santa Monica, CA (US); Stephen Martin Courtney, Oxfordshire (GB); Michael Prime, Oxfordshire (GB); William Mitchell, Lincolnshire (GB); Christopher John Brown, Abingdon (GB); Paula C. De Aguiar Pena, Oxfordshire (GB); Peter Johnson, Oxfordshire (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 14/235,253

(22) PCT Filed: Jul. 26, 2012

(86) PCT No.: PCT/US2012/048254
§ 371 (c)(1),
(2), (4) Date: Jun. 27, 2014

(87) PCT Pub. No.: WO2013/016488
PCT Pub. Date: Jan. 31, 2013

(65) Prior Publication Data
US 2014/0329816 A1    Nov. 6, 2014

Related U.S. Application Data

(60) Provisional application No. 61/512,782, filed on Jul. 28, 2011.

(51) Int. Cl.
| | | |
|---|---|---|
| *A61K 31/506* | (2006.01) | |
| *C07D 417/04* | (2006.01) | |
| *C07D 239/42* | (2006.01) | |
| *C07D 401/04* | (2006.01) | |
| *C07D 403/04* | (2006.01) | |
| *C07D 239/26* | (2006.01) | |
| *C07D 413/04* | (2006.01) | |
| *C07D 239/28* | (2006.01) | |
| *C07D 413/14* | (2006.01) | |
| C07D 491/044 | (2006.01) | |
| C07D 491/048 | (2006.01) | |
| C07D 491/052 | (2006.01) | |

(52) U.S. Cl.
CPC ............ *C07D 417/04* (2013.01); *C07D 239/26* (2013.01); *C07D 239/28* (2013.01); *C07D 239/42* (2013.01); *C07D 401/04* (2013.01); *C07D 403/04* (2013.01); *C07D 413/04* (2013.01); *C07D 413/14* (2013.01); *C07D 491/044* (2013.01); *C07D 491/048* (2013.01); *C07D 491/052* (2013.01)

(58) Field of Classification Search
CPC .. C07D 417/04; C07D 239/26; C07D 239/28; C07D 239/42; C07D 401/04; C07D 403/04; C07D 413/04; C07D 413/14; C07D 491/044; C07D 491/048; C07D 491/052; A61K 31/519; A61K 31/506
See application file for complete search history.

(56) References Cited

U.S. PATENT DOCUMENTS

| | | | | |
|---|---|---|---|---|
| 3,908,012 | A * | 9/1975 | De Angelis et al. | 514/256 |
| 3,950,525 | A * | 4/1976 | De Angelis et al. | 514/269 |
| 8,536,186 | B2 * | 9/2013 | Wityak et al. | 514/256 |
| 8,883,785 | B2 * | 11/2014 | Dominguez et al. | 514/235.8 |
| 2006/0293339 | A1 * | 12/2006 | Chakravarty et al. | 514/255.05 |
| 2011/0183957 | A1 * | 7/2011 | Wityak et al. | 514/210.2 |
| 2011/0230428 | A1 * | 9/2011 | Wityak et al. | 514/23 |
| 2012/0041009 | A1 * | 2/2012 | Mizuno | 514/274 |
| 2013/0029988 | A1 * | 1/2013 | Dominguez et al. | 514/236.2 |
| 2014/0329795 | A1 * | 11/2014 | Courtney et al. | 514/210.18 |
| 2014/0329816 | A1 * | 11/2014 | Dominguez et al. | 514/236.2 |

OTHER PUBLICATIONS

C. Dominguez et al., 32 Journal of Organic Chemistry, 1591-1596 (1967).*
J.J. Lafferty et al., 32 Journal of Organic Chemistry, 1591-1596 (1967) ("Lafferty").*

* cited by examiner

*Primary Examiner* — Alexander R Pagano

(57) ABSTRACT

Certain chemical entities are provided herein. Also provided are pharmaceutical compositions comprising at least one chemical entity and one or more pharmaceutically acceptable vehicle. Methods of treating patients suffering from certain diseases and disorders responsive to the inhibition of KMO activity are described, which comprise administering to such patients an amount of at least one chemical entity effective to reduce signs or symptoms of the disease or disorder are disclosed. These diseases include neurodegenerative disorders such as Huntington's disease. Also described are methods of treatment include administering at least one chemical entity as a single active agent or administering at least one chemical entity in combination with one or more other therapeutic agents. Also provided are methods for screening compounds capable of inhibiting KMO activity.

10 Claims, No Drawings

CERTAIN KYNURENINE-3-MONOOXYGENASE INHIBITORS, PHARMACEUTICAL COMPOSITIONS, AND METHODS OF USE THEREOF

This application claims the benefit under 35 U.S.C. §371 of PCT International Application No. PCT/US2012/048254, filed Jul. 26, 2012, which in turn claims the benefit of U.S. Provisional Appln. No. 61/512,782, filed Jul. 28, 2011, which is incorporated herein by reference for all purposes.

Provided herein are certain kynurenine-3-monooxygenase inhibitors, pharmaceutical compositions thereof, and methods of their use.

Kynurenine-3-monooxygenase (KMO) is an enzyme in the tryptophan degradation pathway that catalyzes the conversion of kynurenine (KYN) into 3-hydroxykynurenine (3-HK), which is further degraded to the excitotoxic NMDA receptor agonist QUIN (3-hydroxyanthranilate oxygenase). 3-OH-KYN and QUIN act synergistically, i.e. 3-OH-KYN significantly potentiates the excitotoxic actions of QUIN. Studies from several laboratories have provided evidence that the shift of KYN pathway metabolism away from the 3-OH-KYN/QUIN branch to increase the formation of the neuroprotectant KYNA in the brain leads to neuroprotection. In addition the effects of KMO inhibition in the elevation of AA (Anthranilic acid) could have significant biological effects.

It has also been reported that KMO expression increases in inflammatory conditions or after immune stimulation. 3-OH-KYN, the product of its activity, accumulates in the brain of vitamin B-6 deficient neonatal rats and it causes cytotoxicity when added to neuronal cells in primary cultures or when locally injected into the brain. Recently, it was reported that relatively low concentrations (nanomolar) of 3-OH-KYN may cause apoptotic cell death of neurons in primary neuronal cultures. Structure-activity studies have in fact shown that 3-OH-KYN, and other o-amino phenols, may be subject to oxidative reactions initiated by their conversion to quinoneimines, a process associated with concomitant production of oxygen-derived free radicals. The involvement of these reactive species in the pathogenesis of ischemic neuronal death has been widely studied in the last several years and it has been shown that oxygen derived free radicals and glutamate mediated neurotransmission co-operate in the development of ischemic neuronal death.

It was also recently demonstrated that KMO activity is particularly elevated in the iris-ciliary body and that neo-formed 3-OH-KYN is secreted into the fluid of the lens. An excessive accumulation of 3-OH-KYN in the lens may cause cataracts.

QUIN is an agonist of a subgroup of NMDA receptors and when directly injected into brain areas it destroys most neuronal cell bodies sparing fibers en passant and neuronal terminals. QUIN is a relatively poor agonist of the NMDA receptor complex containing either NR2C or NR2D subunits, while it interacts with relatively high affinity with the NMDA receptor complex containing NR2A and NR2B subunits. The neurotoxicity profile found after intrastriatal injection of QUIN resembles that found in the basal nuclei of Huntington's disease patients: while most of the intrinsic striatal neurons are destroyed, NADH-diaphorase-staining neurons (which are now considered able to express nitric oxide synthetase) and neurons containing neuropeptide Y seem to be spared together with axon terminals and fiber en passant.

In vivo, infusion of KYNA has shown to modulate synaptic release of critical neurotransmitters implicated in cognitive processes and affective mental faculties, such as Acetylcholine, dopamine, and glutamate; therefore elevation of KYNA in brain can have effects in cognitive disorders and disorders arising from, or influenced by, changes in the levels of the neurotransmitters glutamate, dopamine, or Ach (such as Alzheimers, MCI, PD, schizophrenia, HD, OCD, and Tourette's).

In vitro, the neurotoxic effects of the compound have been studied in different model systems with variable results: chronic exposure of organotypic cortico-striatal cultures to submicromolar concentration of QUIN causes histological signs of pathology, similar results have been obtained after chronic exposure of cultured neuronal cells.

In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. In retrovirus-infected macaques, it has been proposed that most of the increased content of brain QUIN (approximately 98%) is due to local production. In fact, a robust increase in the activities of IDO, KMO and kynureninase has been found in areas of brain inflammation.

Previous studies have shown that agents able to increase brain KYNA content cause sedation, mild analgesia, increase in the convulsive threshold and neuroprotection against excitotoxic or ischemic damage. In addition to the above reported evidences, it has been recently demonstrated that a number of compounds able to increase brain KYNA formation may cause a robust decrease in glutamate (GLU) mediated neurotransmission by reducing GLU concentrations in brain extracellular spaces.

There remains a need for compounds that are effective inhibitors of KMO and may be used in treating neurodegenerative disorders.

Provided is at least one chemical entity chosen from compounds of Formula I

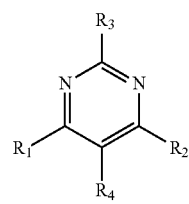

Formula I and pharmaceutically acceptable salts and prodrugs thereof wherein:

$R_1$ is chosen from optionally substituted aryl and optionally substituted heteroaryl;

$R_2$ is chosen from cyano, optionally substituted heteroaryl and optionally substituted heterocycloalkyl;

$R_3$ is chosen from hydrogen and optionally substituted lower alkyl and $R_4$ is chosen from hydrogen, halo, optionally substituted lower alkyl, hydroxyl, optionally substituted lower alkoxy, and optionally substituted amino, or $R_1$ and $R_4$, taken together with intervening atoms form a bicyclic ring of the formula

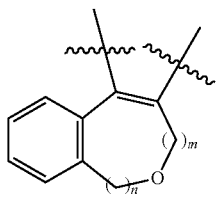

which is optionally substituted where m is 0 or 1 and n is 0 or 1, provided that at least one of m and n is 1,
provided that
1) when $R_2$ is 4-methyloxazol-2-yl, $R_3$ is methyl, and $R_4$ is hydrogen, then $R_1$ is not 3,4-dichlorophenyl; and
2) when $R_3$ and $R_4$ are hydrogen, then $R_1$ is not 5-chloropyridin-3-yl, 3,5-dichlorophenyl, or

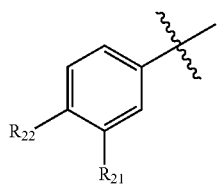

where $R_{21}$ is halo and $R_{22}$ is hydrogen, halo, trifluoromethoxy, methyl, or isopropoxy.

Also provided is a pharmaceutical composition comprising at least one chemical entity described herein and at least one pharmaceutically acceptable excipient.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Also provided is a packaged pharmaceutical composition comprising at least one pharmaceutical composition described herein and instructions for using the composition to treat a subject suffering from a condition or disorder mediated by Kynurenine 3-mono-oxygenase activity.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or In some embodiments, from 1 to 3, heteroatoms chosen from N, O, and S, with the remaining ring atoms being carbon; and bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For example, heteroaryl also includes a 5- or 6-membered heterocycloalkyl, aromatic ring fused to a 5- to 7-membered aryl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolyl, isoxazolinyl, oxazolyl, oxazolinyl, oxadiazolyl, thiazolinyl, thiadiazolinyl, tetrazolyl, thienyl, benzothiophenyl, furanyl, benzofuranyl, benzoimidazolinyl, benzooxazolyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycloalkyl" also refers to 5- and 6-membered carbocyclic aromatic rings fused to a 5- to 7-membered heterocycloalkyl ring containing 1 or more heteroatoms chosen from N, O, and S, provided that the point of attachment is at the heterocycloalkyl ring. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1-C_2$ alkyl)$O$— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted cycloalkyl, optionally substituted aryl, optionally substituted heterocycloalkyl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, cycloalkyl, aryl, heterocycloalkyl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)$OC_1$-$C_4$ alkyl, —CON($C_1$-$C_4$ alkyl)($C_1$-$C_4$ alkyl), CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted alkoxy" refers to alkoxy wherein the alkyl constituent is substituted (i.e., —O-(substituted alkyl)) wherein "substituted alkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C═O) (optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula CH$_3$(C═O)—.

By "alkoxycarbonyl" is meant an ester group of the formula (alkoxy)(C═O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —NH$_2$.

The term "sulfinyl" includes the groups: —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)—H, —S(O$_2$)-(optionally substituted ($C_1$-$C_6$)alkyl), —S(O$_2$)-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocyclyloxy); and —S(O$_2$)-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxycarbonyl" refers to the group (substituted alkyl)-O—C(O)— wherein the group is attached to the parent structure through the carbonyl functionality and wherein substituted alkyl is as described herein.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derivatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

Chemical entities include, but are not limited to compounds described herein and all pharmaceutically acceptable forms thereof. Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs. Hence, the terms "chemical entity" and "chemical entities" also encompass pharmaceutically acceptable salts, prodrugs, and mixtures thereof.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities described herein. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include NH$_2$, primary, and secondary amines such as NHR$^x$, and NR$^x$R$^y$, wherein R$^x$ is hydrogen, ($C_1$-$C_{18}$)-alkyl, ($C_3$-$C_7$)-cycloalkyl, ($C_3$-$C_7$)-cycloalkyl-($C_1$-$C_4$)-alkyl-, ($C_6$-$C_{14}$)-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-neurodegenerative therapeutic.

The term "therapeutically effective amount" of a chemical entity described herein means an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, a therapeutically effective amount is an amount sufficient to treat the symptoms of neurodegenerative pathway or disease. In some embodiments a therapeutically effective amount is an amount sufficient to reduce the signs or side effects of a neurodegenerative disease. In some embodiments, a therapeutically effective amount of a chemical entity is an amount sufficient to prevent a significant increase or significantly reduce the level of neuronal cell death. In some embodiments, a therapeutically effective amount of a chemical entity is an amount sufficient to prevent a significant increase or significantly reduce the level of QUIN associated with neuronal cell death. In some embodiments, a therapeutically effective amount of a chemical entity is an amount sufficient to effect an increase in the level of KYNA associated with neuronal cell health. In some embodiments, a therapeutically effective amount of a chemical entity is an amount sufficient to increase the anticonvulsant and neuroprotective properties associated with lowered levels of QUIN and increased levels of KYNA. In some embodiments, a therapeutically effective amount is an amount sufficient to modulate an inflammatory process in the body, including but not limited to inflammation in the brain, spinal cord, and peripheral nervous system, or meninges. In some embodiments, a therapeutically effective amount is an amount sufficient to modulate the production of cytokines responsible for mounting an effective immune response (such as IL-1 beta or TNF-alpha) or an amount sufficient to affect monocyte/macrophage pro-inflammatory activity in the periphery or in the brain in conditions where the blood-brain barrier is compromised, such as in multiple sclerosis).

In methods described herein for treating a neurodegenerative disorder, a therapeutically effective amount may also be an amount sufficient, when administered to a patient, to detectably slow the progression of the neurodegenerative disease, or prevent the patient to whom the chemical entity is given from presenting symptoms of the neurodegenerative disease. In some methods described herein for treating a neurodegenative disease, a therapeutically effective amount may also be an amount sufficient to produce a detectable decrease in the level of neuronal cell death. For example, in some embodiments a therapeutically effective amount is an amount of a chemical entity described herein sufficient to significantly decrease the level of neuronal death by effecting a detectable decrease in the amount of QUIN, and an increase in the amount of kynurenine, KYNA, or anthranilic acid.

In addition, an amount is considered to be a therapeutically effective amount if it is characterized as such by at least one of the above criteria or experimental conditions, regardless of any inconsistent or contradictory results under a different set of criteria or experimental conditions.

The term "inhibition" indicates a significant decrease in the baseline activity of a biological activity or process "Inhibition of KMO activity" refers to a decrease in KMO activity as a direct or indirect response to the presence of at least one chemical entity described herein, relative to the activity of KMO in the absence of at least one chemical entity. The decrease in activity may be due to the direct interaction of the compound with KMO, or due to the interaction of the chemical entity(ies) described herein with one or more other factors that in turn affect KMO activity. For example, the presence of the chemical entity(ies) may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one chemical entity described herein, relative to the activity of KMO in the absence of the at least one chemical entity. The decrease in activity may be due to the direct interaction of the compound with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the chemical entity described herein has an $IC_{50}$ value less than or equal to 1 micromolar. In some embodiments, the chemical entity has an $IC_{50}$ value less than or equal to less than 100 micromolar. In some embodiments, the chemical entity has an $IC_{50}$ value less than or equal to 10 nanomolar.

"KMO activity" also includes activation, redistribution, reorganization, or capping of one or more various KMO membrane-associated proteins (such as those receptors found in the mitochondria), or binding sites can undergo redistribution and capping that can initiate signal transduction. KMO activity also can modulate the availability of kynurenine, which can effect the synthesis or production of QUIN, KYNA, anthranilic acid, and/or 3-HK.

A "disease responsive to inhibition of KMO activity" is a disease in which inhibiting KMO provides a therapeutic benefit such as an amelioration of symptoms, decrease in disease progression, prevention or delay of disease onset, prevention or amelioration of an inflammatory response, or inhibition of aberrant activity and/or death of certain cell-types (such as neuronal cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is least one chemical entity chosen from compounds of Formula I

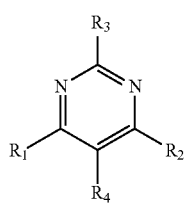

Formula I and pharmaceutically acceptable salts and prodrugs thereof wherein:

$R_1$ is chosen from optionally substituted aryl and optionally substituted heteroaryl;

$R_2$ is chosen from cyano, optionally substituted heteroaryl and optionally substituted heterocycloalkyl;

$R_3$ is chosen from hydrogen and optionally substituted lower alkyl and $R_4$ is chosen from hydrogen, halo, optionally substituted lower alkyl, hydroxyl, optionally substituted lower alkoxy, and optionally substituted amino, or $R_1$ and $R_4$, taken together with intervening atoms form a bicyclic ring of the formula

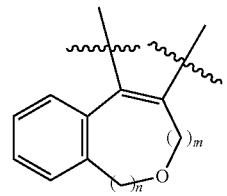

which is optionally substituted where m is 0 or 1 and n is 0 or 1, provided that at least one of m and n is 1,
provided that
1) when $R_2$ is 4-methyloxazol-2-yl, $R_3$ is methyl, and $R_4$ is hydrogen, then $R_1$ is not 3,4-dichlorophenyl; and
2) when $R_3$ and $R_4$ are hydrogen, then $R_1$ is not 5-chloropyridin-3-yl, 3,5-dichlorophenyl, or

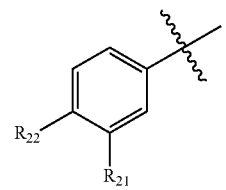

where $R_{21}$ is halo and $R_{22}$ is hydrogen, halo, trifluoromethoxy, methyl, or isopropoxy.

In some embodiments, $R_1$ is phenyl optionally substituted with one, two, or three groups chosen from heteroaryl, heterocycloalkyl, cycloalkyl, optionally substituted amino, halo, optionally substituted lower alkyl, optionally substituted lower alkoxy, optionally substituted cycloalkoxy, and hydroxy.

In some embodiments, $R_1$ is phenyl optionally substituted with one, two, or three groups chosen from heteroaryl, heterocycloalkyl, cycloalkyl, cycloalkoxy optionally substituted with lower alkoxy, lower alkoxy, or lower alkyl substituted with halo, optionally substituted amino, halo, lower alkyl optionally substituted with amino, alkylamino, dialkylamino, or heterocycloalkyl, trifluoromethyl, trifluoromethoxy, lower alkoxy, and hydroxy.

In some embodiments, $R_1$ is phenyl optionally substituted with one, two, or three groups chosen from furan-2-yl, 1H-pyrrol-2-yl, 1H-imidazol-2-yl, pyrrolidin-3-yl, pyrrolidin-1-yl, oxetan-3-yl optionally substituted with lower alkyl, halo, lower alkyl, cyclopropyl optionally substituted with lower alkyl, lower alkoxy, or lower alkyl substituted with halo, optionally substituted amino, lower alkyl optionally substituted with amino, alkylamino, dialkylamino, or heterocycloalkyl, trifluoromethoxy, cyclopropoxy optionally substituted with lower alkyl, lower alkoxy, or lower alkyl substituted with halo, and trifluoromethyl.

In some embodiments, $R_1$ is chosen from 3-chloro-4-cyclopropoxyphenyl, 4-tert-butyl-3-chlorophenyl, 3-chloro-4-(furan-2-yl)phenyl, 3-chloro-4-(1H-pyrrol-2-yl)phenyl, 3-chloro-4-(1H-imidazol-2-yl)phenyl, 3-chloro-4-(pyrrolidin-3-yl)phenyl, 3-chloro-4-(pyrrolidin-1-yl)phenyl, 3-chloro-4-(3-methyloxetan-3-yl)phenyl, 3-chloro-4-[1-(trifluoromethyl)cyclopropyl]phenyl, 3-chloro-4-cyclopropylphenyl, 3-chloro-4-(1-methylcyclopropyl)phenyl, 3-chloro-4-(1-methoxycyclopropyl)phenyl, 3-chloro-4-[cyclopropyl(methyl)amino]phenyl, 3-chloro-4-(cyclopropylamino)phenyl, 3-chloro-4-[(dimethylamino)methyl]phenyl, 4-(aziridin-1-ylmethyl)-3-chlorophenyl, 3-chloro-4-trifluoromethoxyphenyl, 3-chloro-4-methylphenyl, 3-fluoro-4-methylphenyl, 3-chloro-4-fluorophenyl, 3-chloro-4-isopropoxyphenyl, 3,4-difluorophenyl, 2-trifluoromethylphenyl, 3,4-dichlorophenyl, 3-chlorophenyl, 4-chlorophenyl, and 3,5-dichlorophenyl.

In some embodiments, $R_1$ is pyridin-3-yl optionally substituted with one, two, or three groups chosen from halo, lower alkyl, lower alkoxy, optionally substituted amino, optionally substituted heterocycloalkyl, optionally substituted heteroaryl, and hydroxy.

In some embodiments, $R_1$ is pyridin-3-yl optionally substituted with one, two, or three groups chosen from halo, optionally substituted lower alkyl, optionally substituted lower alkoxy, and hydroxy.

In some embodiments, $R_1$ is pyridin-3-yl optionally substituted with one, two, or three groups chosen from halo, lower alkyl, trifluoromethyl, lower alkoxy, and hydroxy.

In some embodiments, $R_1$ is pyridin-3-yl optionally substituted with one, two, or three groups chosen from halo, lower alkyl, cycloalkyl, and trifluoromethyl.

In some embodiments, $R_1$ is chosen from 1H-benzo[d]imidazol-5-yl, 2H-1,3-benzodioxol-5-yl, 1H-1,3-benzodiazol-5-yl, 2H-1,3-benzoxadiazol-5-yl, 1-benzofuran-5-yl, 1,3-benzoxazol-5-yl, 1,3-benzoxazol-6-yl, 1,3-benzothiazol-5-yl, imidazo[1,2-a]pyridin-6-yl, 1H-indazol-5-yl, 1H-indol-5-yl, pyrazolo[1,5-a]pyridin-5-yl, quinazolin-6-yl, quinazolin-7-yl, quinolin-6-yl, quinoxalin-6-yl, 2,3,3a,7a-tetrahydro-1-benzofuran-5-yl, 5-oxo-4,5-dihydro-1,2,4-oxadiazol-3-yl, 2-oxo-2,3 dihydrobenzo[d]oxazol-5-yl, and 2,3-dihydro-1,4-benzodioxin-6-yl, each of which is optionally substituted with one, two, or three groups chosen from halo, lower alkyl, lower alkoxy, and cycloalkyl.

In some embodiments, $R_1$ is chosen from 7-chloro-1H-benzo[d]imidazol-5-yl, 8-chloroquinoxalin-6-yl, 5-chloroquinazolin-7-yl, 8-chloroquinazolin-6-yl, 8-chloroquinolin-6-yl, quinolin-6-yl, 7-chloro-1-methyl-1H-indazol-5-yl, 1-cyclopropyl-1H-indazol-5-yl, 7-chloro-1H-indol-5-yl, 1-cyclopropyl-1H-indol-5-yl, 7-chloro-2,3,3a,7a-tetrahydro-1-benzofuran-5-yl, 7-chloro-2,1,3-benzoxadiazol-5-yl, 2,2-difluoro-2H-1,3-benzodioxol-5-yl, 2H-1,3-benzodioxol-5-yl, pyrazolo[1,5-a]pyridin-5-yl, 4-chloro-1,3-benzoxazol-6-yl, 7-chloro-2-cyclopropyl-1,3-benzoxazol-5-yl, 8-chloroimidazo[1,2-a]pyridin-6-yl, 5-oxo-4,5-dihydro-1,2,4-oxadiazol-3-yl, 7-chloro-3-methyl-2-oxo-2,3-dihydrobenzo[d]oxazol-5-yl, 7-chloro-2-oxo-2,3-dihydrobenzo[d]oxazol-5-yl, 7-chloro-2-methyl-1,3-benzoxazol-5-yl, 2,3-dihydro-1,4-benzodioxin-6-yl, 7-chloro-1H-1,3-benzodiazol-5-yl, 7-chloro-1,3-benzothiazol-5-yl, 7-chloro-1,3-benzoxazol-5-yl, and 7-chloro-1-benzofuran-5-yl.

In some embodiments, $R_2$ is chosen from pyrrolidin-1-yl, pyrrolidin-4-yl, thiazol-2-yl, 1H-pyrazol-3-yl, [1,2,4]oxadiazol-5-yl, [1,2,4]oxadiazol-3-yl, 4H-[1,2,4]oxadiazol-5-one-3-yl, 4H-[1,2,4]oxadiazole-5-thione-3-yl, [1,2,4]triazol-1-yl, 1H-benzoimidazol-2-yl, 1H-tetrazol-5-yl, 2H-tetrazol-5-yl, tetrazol-1-yl, 2,4-dihydro-[1,2,4]-triazol-3-one-5-yl, 4H-[1,2,4]-triazol-3-yl, 1H-imidazol-2-yl, 1H-imidazol-4-yl, oxazol-2-yl, pyridin-2-yl, benzooxazol-2-yl, imidazol-1-yl, piperazin-4-yl, piperazin-2-one-4-yl, pyrazol-1-yl, 1,6-dihydropyrimidin-5-yl, 2,3-dihydro-1H-pyrazol-4-yl, 2,3-dihydro-1H-imidazol-1-yl, 4,5-dihydro-1H-imidazol-2-yl, 2,5-dihydro-1H-pyrazol-1-yl, 1H-imidazol-1-yl, each of which is optionally substituted.

In some embodiments, $R_2$ is chosen from pyrrolidin-1-yl, pyrrolidin-4-yl thiazol-2-yl, 1H-pyrazol-3-yl, [1,2,4]oxadiazol-5-yl, [1,2,4]oxadiazol-3-yl, 4H-[1,2,4]oxadiazol-5-one-3-yl, 4H-[1,2,4]oxadiazole-5-thione-3-yl, [1,2,4]triazol-1-yl, 1H-benzoimidazol-2-yl, 1H-tetrazol-5-yl, 2H-tetrazol-5-yl, tetrazol-1-yl, 2,4-dihydro-[1,2,4]-triazol-3-one-5-yl, 4H-[1,2,4]-triazol-3-yl, 1H-imidazol-2-yl, 1H-imidazol-4-yl, oxazol-2-yl, pyridin-2-yl, benzooxazol-2-yl, imidazol-1-yl, piperazin-4-yl, piperazin-2-one-4-yl, pyrazol-1-yl, 1,6-dihydropyrimidin-5-yl, 2,3-dihydro-1H-pyrazol-4-yl, 2,3-dihydro-1H-imidazol-1-yl, 4,5-dihydro-1H-imidazol-2-yl, 2,5-dihydro-1H-pyrazol-1-yl, and 1H-imidazol-1-yl, each of which is optionally substituted with one or two groups chosen from carboxyl, aminocarbonyl, optionally substituted amino, oxo, lower alkyl, trifluoromethyl, halo, and heterocycloalkyl.

In some embodiments, $R_2$ is chosen from pyrrolidin-1-yl optionally substituted with carboxyl, pyrrolidin-4-yl optionally substituted with carboxyl, thiazol-2-yl, 1H-pyrazol-3-yl, 3-methyl-[1,2,4]oxadiazol-5-yl, [1,2,4]oxadiazol-3-yl, [1,2,4]oxadiazol-5-yl, [1,2,4]triazol-1-yl, 1H-benzoimidazol-2-yl, 1H-tetrazol-5-yl, 1-methyl-1H-tetrazol-5-yl, 2,4-dihydro-[1,2,4]-triazol-3-one-5-yl, 2-methyl-2H-tetrazol-5-yl, 3-trifluoromethyl-pyrazol-1-yl, 4H-[1,2,4]oxadiazol-5-one-3-yl, 4H-[1,2,4]oxadiazole-5-thione-3-yl, 4H-[1,2,4]-triazol-3-yl, 4-methyl-1H-imidazol-2-yl, 4-trifluoromethyl-1H-imidazol-2-yl, oxazol-2-yl, 4-methyl-oxazol-2-yl, 5-fluoropyridin-2-yl, 5-methyl-[1,2,4]oxadiazol-3-yl, tetrazol-1-yl, benzooxazol-2-yl, imidazol-1-yl, piperazin-4-yl optionally substituted with carboxyl, piperazin-2-one-4-yl, pyrazol-1-yl, 2-oxo-2,3-dihydro-1H-imidazol-4-yl, 6-oxo-1,6-dihydropyrimidin-5-yl, 1-methyl-3-oxo-2,3-dihydro-1H-pyrazol-4-yl, 2-methyl-3-oxo-2,3-dihydro-1H-pyrazol-4-yl, 1,2-dimethyl-3-oxo-2,3-dihydro-1H-pyrazol-4-yl, 2-amino-6-oxo-1,6-dihydropyrimidin-5-yl, 2-oxo-2,3-dihydro-1H-imidazol-1-yl, 3-methyl-2-oxo-2,3-dihydro-1H-imidazol-1-yl, 5-(methylcarbamoyl)pyridin-2-yl, 5-(trifluoromethyl)-1,2,4-oxadiazol-3-yl, 5-methyl-4H-1,2,4-triazol-3-yl, 4,5-dihydro-1H-imidazol-2-yl, 3-methyl-5-oxo-2,5-dihydro-1H-pyrazol-1-yl, 1H-imidazol-2-yl, and 4-(trifluoromethyl)-1H-imidazol-1-yl.

In some embodiments, $R_3$ is hydrogen.

In some embodiments, $R_4$ is chosen from hydrogen, methyl, fluoro, methoxy, methoxymethyl, hydroxyl, and amino. In some embodiments, $R_4$ is hydrogen. In some embodiments, $R_4$ is methyl. In some embodiments, $R_4$ is fluoro. In some embodiments, $R_4$ is methoxymethyl. In some embodiments, $R_4$ is methoxy. In some embodiments, $R_4$ is hydroxyl. In some embodiments, $R_4$ is amino.

In some embodiments, $R_1$ and $R_4$, taken together with intervening atoms form a bicyclic ring of the formula

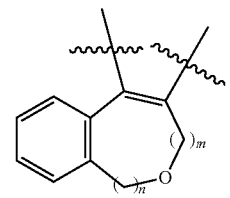

where m is 0 and n is 1 and wherein the ring is optionally substituted with one or two groups independently chosen from hydrogen, halo, optionally substituted lower alkyl, optionally substituted lower alkoxy, and optionally substituted lower cycloalkoxy.

In some embodiments, $R_1$ and $R_4$, taken together with intervening atoms form a bicyclic ring of the formula

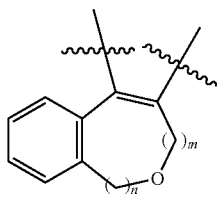

where m is 1 and n is 0 and wherein the ring is optionally substituted with one or two groups independently chosen from hydrogen, halo, optionally substituted lower alkyl, optionally substituted lower alkoxy, and optionally substituted lower cycloalkoxy.

Also provided is at least one chemical entity chosen from

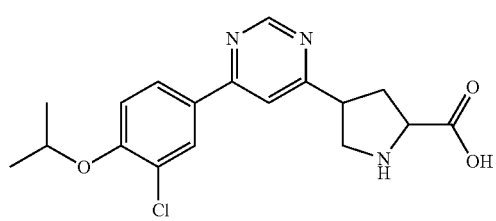

4-(6-(3-chloro-4-isopropoxyphenyl)pyrimidin-4-yl)pyrrolidine-2-carboxylic acid

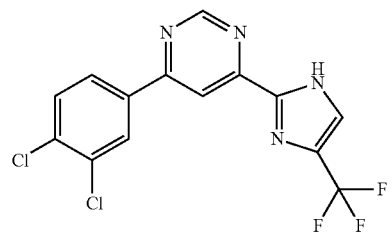

4-(3,4-dichlorophenyl)-6-(4-trifluoromethyl)-1H-imidazol-2-yl)pyrimidine

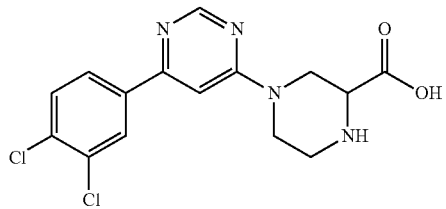

4-(6-(3,4-dichlorophenyl)pyrimidin-4-yl)piperazine-2-carboxylic acid

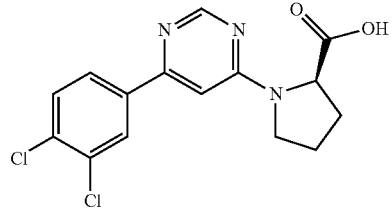

(R)-1-(6-(3,4-dichlorophenyl)pyrimidin-4-yl)pyrrolidine-2-carboxylic acid

-continued

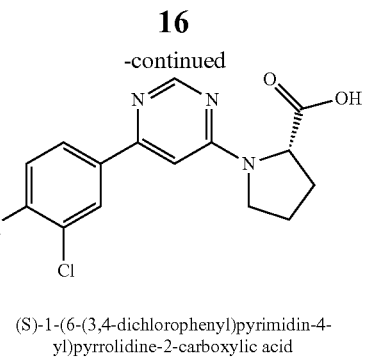

(S)-1-(6-(3,4-dichlorophenyl)pyrimidin-4-yl)pyrrolidine-2-carboxylic acid

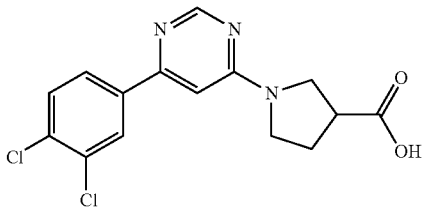

1-(6-(3,4-dichlorophenyl)pyrimidin-4-yl)pyrrolidine-3-carboxylic acid

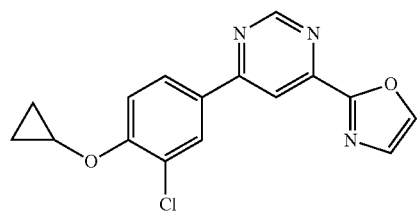

2-(6-(3-chloro-4-cyclopropoxyphenyl)pyrimidin-4-yl)oxazole

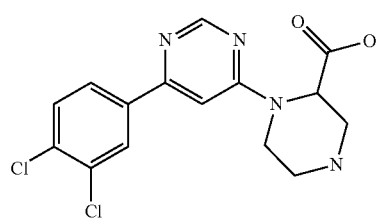

1-(6-(3,4-dichlorophenyl)pyrimidin-4-yl)piperazine-2-carboxylic acid

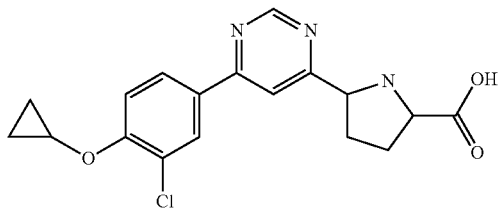

5-(6-(3-chloro-4-cyclopropoxyphenyl)pyrimidin-4-yl)pyrrolidine-2-carboxylic acid

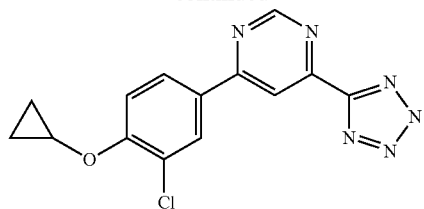

4-(3-chloro-4-cyclopropoxyphenyl)-6-(1H-1,2,3,4-tetrazol-5-yl)pyrimidine

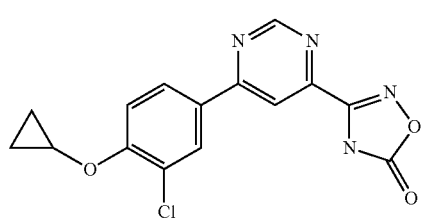

3-[6-(3-chloro-4-cyclopropoxyphenyl)pyrimidin-4-yl]-4,5-dihydro-1,2,4-oxadiazol-5-one

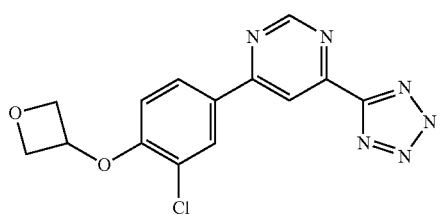

4-[3-chloro-4-(oxetan-3-yloxy)phenyl]-6-(2H-1,2,3,4-tetrazol-5-yl)pyrimidine

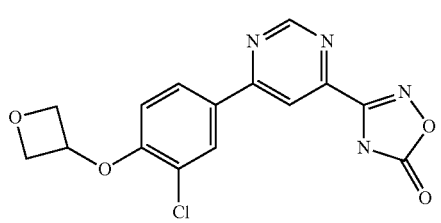

3-{6-[3-chloro-4-(oxetan-3-yloxy)phenyl]pyrimidin-4-yl}-4,5-dihydro-1,2,4-oxadiazol-5-one

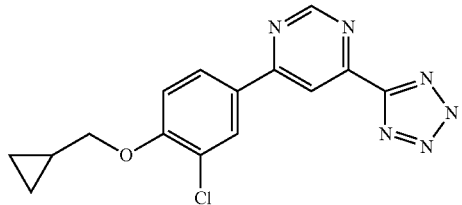

4-[3-chloro-4-(cyclopropylmethoxy)phenyl]-6-(2H-1,2,3,4-tetrazol-5-yl)pyrimidine

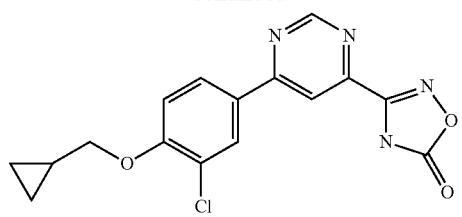

3-{6-[3-chloro-4-(cyclopropylmethoxy)phenyl]pyrimidin-4-yl}-4,5-dihydro-1,2,4-oxadiazol-5-one

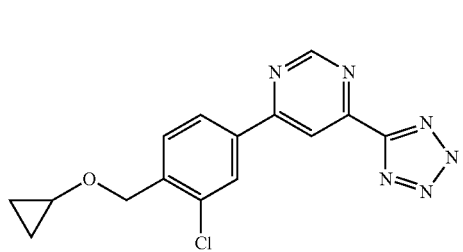

4-[3-chloro-4-(cyclopropoxymethyl)phenyl]-6-(2H-1,2,3,4-tetrazol-5-yl)pyrimidine

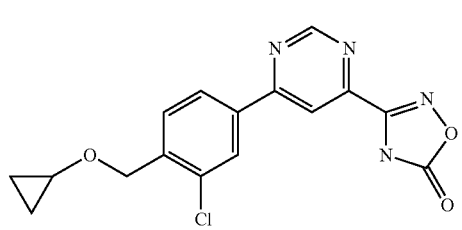

3-{6-[3-chloro-4-(cyclopropoxymethyl)phenyl]pyrimidin-4-yl}-4,5-dihydro-1,2,4-oxadiazol-5-one

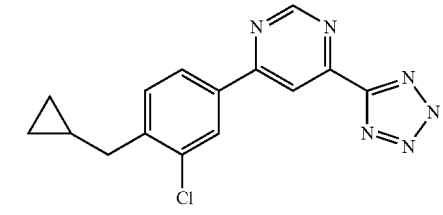

4-[3-chloro-4-(cyclopropylmethyl)phenyl]-6-(2H-1,2,3,4-tetrazol-5-yl)pyrimidine

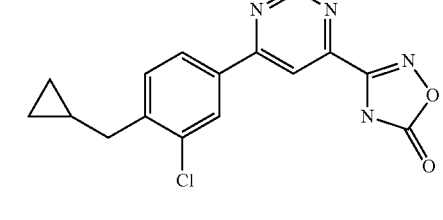

3-{6-[3-chloro-4-(cyclopropylmethyl)phenyl]pyrimidin-4-yl}-4,5-dihydro-1,2,4-oxadiazol-5-one -continued

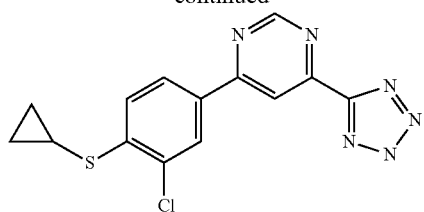

4-[3-chloro-4-(cyclopropylsulfanyl)phenyl]-6-
(2H-1,2,3,4-tetrazol-5-yl)pyrimidine

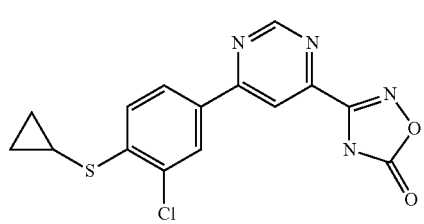

3-{6-[3-chloro-4-
(cyclopropylsulfanyl)phenyl]pyrimidin-4-yl}-
4,5-dihydro-1,2,4-oxadiazol-5-one

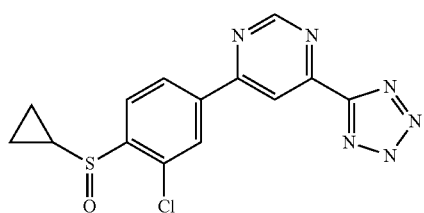

4-[3-chloro-4-(cyclopropanesulfinyl)phenyl]-6-
(2H-1,2,3,4-tetrazol-5-yl)pyrimidine

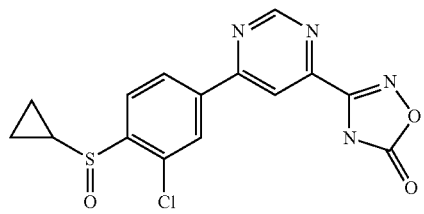

3-{6-[3-chloro-4-
(cyclopropanesulfinyl)phenyl]pyrimidin-4-yl}-
4,5-dihydro-1,2,4-oxadiazol-5-one

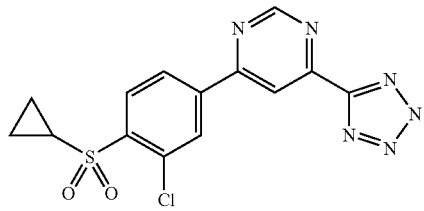

4-[3-chloro-4-(cyclopropanesulfonyl)phenyl]-6-
(2H-1,2,3,4-tetrazol-5-yl)pyrimidine -continued

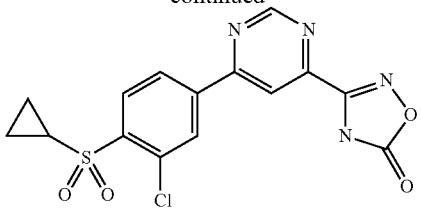

3-{6-[3-chloro-4-
(cyclopropanesulfonyl)phenyl]pyrimidin-4-yl}-
4,5-dihydro-1,2,4-oxadiazol-5-one

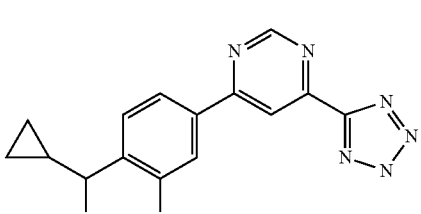

{2-chloro-4-[6-(2H-1,2,3,4-tetrazol-5-
yl)pyrimidin-4-
yl]phenyl}(cyclopropyl)methanol

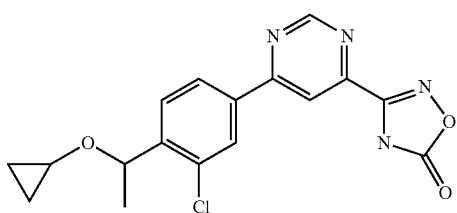

3-{6-[3-chloro-4-(1-
(cyclopropoxyethyl)phenyl]pyrimidin-4-yl}-4,5-
dihydro-1,2,4-oxadiazol-5-one

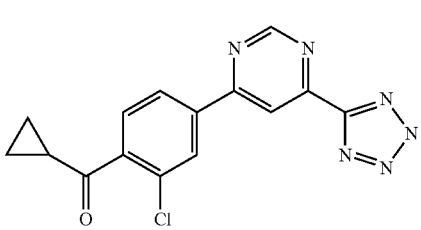

4-(3-chloro-4-cyclopropanecarbonylphenyl)-6-
(2H-1,2,3,4-tetrazol-5-yl)pyrimidine

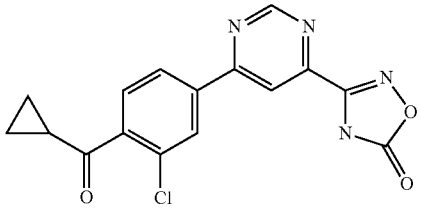

3-[6-[3-chloro-4-
cyclopropanecarbonylphenyl)pyrimidin-4-yl]-
4,5-dihydro-1,2,4-oxadiazol-5-one

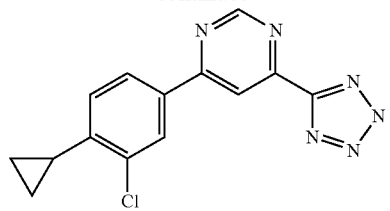

4-(3-chloro-4-cyclopropyphenyl)-6-(2H-1,2,3,4-tetrazol-5-yl)pyrimidine

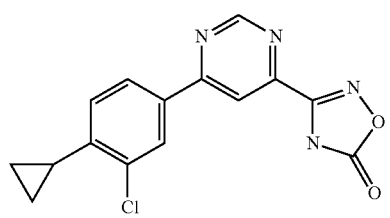

3-[6-[3-chloro-4-cyclopropylphenyl)pyrimidin-4-yl]-4,5-dihydro-1,2,4-oxadiazol-5-one

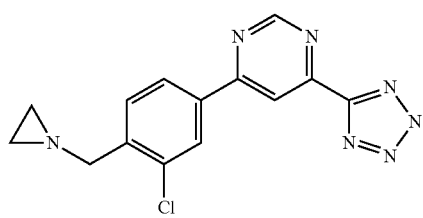

4-[4-(aziridin-1-ylmethyl)-3-chlorophenyl]-6-(2H-1,2,3,4-tetrazol-5-yl)pyrimidine

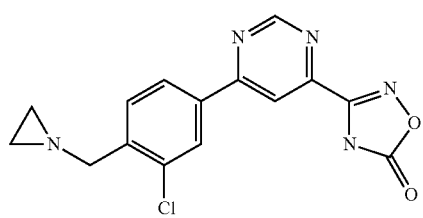

3-{6-[4-(aziridin-1-ylmethyl)-3-chlorophenyl]pyrimidine-4-yl]-4,5-dihydro-1,2,4-oxadiazol-5-one

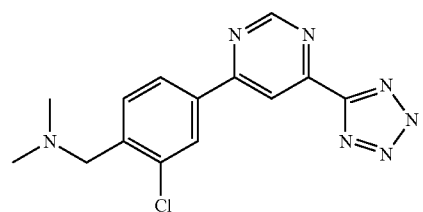

({2-chloro-4-[6-(2H-1,2,3,4-tetrazol-5-yl)pyrimidin-4-yl]phenyl}methyl)dimethylamine

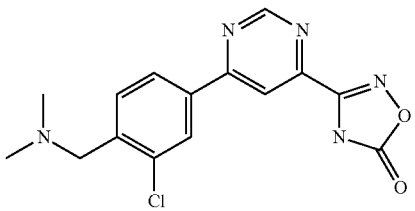

3-(6-{3-chloro-4-[(dimethylamino)methyl]phenyl}pyrimidin-4-yl)-4,5-dihydro-1,2,4-oxadiazol-5-one

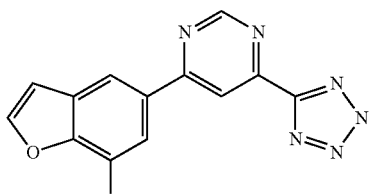

4-(7-chloro-1-benzofuran-5-yl)-6-(2H-1,2,3,4-tetrazol-5-yl)pyrimidine

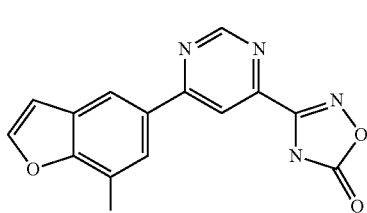

3-[6-(7-chloro-1-benzofuran-5-yl)pyrimidin-4-yl]-4,5-dihydro-1,2,4-oxadiazol-5-one

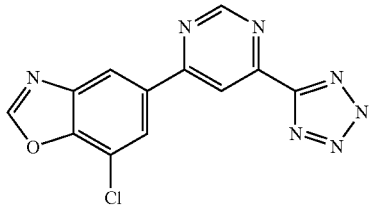

7-chloro-5-[6-(2H-1,2,3,4-tetrazol-5-yl)pyrimidin-4-yl]-1,3-benzoxazole

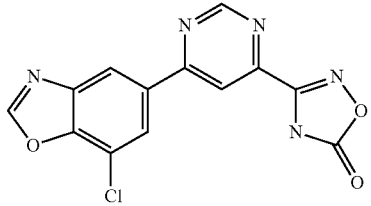

3-[6-(7-chloro-1,3-benzoxazol-5-yl)pyrimidin-4-yl]-4,5-dihydro-1,2,4-oxadiazol-5-one -continued

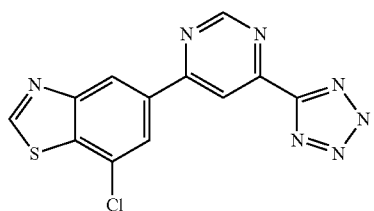

7-chloro-5-[6-(2H-1,2,3,4-tetrazol-5-yl)pyrimidin-4-yl]-1,3-benzothiazole

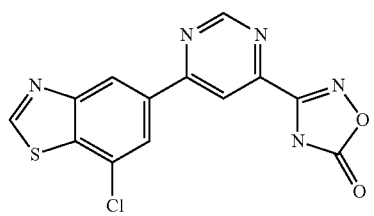

3-[6-(7-chloro-1,3-benzothiazol-5-yl)pyrimidin-4-yl]-4,5-dihydro-1,2,4-oxadiazol-5-one

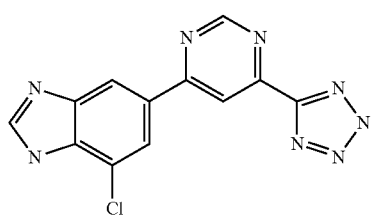

7-chloro-5-[6-(2H-1,2,3,4-tetrazol-5-yl)pyrimidin-4-yl]-1H-1,3-benzodiazole

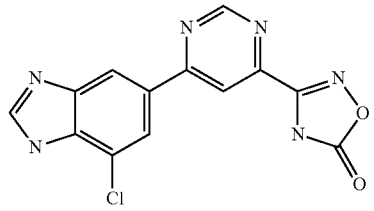

3-[6-(7-chloro-1H-1,3-benzodiazol-5-yl)pyrimidin-4-yl]-4,5-dihydro-1,2,4-oxadiazol-5-one

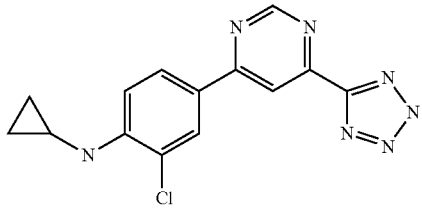

2-chloro-N-cyclopropyl-4-[6-(2H-1,2,3,4-tetrazol-5-yl)pyrimidin-4-yl]aniline

-continued

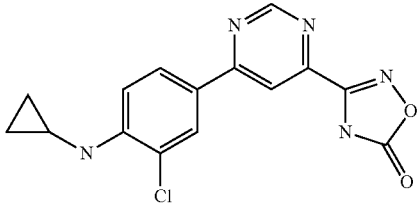

3-{6-[3-chloro-4-(cyclopropylamino)phenyl]pyrimidin-4-yl}-4,5-dihydro-1,2,4-oxadiazol-5-one

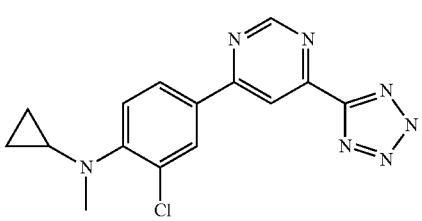

2-chloro-N-cyclopropyl-N-methyl-4-[6-(2H-1,2,3,4-tetrazol-5-yl)pyrimidin-4-yl]aniline

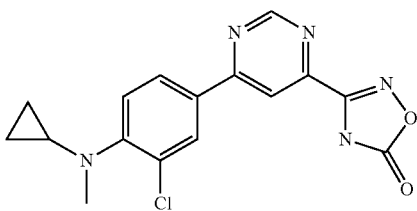

3-(6-{3-chloro-4-[cyclopropyl(methyl)amino]phenyl}pyrimidin-4-yl)-4,5-dihydro-1,2,4-oxadiazol-5-one

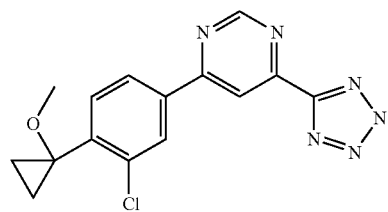

4-[3-chloro-4-(1-methoxycyclopropyl)phenyl]-6-(2H-1,2,3,4-tetrazol-5-yl)pyrimidine

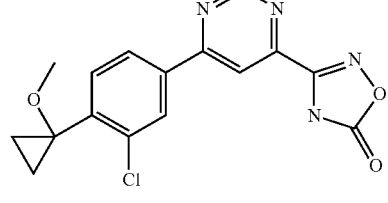

3-{6-[3-chloro-4-(1-methoxycyclopropyl)phenyl]pyrimidin-4-yl}-4,5-dihydro-1,2,4-oxadiazol-5-one -continued

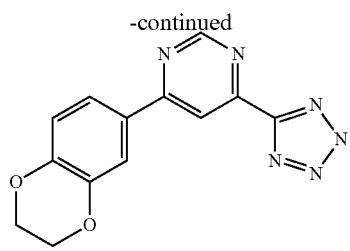

4-(2,3-dihydro-1,4-benzodioxin-6yl)-6-(2H-1,2,3,4-tetrazol-5-yl)pyrimidine

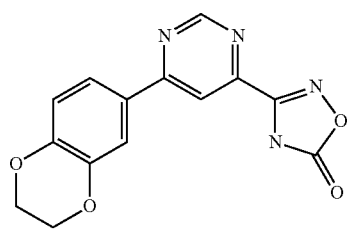

3-[6-(2,3-dihydro-1,4-benzodioxin-6-yl)pyrimidin-4-yl]-4,5-dihydro-1,2,4-oxadiazol-5-one

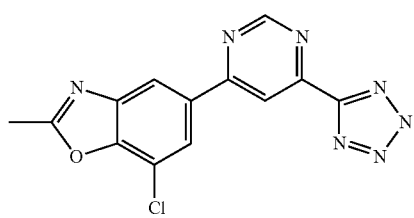

7-chloro-2-methyl-5-[6-(2H-1,2,3,4-tetrazol-5-yl)pyrimidin-4-yl]-1,3-benzoxazole

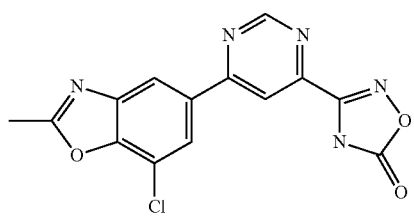

3-[6-(7-chloro-2-methyl-1,3-benzoxazol-5-yl)pyrimidin-4-yl]-4,5-dihydro-1,2,4-oxadiazol-5-one

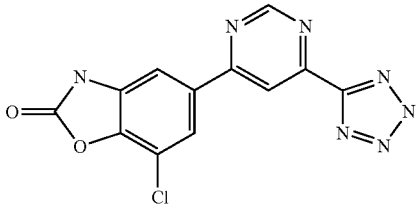

7-chloro-5-[6-(2H-1,2,3,4-tetrazol-5-yl)pyrimidin-4-yl]-2,3-dihydro-1,3-benzoxazol-2-one -continued

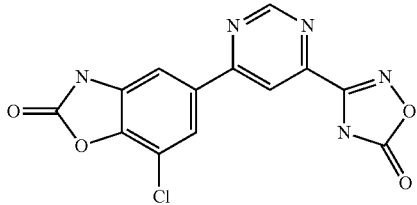

7-chloro-5-[6-(5-oxo-4,5-dihydro-1,2,4-oxadiazol-3-yl)pyrimidin-4-yl]-2,3-dihydro-1,3-benzoxazol-2-one

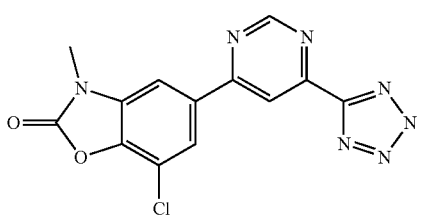

7-chloro-3-methyl-5-[6-(2H-1,2,3,4-tetrazol-5-yl)pyrimidin-4-yl]-2,3-dihydro-1,3-benzoxazol-2-one

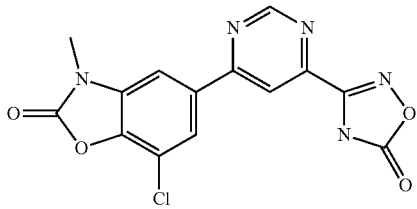

7-chloro-3-methyl-5-[6-(oxo-4,5-dihydro-1,2,4-oxadiazol-3-yl)pyrimidin-4-yl]-2,3-dihydro-1,3-benzoxazol-2-one

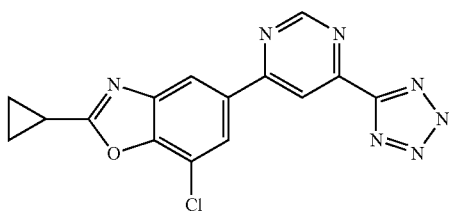

7-chloro-2-cyclopropyl-5-[6-(2H-1,2,3,4-tetrazol-5-yl)pyrimidin-4-yl]-1,3-benzoxazole

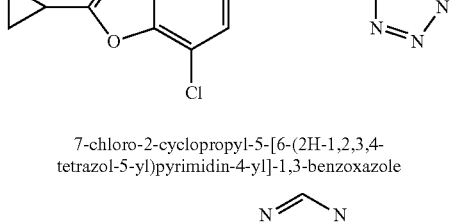

3-[6-(7-chloro-2-cyclopropyl-1,3-benzoxazol-5-yl)pyrimidin-4-yl]-4,5-dihydro-1,2,4-oxadiazol-5-one

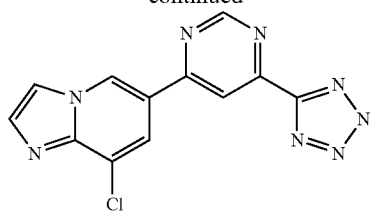

4-{8-chloroimidazo[1,2-a]pyridin-6-yl}-6-(2H-1,2,3,4-tetrazol-5-yl)pyramide

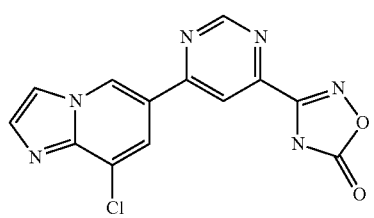

3-(6-{8-chloroimidazo[1,2-a]pyridin-6-yl}pyrimidin-4-yl)-4,5-dihydro-1,2,4-oxadiazol-5-one

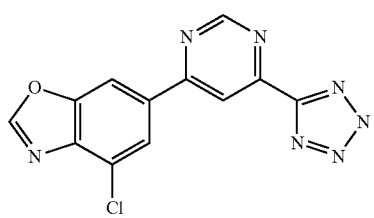

4-chloro-6-[6-(2H-1,2,3,4-tetrazol-5-yl)pyrimidin-4-yl]-1,3-benzoxazole

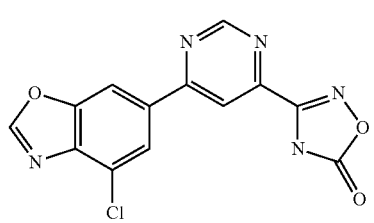

3-[6-(4-chloro-1,3-benzoxazol-6-yl)pyrimidin-4-yl]-4,5-dihydro-1,2,4-oxadiazol-5-one

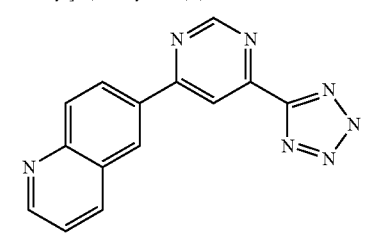

6-[6-(2H-1,2,3,4-tetrazol-5-yl)pyrimidin-4-yl]quinoline

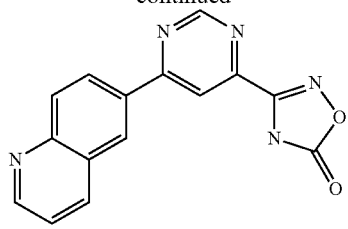

3-[6-(quinolin-6-yl)pyrimidin-4-yl]-4,5-dihydro-1,2,4-oxadiazol-5-one

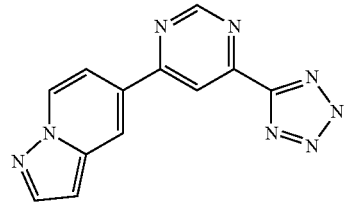

4-{pyrazolo[1,5-a]pyridin-5-yl}-6-(2H-1,2.3,4-tetrazol-5-yl)pyrimidine

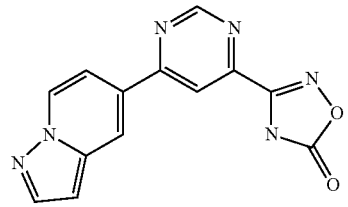

3-(6-{pyrazolo[1,5-a]pyridin-5-yl}pyrimidin-4-yl)-4,5-dihydro-1,2,4-oxadiazol-5-one

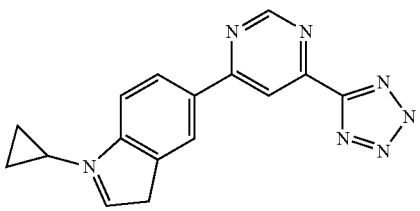

1-cyclopropyl-5-[6-(2H-1,2.3,4-tetrazol-5-yl)pyrimidin-4-yl]-1H-indole

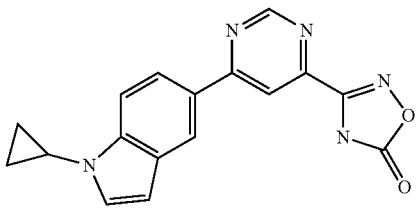

3-[6-(1-cycloporpyl-1H-indol-5-yl)-pyrimidin-4-yl]-4,5-dihydro-1,2,4-oxadiazol-5-one

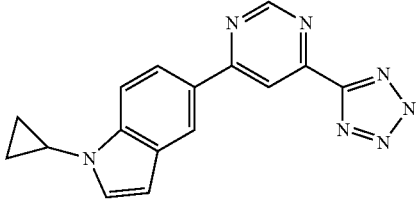

1-cyclopropyl-5-[6-(2H-1,2,3,4-tetrazol-5-yl)pyrimidin-4-yl]-1H-indazole

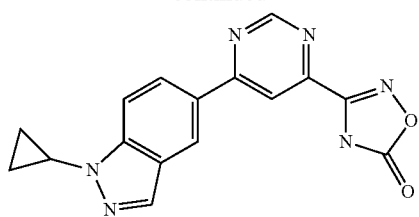

3-[6-(1-cyclopropyl-1H-indazol-5-yl)pyrimidin-4-yl]-4,5-dihydro-1,2,4-oxadiazol-5-one

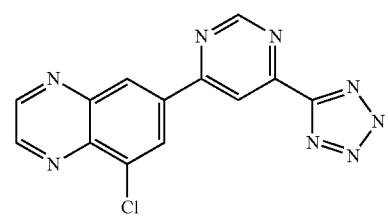

5-chloro-7-[6-2H-1,2,3,4-tetrazol-5-yl)pyrimidin-4-yl]quinoxaline

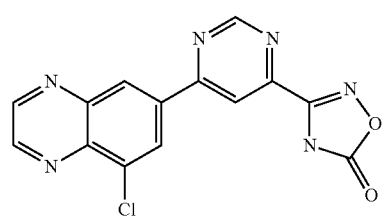

3-[6-(8-chloroquinoxalin-6-yl)pyrimidin-4-yl]-4,5-dihydro-1,2,4-oxadiazol-5-one

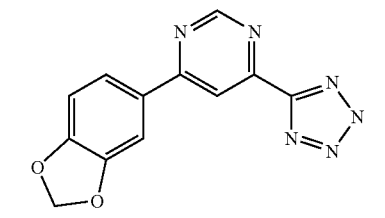

4-(2H-1,3-benzodioxol-5-yl)-6-(2H-1,2,3,4-tetrazol-5-yl)pyrimidine

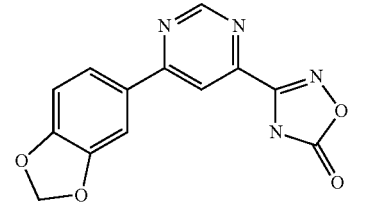

3-[6-(2H-1,3-benzodioxol-5-yl)pyrimidin-4-yl]-4,5-dihydro-1,2,4-oxadiazol-5-one

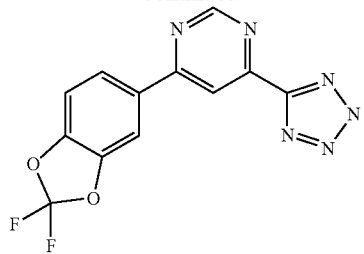

4-(2,2-difluoro-2H-1,3-benzodioxol-5-yl)-6-(2H-1,2,3,4-tetrazol-5-yl)pyrimidine

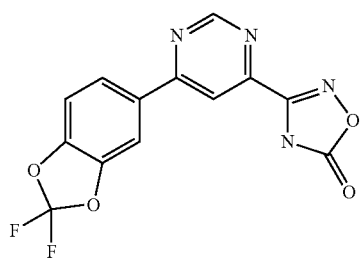

3-[6-(2,2-difluoro-2H-1,3-benzodioxol-5-yl)pyrimidin-4-yl]-4,5-dihydro-1,2,4-oxadiazol-5-one

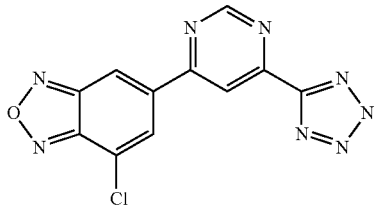

4-chloro-6-[6-(2H-1,2,3,4-tetrazol-5-yl)pyrimidin-4-yl]-2,1,3-benzoxadiazole

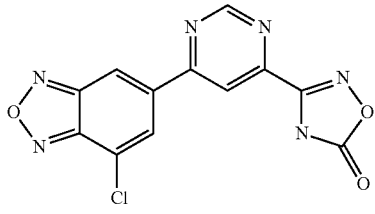

3-[6-(7-chloro-2,1,3-benzoxadiazol-5-yl)pyrimidin-4-yl]-4,5-dihydro-1,2,4-oxadiazol-5-one

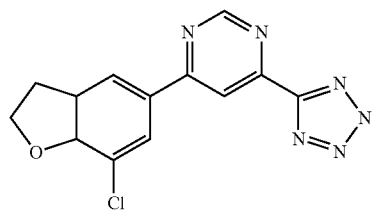

4-(7-chloro-2,3,3a,7a-tetrahydo-1-benzofuran-5-yl)-6-(2H-1,2,3,4-tetrazol-5-yl)pyrimidine

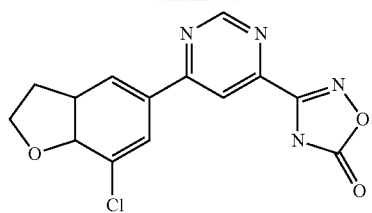

3-(6-(7-chloro-2,3,3a,7a-tetrahydo-1-
benzofuran-5-yl)pyrimidin-4-yl]-4,5-dihydro-
1,2,4-oxadiazol-5-one

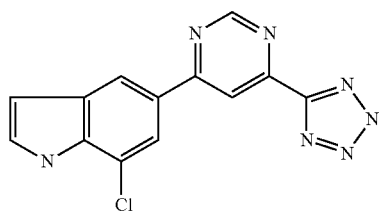

7-chloro-5-[6-(2H-1,2,3,4-tetrazol-5-
yl)pyrimidin-4-yl]-1H-indole

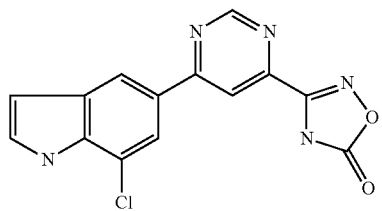

3-[6-(7-chloro-1H-indol-5-yl)pyrimidin-4-yl]-
4,5-dihydro-1,2,4-oxadiazol-5-one

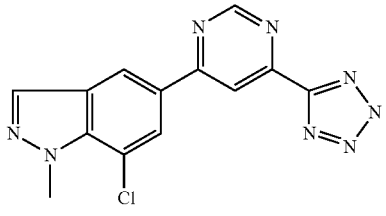

7-chloro-1-methyl-5-[6-(2H-1,2,3,4-tetrazol-5-
yl)pyrimidin-4-yl]-1H-indazole

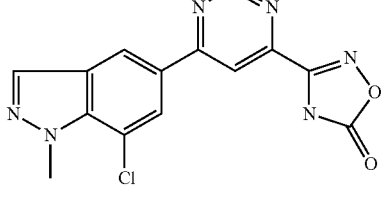

3-[6-(7-chloro-1-methyl-1H-indazol-5-
yl)pyrimidin-4-yl]-4,5-dihydro-1,2,4-oxadiazol-
5-one

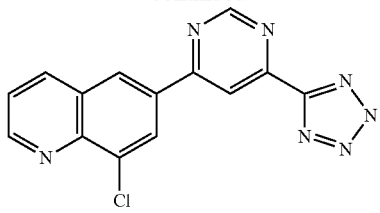

8-chloro-6-[6-(2H-1,2,3,4-tetrazol-5-
yl)pyrimidin-4-yl]quinoline

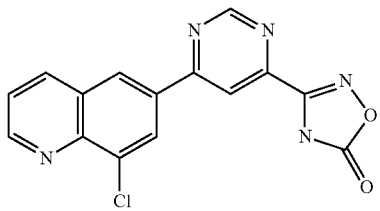

3-[6-(8-chloroquinolin-6-yl)pyrimidin-4-yl]-
4,5-dihydro-1,2,4-oxadiazol-5-one

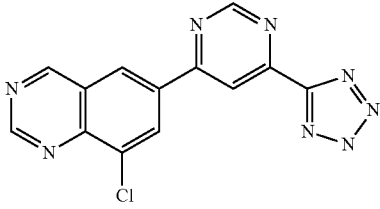

8-chloro-6-[6-(2H-1,2,3,4-tetrazol-5-
yl)pyrimidin-4-yl]quinazoline

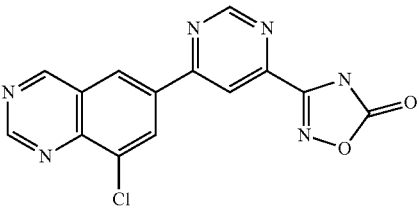

3-[6-(8-chloroquinazolin-6-yl)pyrimidin-4-yl]-
4,5-dihydro-1,2,4-oxadiazol-5-one

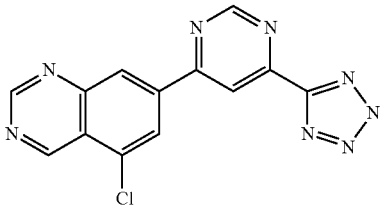

5-chloro-7-[6-(2H-1,2,3,4-tetrazol-5-
yl)pyrimidin-4-yl]quinazoline

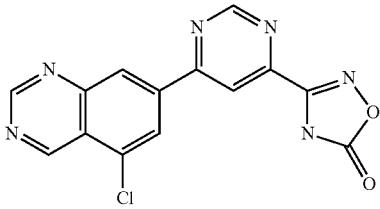

3-[6-(5-chloroquinazolin-7-yl)pyrimidin-4-yl]-
4,5-dihydro-1,2,4-oxadiazol-5-one

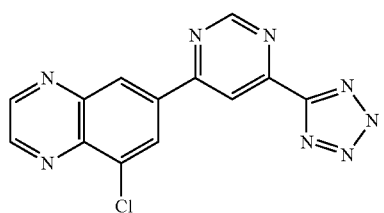

5-chloro-7-[6-(2H-1,2,3,4-tetrazol-5-yl)pyrimidin-4-yl]-quinoxaline

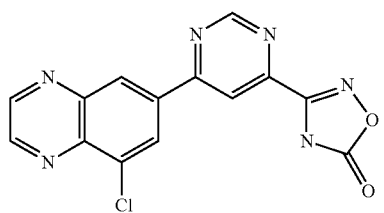

3-[6-(8-chloroquinoxalin-6-yl)pyrimidin-4-yl]-4,5-dihydro-1,2,4-oxadiazol-5-one

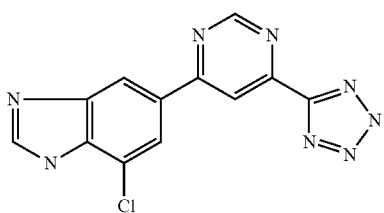

7-chloro-5-[6-(2H-1,2,3,4-tetrazol-5-yl)pyrimidin-4-yl]-1H-1,3-benzodiazole

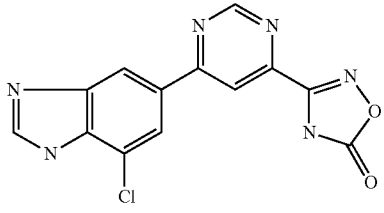

3-[6-(7-chloro-1H-1,3-benzodiazol-5-yl)pyrimidin-4-yl]-4,5-dihydro-1,2,4-oxadiazol-5-one

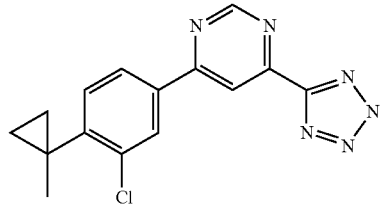

4-[3-chloro-4-(1-methylcyclopropyl)phenyl]-6-(2H-1,2,3,4-tetrazol-5-yl)pyrimidine

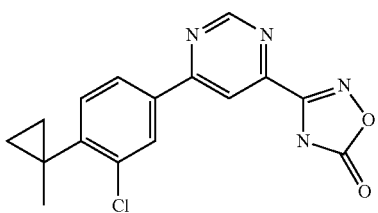

3-{6-[3-chloro-4-(1-methylcyclopropyl)phenyl]pyrimidin-4-yl}-4,5-dihydro-1,2,4-oxadiazol-5-one

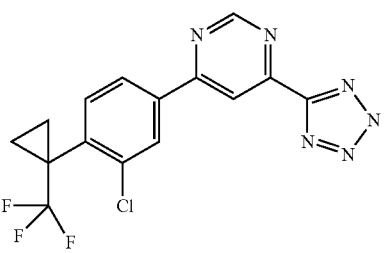

4-{3-chloro-4-(1-(trifluoromethyl)cyclopropyl]phenyl}-6-(2H-1,2,3,4-tetrazol-5-yl)pyrimidine

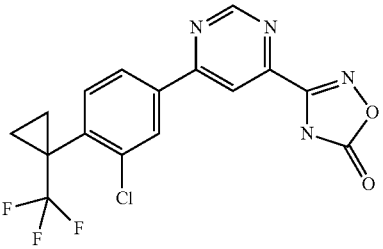

3-(6-{3-chloro-4-(1-(trifluoromethyl)cyclopropyl]phenyl}pyrimidin-4-yl)-4,5-dihydro-1,2,4-oxadiazol-5-one

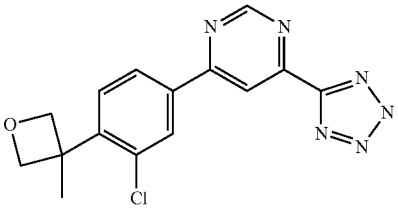

4-[3-chloro-4-(3-methyloxetan-3-yl)phenyl]-6-(2H-1,2,3,4-tetrazol-5-yl)pyrimidine

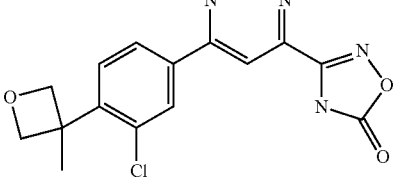

3-{6-[3-chloro-4-(3-methyloxetan-3-yl)phenyl]pyrimidin-4-yl}-4,5-dihydro-1,2,4-oxadiazol-5-one

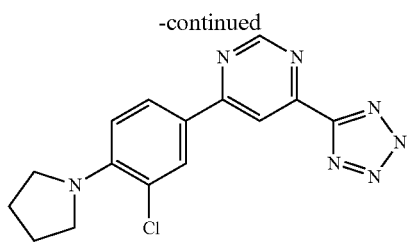

4-[3-chloro-4-(pyrrolidin-1-yl)phenyl]-6-(2H-1,2,3,4-tetrazol-5-yl)pyrimidine

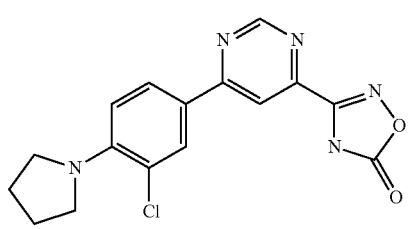

3-{6-[3-chloro-4-(pyrrolidin-1-yl)phenyl]pyrimidin-4-yl}-4,5-dihydro-1,2,4-oxadiazol-5-one

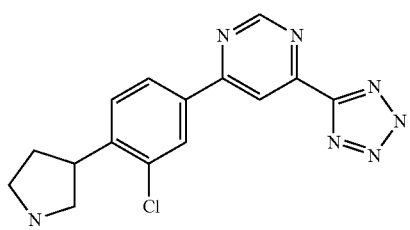

4-[3-chloro-4-(pyrrolidin-3-yl)phenyl]-6-(2H-1,2,3,4-tetrazol-5-yl)pyrimidine

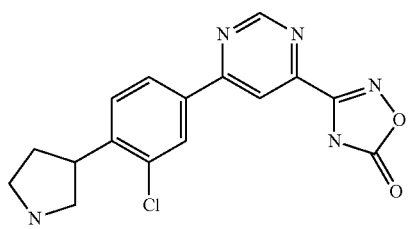

3-{6-[3-chloro-4-(pyrrolidin-3-yl)phenyl]pyrimidin-4-yl}-4,5-dihydro-1,2,4-oxadiazol-5-one

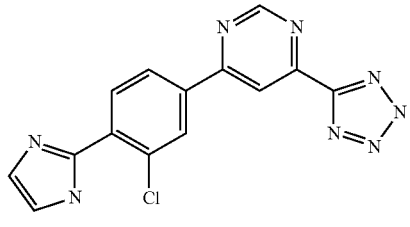

4-[3-chloro-4-(1H-imidazol-2-yl)phenyl]-6-(2H-1,2,3,4-tetrazol-5-yl)pyrimidine

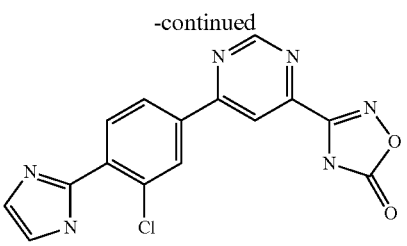

3-{6-[3-chloro-4-(1H-imidazol-2-yl)phenyl]pyrimidin-4-yl}-4,5-dihydro-1,2,4-oxadiazol-5-one

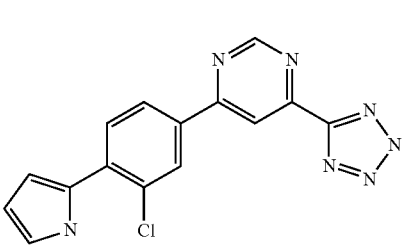

4-[3-chloro-4-(1H-pyrrol-2-yl)phenyl]-6-(2H-1,2,3,4-tetrazol-5-yl)pyrimidine

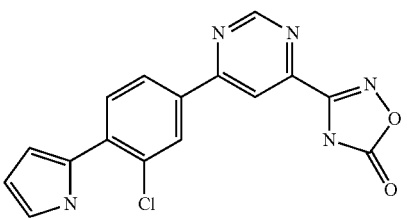

3-{6-[3-chloro-4-(1H-pyrrol-2-yl)phenyl]pyrimidin-4-yl}-4,5-dihydro-1,2,4-oxadiazol-5-one

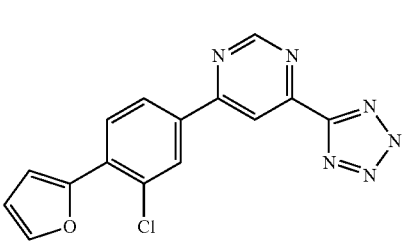

4-[3-chloro-4-(furan-2-yl)phenyl]-6-(2H-1,2,3,4-tetrazol-5-yl)pyrimidine

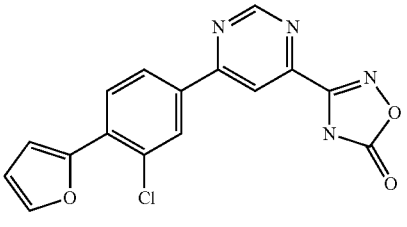

3-{6-[3-chloro-4-(furan-2-yl)phenyl]pyrimidin-4-yl}-4,5-dihydro-1,2,4-oxadiazol-5-one

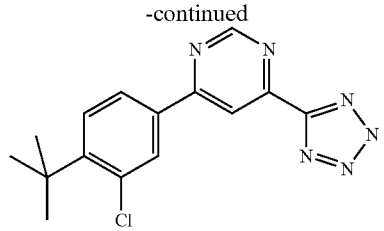

4-(4-tert-butyl-3-chlorophenyl-6-(2H-1,2,3,4-tetrazol-5-yl)pyrimidine

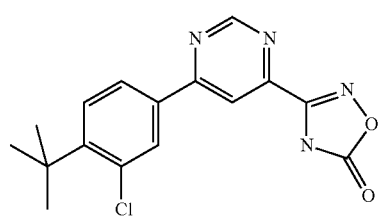

3-[6-(4-tert-butyl-3-chlorophenyl)pyrimidin-4-yl]-4,5-dihydro-1,2,4-oxadiazol-5-one

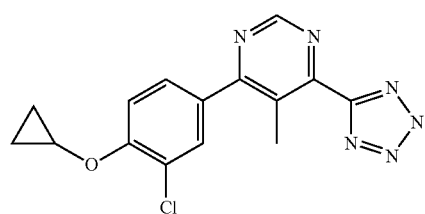

4-(3-chloro-4-cyclopropoxyphenyl)-5-methyl-6-(2H-1,2,3,4-tetrazol-5-yl)pyrimidine

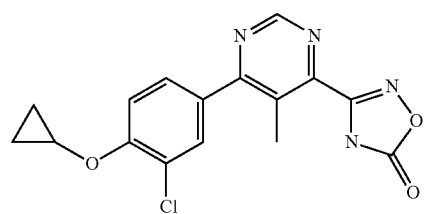

3-[6-(3-chloro-4-cyclopropoxyphenyl)-5-methylpyrimidin-4-yl]-4,5-dihydro-1,2,4-oxadiazol-5-one

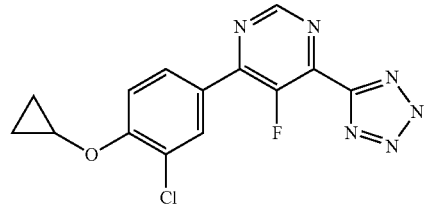

4-(3-chloro-4-cyclopropoxyphenyl)-5-fluoro-6-(2H-1,2,3,4-tetrazol-5-yl)pyrimidine

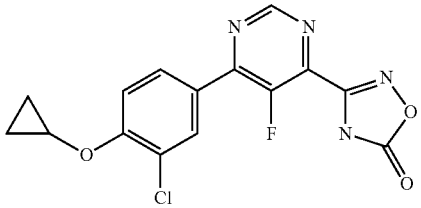

3-[6-(3-chloro-4-cyclopropoxyphenyl)-5-fluoropyrimidin-4-yl]-4,5-dihydro-1,2,4-oxadiazol-5-one

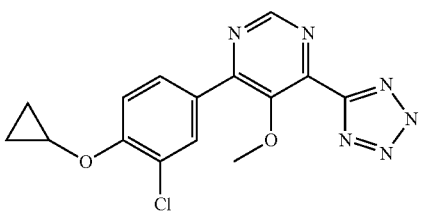

4-(3-chloro-4-cyclopropoxyphenyl)-5-methoxy-6-(2H-1,2,3,4-tetrazol-5-yl)pyrimidine

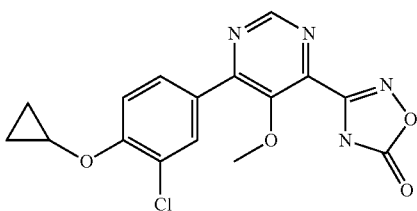

3-[6-(3-chloro-4-cyclopropoxyphenyl)-5-methoxypyrimidin-4-yl]-4,5-dihydro-1,2,4-oxadiazol-5-one

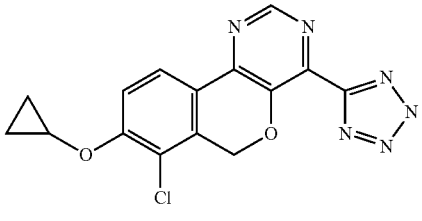

5-{7-chloro-8-cyclopropoxy-6H-isochromeno[4,3-d]pyrimidin-4-yl}-2H-1,2,3,4-tetrazole

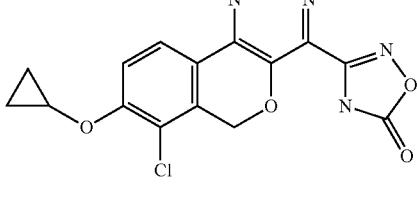

3-{7-chloro-8-cyclopropoxy-6H-isochromeno[4,3-d]pyrimidin-4-yl}-4,5-dihydro-1,2,4-oxadiazol-5-one -continued

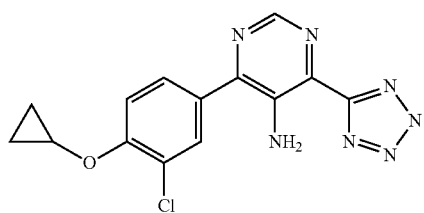

4-(3-chloro-4-cyclopropoxyphenyl)-6-(2H-1,2,3,4-tetrazol-5-yl)pyrimidine-5-amine

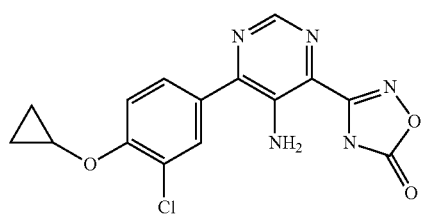

3-[5-amino-6-(3-chloro-4-cyclopropoxyphenyl)pyrimidin-4-yl]-4,5-dihydro-1,2,4-oxadiazol-5-one

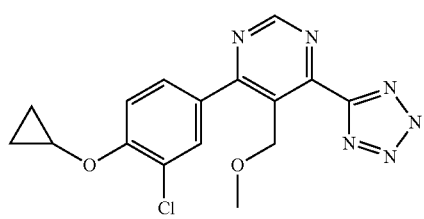

4-(3-chloro-4-cyclopropoxyphenyl)-5-(methoxymethyl)-6-(2H-1,2,3,4-tetrazol-5-yl)pyrimidine

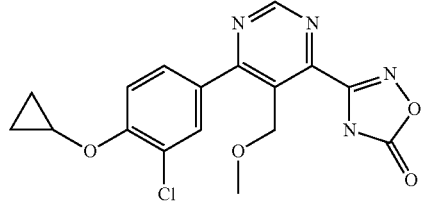

3-[6-(3-chloro-4-cyclopropoxyphenyl)-5-(methoxymethyl)pyrimidin-4-yl]-4,5-dihydro-1,2,4-oxadiazol-5-one

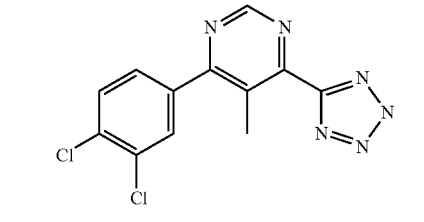

4-(3,4-dichlorophenyl)-5-methyl-6-(2H-1,2,3,4-tetrazol-5-yl)pyrimidine

-continued

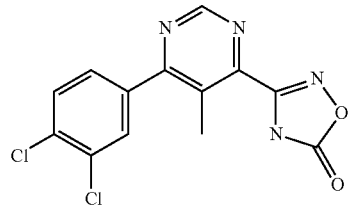

3-[6-(3,4-dichlorophenyl)-5-methylpyrimidin-4-yl]-4,5-dihydro-1,2,4-oxadiazol-5-one

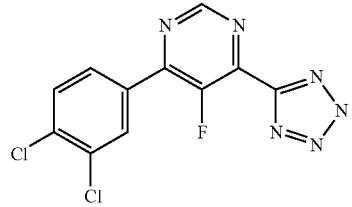

4-(3,4-dichlorophenyl)-5-fluoro-6-(2H-1,2,3,4-tetrazol-5-yl)pyrimidine

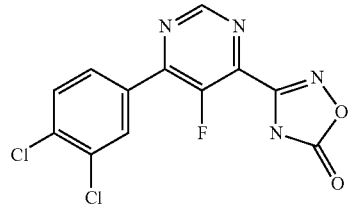

3-[6-(3,4-dichlorophenyl)-5-fluoropyrimidin-4-yl]-4,5-dihydro-1,2,4-oxadiazol-5-one

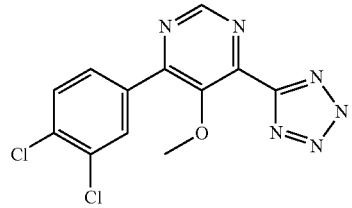

4-(3,4-dichlorophenyl)-5-methoxy-6-(2H-1,2,3,4-tetrazol-5-yl)pyrimidine

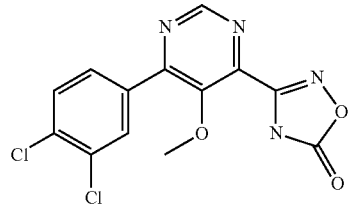

3-[6-(3,4-dichlorophenyl)-5-methoxypyrimidin-4-yl]-4,5-dihydro-1,2,4-oxadiazol-5-one

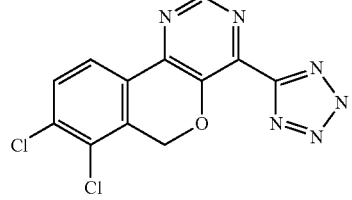

5-{7,8-dichloro-6H-isochromeno[4,3-d]pyrimidin-4-yl}-2H-1,2,3,4-tetrazol

-continued

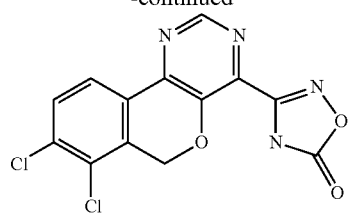

3-{7,8-dichloro-6H-isochromeno[4,3-d]pyrimidin-4-yl}-4,5-dihydro-1,2,4-oxadiazol-5-one

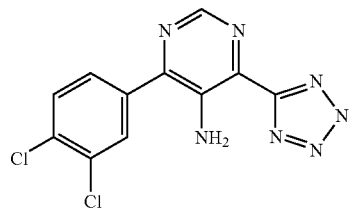

4-(3,4-dichlorophenyl)-6-(2H-1,2,3,4-tetrazol-5-yl)pyrimidin-5-amine

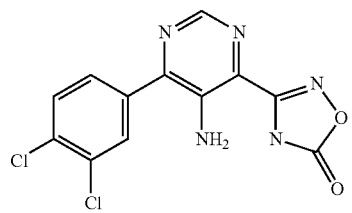

3-[5-amino-6-(3,4-dichlorophenyl)pyrimidin-4-yl]-4,5-dihydro-1,2,4-oxadiazol-5-one

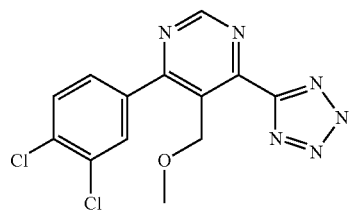

4-(3,4-dichlorophenyl)-5-(methoxymethyl)-6-(2H-1,2,3,4-tetrazol-5-yl)pyrimidine

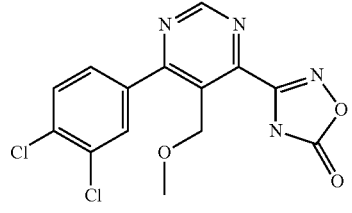

3-[6-(3,4-dichlorophenyl)-5-(methoxymethyl)pyrimidin-4-yl]-4,5-dihydro-1,2,4-oxadiazol-5-one -continued

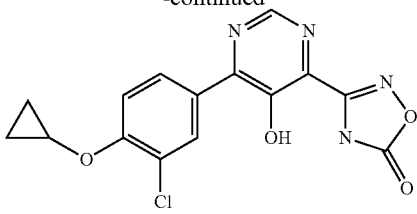

4-(3-chloro-4-cyclopropoxyphenyl)-6-(2H-1,2,3,4-tetrazol-5-yl)-pyrimidin-5-ol

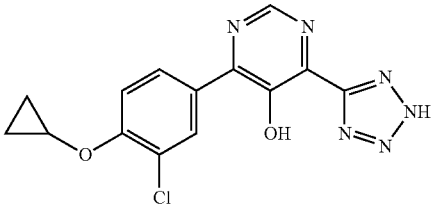

3-[6-(3-chloro-4-cyclopropoxyphenyl)-5-hydroxypyrimidin-4-yl]-4,5-dihydro-1,2,4-oxadiazol-5-one

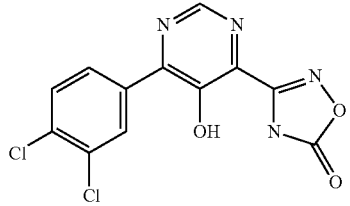

4-(3,4-dichlorophenyl)-6-(2H-1,2,3,4-tetrazol-5-yl)pyrimidin-5-ol

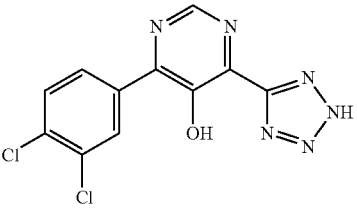

3-[6-(3,4-dichlorophenyl)-5-hydroxypyrimidin-4-yl]-4,5-dihydro-1,2,4-oxadiazol-5-one and pharmaceutically acceptable salts and prodrugs thereof.

Also provided is a method of treating a condition or disorder mediated by Kynurenine 3-mono-oxygenase activity in a subject in need of such a treatment which method comprises administering to the subject a therapeutically effective amount of at least one chemical entity described herein.

Methods for obtaining the chemical entities described herein will be apparent to those of ordinary skill in the art, suitable procedures being described, for example, in examples below, and in the references cited herein.

Provided is a method of inhibiting the catalytic activity of KMO, comprising contacting said KMO with an effective amount of at least one chemical entity described herein.

Also provided is a method of treating a condition or disorder mediated by KMO activity in a subject in need of such a treatment, comprising administering to the subject a therapeutically effective amount of at least one chemical entity described herein.

Also provided is a method of treating a neurodegenerative pathology mediated by KMO activity in a subject in need of such a treatment, comprising administering to the subject a therapeutically effective amount of at least one chemical entity described herein.

Also provided is a method for treating disorders mediated by (or at least in part by) the presence 3-OH-KYN, QUIN and/or KYNA. Also provided is a method of treating a degenerative or inflammatory condition in which an increased synthesis in the brain of QUIN, 3-OH-KYN or increased release of GLU are involved and which may cause neuronal damage.

Such diseases include, for example, Huntington's disease and other polyglutamine disorders such as spinocerebellar ataxias neurodegenerative diseases, psychiatric of neurological diseases or disorders, Alzheimer's disease, Parkinson's disease, amyotropic lateral sclerosis, Creutzfeld-Jacob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, Dementia such as senile dementia and AIDS-dementia complex, AIDS-induced encephalopathy, other infection related encephalopathy, viral or bacterial meningitis, infectious diseases caused by viral, bacterial and other parasites, for example, general central nervous system (CNS) infections such as viral, bacterial or parasites, for example, poliomyelitis, Lyme disease (*Borrelia burgdorferi* infection) septic shock, and malaria, cancers, cancers with cerebral localization, hepatic encephalopathy, systemic lupus, analgesia and opiate withdrawal symptoms, feeding behavior, psychiatric disorders, such as insomnia, depression, schizophrenia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, ondougenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders. Such disease also include, for example, Acute necrotizing Pancreatitis, AIDS (disease), Analgesia, Aseptic meningitis, Brain disease, for example, Gilles de la Tourette syndrome, Asperger syndrome, Rett syndrome, pervasive developmental disorders, aging-related Brain disease, and developmental Brain disease, burnout syndrome, carbon monoxide poisoning, cardiac arrest or insufficiency and hemorrhagic shock (global brain ischemia), cataract formation and aging of the eye, Central nervous system disease, Cerebrovascular disease, chronic fatigue syndrome, Chronic Stress, Cognitive disorders, convulsive Disorders, such as variants of Grand mal and petit mal epilepsy and Partial Complex Epilepsy, Diabetes mellitus, Disease of the nervous system (e.g., dyskinesia, L-DOPA induced movement disorders, drug addiction, pain and cataract), Drug dependence, Drug withdrawal, feeding disorders, Guillain Barr Syndrome and other neurophaties, Hepatic encephalopathy, Immune disease, immunitary disorders and therapeutic treatment aimed at modifying biological responses (for instance administrations of interferons or interleukins), Inflammation (systemic inflammatory response syndrome), inflammatory disorders of the central and/or peripheral nervous system, Injury (trauma, polytrauma), Mental and behavioral disorders, Metabolic disease, pain disease, or disorder selected from a group of inflammatory pain, neurophathic pain or migraine, allodynia, hyperalgesis pain, phantom pain, neurophatic pain related to diabetic neuropathy, Multiple organ failure, near drowning, Necrosis, neoplasms of the brain, neoplastic disorders including lymphomas and other malignant blood disorders, Nervous system disease (high-pressure neurol. Syndrome, infection), nicotine addiction and other addictive disorders including alcoholism, cannabis, benzodiazepine, barbiturate, morphine and cocaine dependence, change in appetite, sleep disorders, changes in sleep pattern, lack of energy, fatigue, low self esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a Neuroprotective agents, Pain, Post-traumatic stress disorder, Sepsis, Spinal cord disease, Spinocerebellar ataxia, Systemic lupus erythematosis, traumatic damage to the brain and spinal cord, and tremor syndromes and different movement disorders (diskynesia). Poor balance, brakykinesia, rigidity, tremor, change in speech, loss of facial expression, micrographia, difficulty swallowing, drooling, dementia, confusion, fear, sexual disfunction, language impairment, impairment in decision making, violent outbursts, aggression, hallucination, apathy, impairment in abstract thinking.

Such diseases include, for example, cardiovascular diseases, which refers to diseases and disorders of the heart and circulatory system. These diseases are often associated with dyslipoproteinemias and/or dyslipidemias. Cardiovascular diseases include but are not limited to cardiomegaly, atherosclerosis, myocardial infarction, and congestive heart failure, coronary heart disease, hypertension and hypotension.

Other such diseases include hyperproliferative diseases of benign or malignant behaviour, in which cells of various tissues and organs exhibit aberrant patterns of growth, proliferation, migration, signaling, senescence, and death. Generally hyperpoliferative disease refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopaties, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorders of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

Additional diseases include transplant rejection (suppression of T-cells) and graft vs host disease, chronic kidney disease, systemic inflammatory disorders, brain inflammatory disorders including malaria and African trypanosomiasis, stroke, and pneumococcal meningitis.

Also provided are methods of treatment in which at least one chemical entity described herein is the only active agent given to the subject and also includes methods of treatment in which at least one chemical entity described herein is given to the subject in combination with one or more additional active agents.

In general, the chemical entities described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the chemical entities described herein are administered as a pharmaceutical composition. Accordingly, provided are pharmaceutical compositions comprising at least one chemical entity described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity described herein.

Effective concentrations of at least one chemical entity described herein are mixed with a suitable pharmaceutically acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one chemical entity described herein. In some embodiments, oral pharmaceutical compositions contain at least 5% (weight %) of at least one chemical entity described herein. Some embodiments contain from 25% to 50% or from 5% to 75% of at least one chemical entity described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

Chemical entities described herein can be incorporated into oral liquid preparations such as aqueous or oily suspensions, solutions, emulsions, syrups, or elixirs, for example. Moreover, pharmaceutical compositions containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entities described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical pharmaceutical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the chemical entity include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one chemical entity described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one chemical entity described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the chemical entities can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one chemical entity described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one chemical entity described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one chemical entity described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one chemical entity described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one chemical entity described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one chemical entity described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one chemical entity described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one chemical entity described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one chemical entity described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia or cognitive impairment comprising administering to a subject, simultaneously or sequentially, at least one chemical entity and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one chemical entity described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one chemical entity described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one chemical entity described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one chemical entity described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Also provided are packaged pharmaceutical compositions containing a pharmaceutical composition comprising at least one chemical entity described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one chemical entity described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one chemical entity described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one chemical entity described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

The methods described herein include methods for treating cancer, comprising administering to a subject, simultaneously or sequentially, at least one chemical entity described herein and one or more additional agents used in the treatment of cancer such as, but not limited to, pacliataxel, bortezomib, dacarbazine, gemcitabine, trastuzumab, bevacizumab, capecitabine, docetaxel, oxaliplatin, Leuprolide, Anastrozole, Gemcitabine, Bicalutamide, Cetuximab, Irinotecan, Letrozole, Pemetrexed, erlotinib, aromatase inhibitors, such as AROMASIN™ (exemestane), and estrogen receptor inhibitors, such as FASLODEX™ (fulvestrant). In methods using simultaneous administration, the agents can be present in a combined composition or can be administered separately. As a result, also provided are pharmaceutical compositions comprising at least one chemical entity described herein and one or more additional pharmaceutical agents used in the treatment of cancer such as, but not limited to, pacliataxel, bortezomib, dacarbazine, gemcitabine, trastuzumab, bevacizumab, capecitabine, docetaxel, oxaliplatin, Leuprolide, Anastrozole, Gemcitabine, Bicalutamide, Cetuximab, Irinotecan, Letrozole, Pemetrexed, erlotinib, aromatase inhibitors, such as AROMASIN™ (exemestane), and estrogen receptor inhibitors, such as FASLODEX™ (fulvestrant). Similarly, also provided are packaged pharmaceutical compositions containing a pharmaceutical composition comprising at least one chemical entity described herein, and another composition comprising one or more additional pharmaceutical agents used in the treatment of cancer such as, but not limited to, pacliataxel, bortezomib, dacarbazine, gemcitabine, trastuzumab, bevacizumab, capecitabine, docetaxel, oxaliplatin, Leuprolide, Anastrozole, Gemcitabine, Bicalutamide, Cetuximab, Irinotecan, Letrozole, Pemetrexed, erlotinib, aromatase inhibitors, such as AROMASIN™ (exemestane), and estrogen receptor inhibitors, such as FASLODEX™ (fulvestrant).

When used in combination with one or more additional pharmaceutical agent or agents, the described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The chemical entities described herein are typically administered at dosage levels and in a manner customary for KMO inhibitors. For example, the chemical entities can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one chemical entity described herein, for example, 0.1-50 mg of at least one chemical entity described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one chemical entity described herein.

A labeled form of a chemical entity described herein can be used as a diagnostic for identifying and/or obtaining compounds that have the function of modulating an activity of KMO as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The chemical entities, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=1-Hydroxybenzotriazol
LiHMDS=lithium hexamethyl-disilazide
LC/MS=liquid chromatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate
μL=microliter
μM=micromolar
1 g/1 ml=1 vol Experimental Commercially available reagents and solvents (HPLC grade) were used without further purification.

Thin-layer chromatography (TLC) analysis was performed with Kieselgel 60 F$_{254}$ (Merck) plates and visualized using UV light. Microwave reactions were carried out using CEM focussed microwaves.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μl, flow=1.0 ml/min UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software.

Example 1

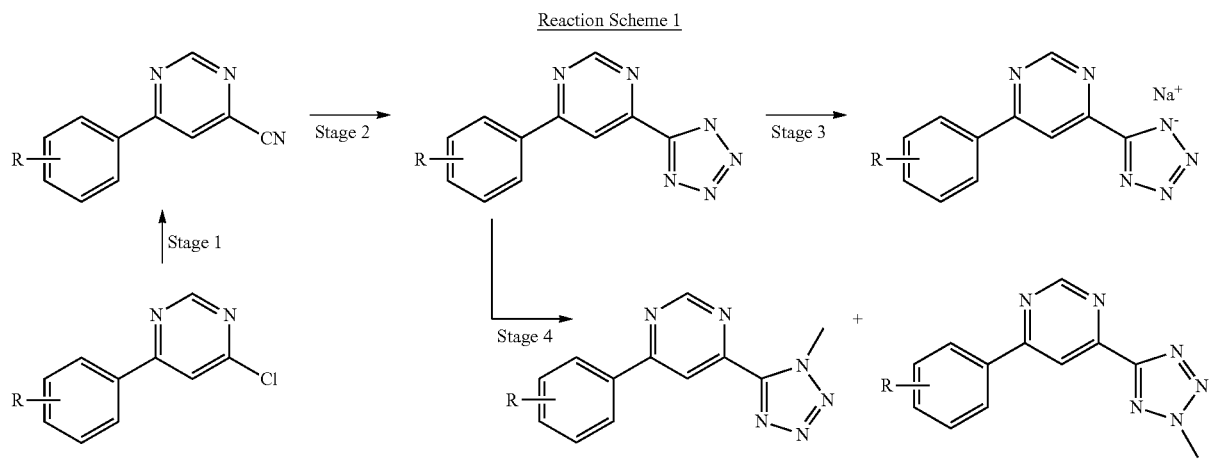

Reaction Scheme 1

Referring to Reaction Scheme 1, Stage 1, to a solution of 4-chloro-6-(substituted-phenyl)1-pyrimidine (1 eq) in degassed DMF (20 vol) was added Pd(PPh$_3$)$_4$ (0.05 eq) followed by zinc cyanide (1 eq). The reaction mixture was heated at 100° C. until completion of the reaction whereupon it was cooled to room temperature. Water (37.5 vol) was added to the reaction mixture, which was extracted with EtOAc (150 vol). The organic layer was washed with water (1000 vol), followed by saturated aqueous NaCl solution (200 vol), dried over MgSO4, filtered and concentrated in vacuo. Purification by flash column chromatography (eluent: [0:1 to 1:1] EtOAc:heptane) afforded the target compounds.

Referring to Reaction Scheme 1, Stage 2, a solution of 6-(substituted-phenyl)-pyrimidine-4-carbonitrile (1 eq), sodium azide (12 eq) and ammonium chloride (12 eq) in DMF (46 vol) was heated in the microwave at 200° C., 20 Watts with stirring for 15 minutes. The reaction mixture was added to a saturated solution of NaHCO3 and washed with EtOAc (4×). The aqueous phase was then acidified to pH 1 using concentrated HCl, provoking the precipitation of the desired product, which was filtered off and washed with water.

Referring to Reaction Scheme 1, Stage 3,4-Substituted-phenyl-6-(1H-tetrazol-5-yl)-pyrimidine was triturated in a solution of 2M NaOH (7.3 eq), filtered, washed with water (2×) and acetone (2×) to furnish the desired sodium salt.

Referring to Reaction Scheme 1, Stage 4, to a stirred solution of 4-substituted-phenyl-6-(1H-tetrazol-5-yl)-pyrimidine (1 eq) in DMF (15 vol) at 0° C. was added sodium hydride (1 eq). The resulting mixture was stirred at 0° C. for 20 minutes, after which time methyl iodide (2 eq) was added. The reaction mixture was then stirred at room temperature for 2 hours and then at 40° C. for 1 hour. The reaction mixture was poured into water and extracted with EtOAc, dried over Na$_2$SO$_4$, filtered and concentrated in vacuo. Purification by flash column chromatography (eluent: [0:1 to 1:1] EtOAc:heptane) afforded the target compounds.

The following compounds were prepared substantially as described above.

| Structure | Molecular Weight | Mass Spec Result |
|---|---|---|
| 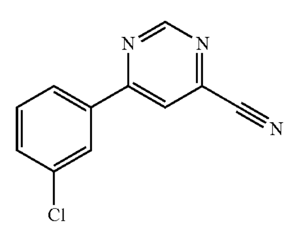 [SMILES: N#Cc1cc(-c2cccc(Cl)c2)ncn1] | 215.64 | [M + H]$^+$ = 215/218, 100% @ rt = 4.50 min |
| 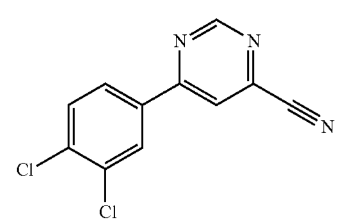 [SMILES: N#Cc1cc(-c2ccc(Cl)c(Cl)c2)ncn1] | 250.09 | [M + H]$^+$ = 249/251, 100% @ rt = 4.96 min |

-continued

| Structure | Molecular Weight | Mass Spec Result |
|---|---|---|
| 3-chlorophenyl-pyrimidine-tetrazole | 258.67 | [M + H]⁺ = 259, 100% @ rt = 4.06 min |
| 3-chlorophenyl-pyrimidine-(1-methyl)tetrazole | 272.7 | [M + H]⁺ = 273, 99% @ rt = 4.40 min |
| 3-chlorophenyl-pyrimidine-(2-methyl)tetrazole | 272.7 | [M + H]⁺ = 273, 99% @ rt = 4.18 min |
| 3,4-dichlorophenyl-pyrimidine-tetrazole | 293.12 | [M + H]⁺ = 292/294, 100% @ rt = 4.39 min |
| 3,4-dichlorophenyl-pyrimidine-(1-methyl)tetrazole | 307.14 | [M + H]⁺ = 306/308, 98% @ rt = 4.77 min |
| 3,4-dichlorophenyl-pyrimidine-(2-methyl)tetrazole | 307.14 | [M + H]⁺ = 306/308, 97% @ rt = 4.58 min |
| 3,4-dichlorophenyl-pyrimidine-tetrazolide Na⁺ | 315.1 | [M + H]⁺ = 292, 100% @ rt = 4.50 min |

-continued

| Structure | Molecular Weight | Mass Spec Result |
|---|---|---|
| [3,4-difluorophenyl-pyrimidine-tetrazole] | 260.21 | [M + H]⁺ = 261, 100% @ rt = 3.78 min |
| [3,4-difluorophenyl-pyrimidine-tetrazole Na⁺ salt] | 282.19 | [M + H]⁺ = 261, 100% @ rt = 3.78 min |
| [3-chloro-4-fluorophenyl-pyrimidine-tetrazole] | 276.66 | [M + H]⁺ = 277, 100% @ rt = 3.96 min |
| [3-chloro-4-fluorophenyl-pyrimidine-tetrazole Na⁺ salt] | 298.64 | [M + H]⁺ = 277, 94% @ rt = 4.07 min |
| [3-fluoro-4-methylphenyl-pyrimidine-tetrazole] | 256.24 | [M + H]⁺ = 257, 100% @ rt = 3.78 min |
| [3-chloro-4-isopropoxyphenyl-pyrimidine-tetrazole] | 316.75 | [M + H]⁺ = 317/318.6, 100% @ rt = 4.18 min |

| Structure | Molecular Weight | Mass Spec Result |
|---|---|---|
| (structure with OCF3, Cl phenyl-pyrimidine-tetrazole) | 342.67 | [M + H]⁺ = 343/345, 100% @ rt = 4.45 min |
| (structure with cyclopropyl-O, Cl phenyl-pyrimidine-tetrazole) | 314.73 | [M + H]+ = 315/317, 100% @ rt = 4.04 min |

Example 2

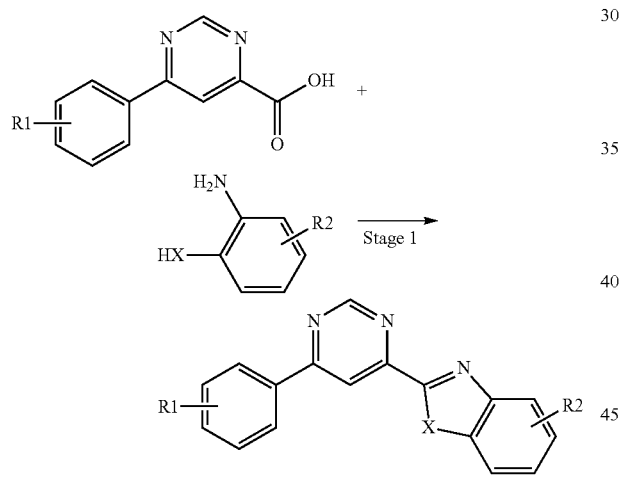

Reaction Scheme 2

Referring to Reaction Scheme 2, Stage 1, to a stirred solution of 6-(substituted-phenyl)-pyrimidine-4-carboxylic acid (1 eq) in DMF (6 vol) was added EDC.HCl (2 eq), HOBt (1.1 eq) and the appropriate aniline (1.1 eq). The reaction mixture was stirred at ambient temperature for 16 hours and the solvent was removed in vacuo. Trituration of the residue with acetonitrile/water (1/1) afforded the intermediate, which was heated in a pressure tube at temperatures varying between 120° C. and 170° C. depending which aniline was used for 16 hours. The reaction mixture was allowed to cool to room temperature and quenched with NaHCO₃. The resulting precipitate was filtered and washed with water and methanol. It was further purified by prep HPLC when required to furnish the desired target compound.

The following compounds were prepared substantially as described above.

| Structure | Molecular Weight | Mass Spec Result |
|---|---|---|
| (3-Cl-phenyl-pyrimidine-benzimidazole) | 306.76 | [M + H]⁺ = 307, 100% @ rt = 4.55 min |

| Structure | Molecular Weight | Mass Spec Result |
|---|---|---|
| 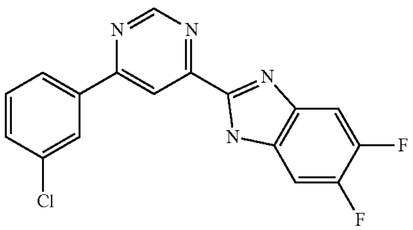 [SMILES: Fc1cc2nc(-c3cc(-c4cccc(Cl)c4)ncn3)[nH]c2cc1F] | 342.74 | [M + H]+ = 342, 100% @ rt = 4.97 min |
| 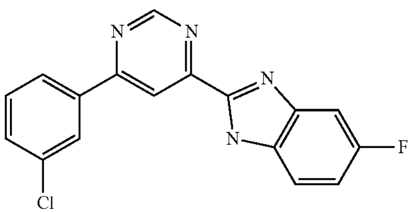 [SMILES: Fc1ccc2[nH]c(-c3cc(-c4cccc(Cl)c4)ncn3)nc2c1] | 324.75 | [M + H]+ = 325, 100% @ rt = 4.82 min |
| 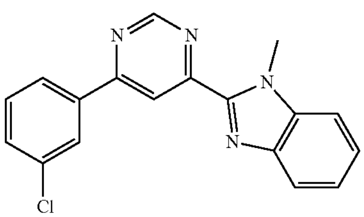 | 320.78 | [M + H]+ = 321, 100% @ rt = 5.14 min |
| | 341.2 | [M + H]+ = 340, 97% @ rt = 5.09 min |
| | 341.2 | [M + H]+ = 340, 100% @ rt = 4.97 min |
| 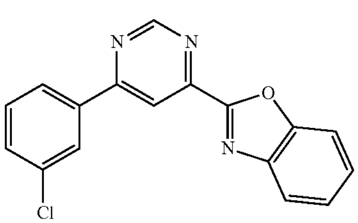 [SMILES: Clc1cccc(-c2cc(-c3nc4ccccc4o3)ncn2)c1] | 307.74 | [M + H]+ = 308, 100% @ rt = 5.12 min |

Example 3

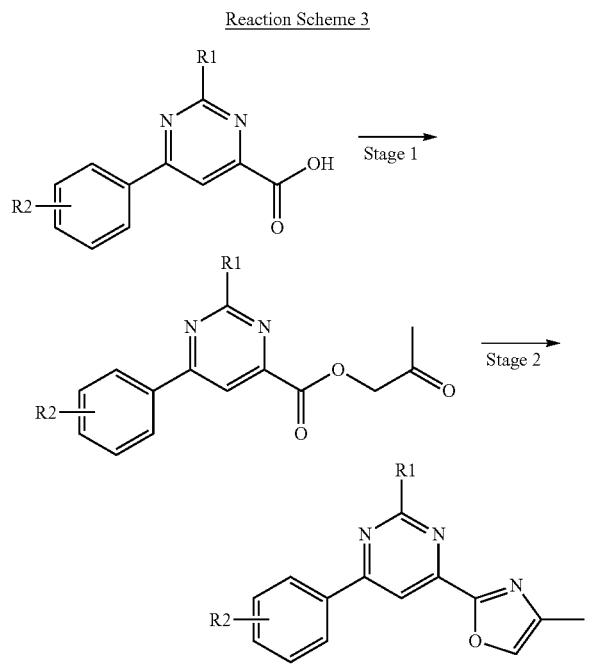

Referring to Reaction Scheme 3, Stage 1, to a stirred solution of 2-methyl-6-(substituted-phenyl)-pyrimidine-4-carboxylic acid (1 eq) or 6-(substituted-phenyl)-pyrimidine-4-carboxylic acid (1 eq) in DMF (15 vol) was added triethylamine (1.05 eq) and chloroacetone (1.05 eq) and the reaction mixture was stirred at ambient temperature for 16 hours. Water (35 vol) was added to the reaction mixture, which was filtered to furnish the ester intermediate as a pale brown solid. The ester intermediate was washed with water, dried in a vacuum oven for 16 hours and used in the next stage without further purification.

Referring to Reaction Scheme 3, Stage 2, to a stirred solution of the previous ester intermediate (1 eq) in acetic acid (23 vol) was added ammonium acetate (4 eq) and the reaction mixture was heated at 115° C. with stirring for 2 hours. It was allowed to cool to room temperature and solvent removed in vacuo. The resulting black solid was dissolved in EtOAc and washed with water, saturated aqueous NaCl solution, dried with $MgSO_4$, filtered and the solvent removed in vacuo. Purification by column chromatography (eluent: [0:1 to 1:4] EtOAc:heptane) afforded the required target compound.

The following compounds were prepared substantially as described above.

| Structure | Molecular Weight | Mass Spec Result |
|---|---|---|
| 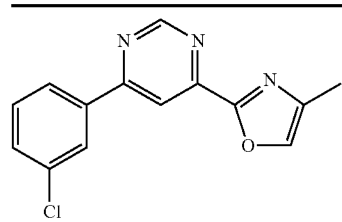 | 271.71 | $[M + H]^+$ = 272/274, 100% @ rt = 4.49 min |
| 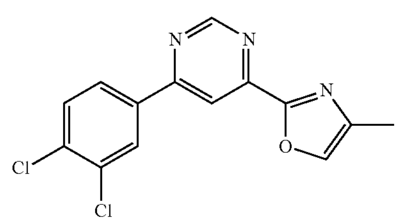 [SMILES: Cc1coc(-c2cc(-c3ccc(Cl)c(Cl)c3)ncn2)n1] | 306.15 | $[M + H]^+$ = 305, 97% @ rt = 4.95 min |
| 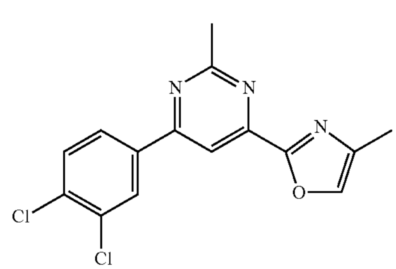 [SMILES: Cc1coc(-c2cc(-c3ccc(Cl)c(Cl)c3)nc(C)n2)n1] | 320.18 | $[M + H]^+$ = 321, 100% @ rt = 5.42 min |

Example 4

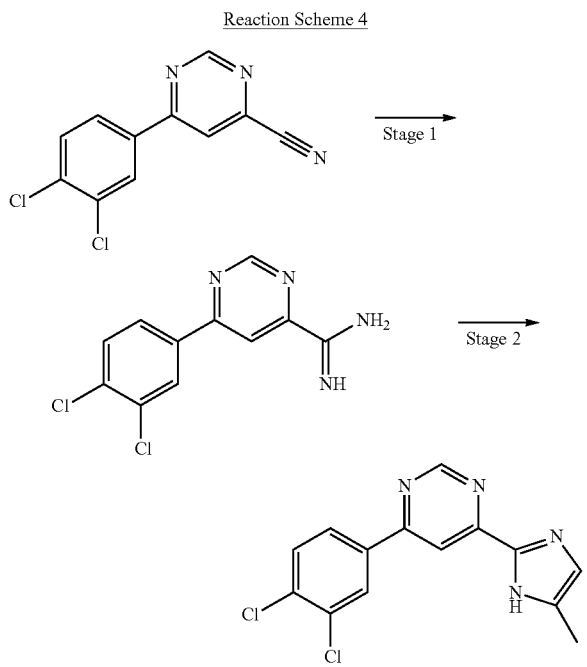

Referring to Reaction Scheme 4, Stage 1, to a stirred solution of 6-(3,4-dichloro-phenyl)-pyrimidine-4-carbonitrile (1 eq) in anhydrous toluene (20 vol) at 0° C. was added lithium hexamethyldisilazide (2 eq) and the reaction mixture was stirred at ambient temperature for 2 hours under an atmosphere of nitrogen. The reaction mixture was cooled to 0° C. and quenched with HCl (3M). After 30 minutes stirring, water (40 vol) was added, followed by toluene (20 vol). The mixture was partitioned and the precipitate present in the aqueous phase was filtered off. The solid was suspended in a 3M solution of sodium hydroxide, stirred at room temperature for 30 minutes to give 6-(3,4-dichloro-phenyl)-pyrimidine-4-carboxamidine, which was used in the next stage without further purification.

Referring to Reaction Scheme 4, Stage 2, to a stirred solution of 6-(3,4-dichloro-phenyl)-pyrimidine-4-carboxamidine (1 eq) in 1,4-dioxane (10 vol) was added chloroacetone (0.33 eq) and the reaction mixture was stirred at 100° C. in a sealed pressure tube for 4 hours. The reaction mixture was allowed to cool to room temperature. Diisopropylethylamine (1 eq) and chloroacetone (0.33 eq) were added to the reaction mixture, which was stirred at 110° C. for 16 hours. The solvent was removed in vacuo and the resulting solid was triturated with water, filtered and washed with methanol. Purification by prep HPLC furnished the desired target compound.

The following compounds were prepared substantially as described above.

| Structure | Molecular Weight | Mass Spec Result |
|---|---|---|
| 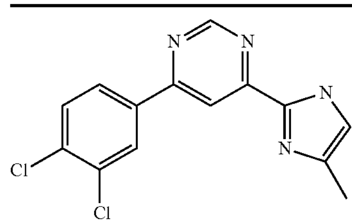 | 305.17 | $[M + H]^+$ = 304, 95% @ rt = 3.47 min |

Example 5

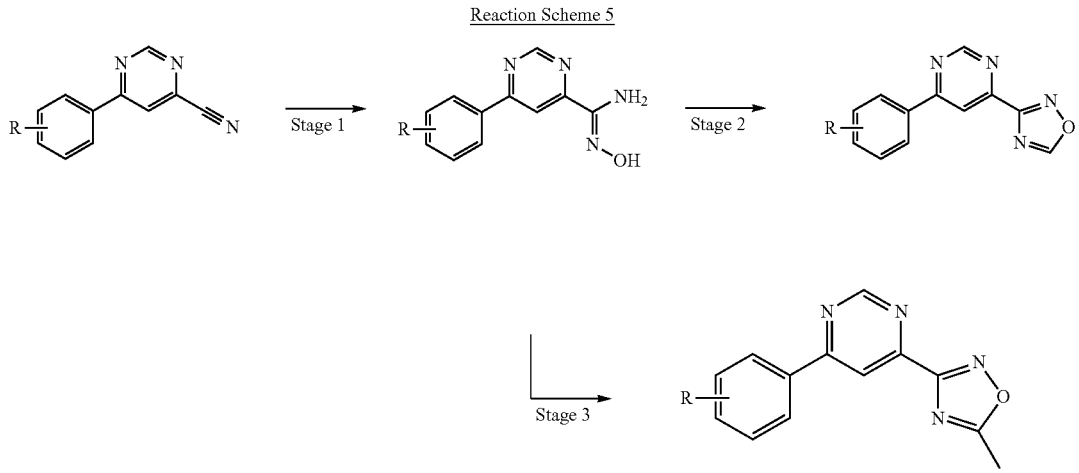

Referring to Reaction Scheme 5, Stage 1, to a stirred solution of 6-(substituted-phenyl)-pyrimidine-4-carbonitrile (1 eq) in ethanol (25 vol) was added hydroxylamine hydrochloride (1.05 eq), followed by diisopropylethylamine (1.05 eq). The reaction mixture was heated at 70° C. for 1 hour. It was allowed to cool to room temperature and diluted with EtOAc (750 vol). The organic layer was washed with water (2500 vol) and with a saturated aqueous NaCl solution (2500 vol), dried with MgSO$_4$, filtered and the solvent removed in vacuo to give the desired intermediate as a yellow powder, which was used without any further purification in the next stage.

Referring to Reaction Scheme 5, Stage 2, to a stirred solution of N-hydroxy-6-(substituted-phenyl)-pyrimidine-4-carboxamidine (1 eq) in trimethylorthoformate (25 vol) was added concentrated HCl (cat.). The reaction mixture was heated at 100° C. with stirring for 1 hour. It was then allowed to cool down to room temperature and the resulting precipitate was filtered off and washed with heptane to furnish the desired target compound.

Referring to Reaction Scheme 5, Stage 3, To a stirred solution of N-hydroxy-6-(substituted-phenyl)-pyrimidine-4-carboxamidine (1 eq) in pyridine (25 vol) was added acetyl chloride (2 eq) The reaction mixture was heated at 105° C. for 2 hours after which time acetyl chloride (1 eq) was added to the reaction mixture, which was heated for another 2.5 hours. It was then allowed to cool to room temperature and was diluted with water (800 vol). The desired compound was isolated by filtration and purified by flash column chromatography (eluent EtOAc:heptane).

The following compounds were prepared substantially as described above.

| Structure | Molecular Weight | Mass Spec Result |
|---|---|---|
| 3,4-dichlorophenyl-pyrimidine-1,2,4-oxadiazole | 293.11 | [M + H]$^+$ = 292, 100% @ rt = 4.63 min |
| 3,4-dichlorophenyl-pyrimidine-5-methyl-1,2,4-oxadiazole | 307.14 | [M + H]$^+$ = 306, 100% @ rt = 4.81 min |

Example 6

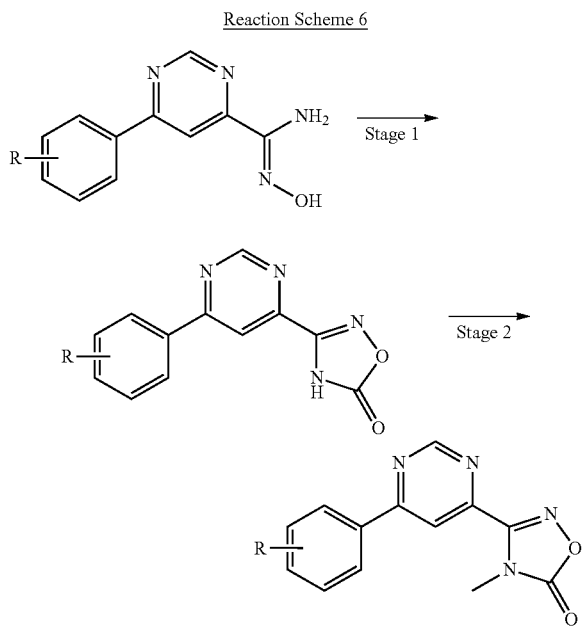

Referring to Reaction Scheme 6, Stage 1, to a stirred solution of N-hydroxy-6-(substituted-phenyl)-pyrimidine-4-carboxamidine (1 eq) in 1,4-dioxane (16 vol) was added 1,1'-carbonyldiimidazole (1.24 eq), 1,8-diazabicyclo[5.4.0]undec-7-ene (1.07 eq) and the reaction mixture was stirred at 110° C. for 3 hours. The reaction was allowed to cool down to room temperature and the solvent removed in vacuo. The resulting residue was dissolved in water and EtOAc. The aqueous layer was isolated and washed with EtOAc (3×). It was then acidified to pH1 with a 2M HCl solution and extracted with EtOAc (3×). The organic phases were combined and washed with a saturated aqueous NaCl solution (50 vol), dried over MgSO$_4$, filtered and concentrated in vacuo.

Referring to Reaction Scheme 6, Stage 2, to a stirred solution of 3-(6-(substituted-phenyl)-pyrimidin-4-yl)-4H-[1,2,4]oxadiazol-5-one in DMF (20 vol) at 0° C. was added sodium hydride (1 eq) and the reaction mixture was stirred at this temperature for 15 minutes. Methyl iodide (2 eq) was added and the reaction mixture was stirred at ambient temperature for 1.5 hours, followed by stirring at 30° C. for 45 minutes. Addition of water provoked the precipitation of the desired target compound, which was isolated by filtration and washed with water (500 vol) and heptane (1000 vol).

The following compounds were prepared substantially as described above.

| Structure | Molecular Weight | Mass Spec Result |
|---|---|---|
| 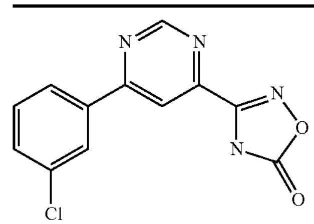 | 274.67 | [M + H]$^+$ = 274, 100% @ rt = 4.41 min |
| 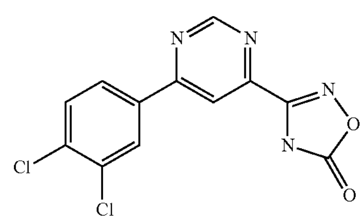 | 309.11 | [M + H]$^+$ = 308, 97% @ rt = 4.57 min |
| 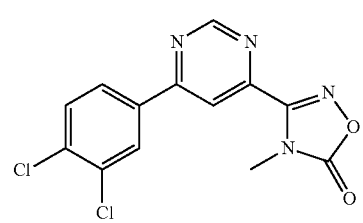 [SMILES: Cn1c(-c2cc(-c3ccc(Cl)c(Cl)c3)ncn2)noc1=O] | 323.14 | [M + H]$^+$ = 322, 100% @ rt = 4.82 min |
| 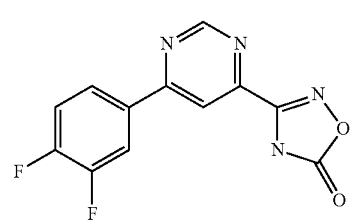 [SMILES: O=c1[nH]c(-c2cc(-c3ccc(F)c(F)c3)ncn2)no1] | 276.2 | [M + H]$^+$ = 277, 100% @ rt = 3.81 min |

-continued
| Structure | Molecular Weight | Mass Spec Result |
|---|---|---|
| 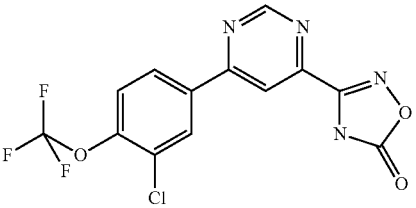 [SMILES: O=c1[nH]c(-c2cc(-c3ccc(OC(F)(F)F)c(Cl)c3)ncn2)no1] | 358.66 | [M + H]⁺ = 359, 100% @ rt = 4.43 min |
| 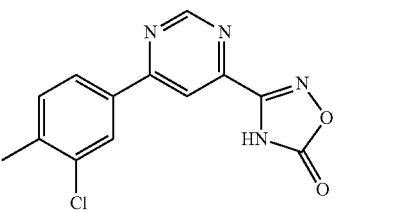 [SMILES: Cc1ccc(-c2cc(-c3noc(=O)[nH]3)ncn2)cc1Cl] | 288.69 | [M + H]⁺ = 289/291, 100% @ rt = 4.16 min |
| 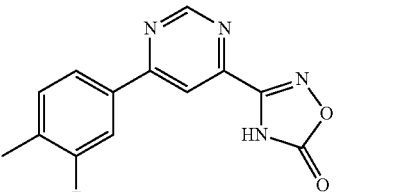 | 272.24 | [M + H]⁺ = 273, 100% @ rt = 4.03 min |
| 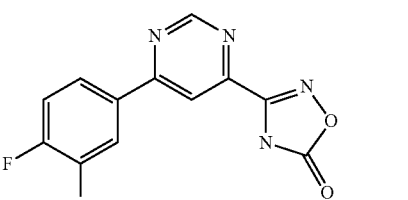 | 292.66 | [M + H]⁺ = 293/295, 100% @ rt = 4.13 min |
| 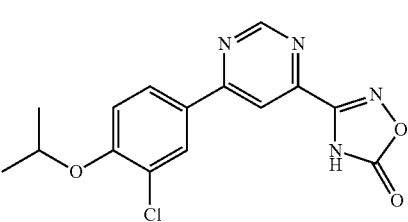 [SMILES: CC(C)Oc1ccc(-c2cc(-c3noc(=O)[nH]3)ncn2)cc1Cl] | 332.75 | [M + H]⁺ = 333/335, 100% @ rt = 4.49 min |
| 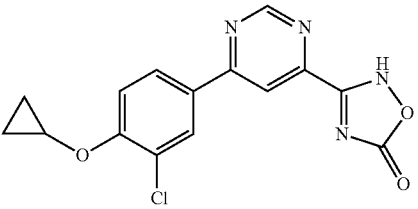 [SMILES: O=c1nc(-c2cc(-c3ccc(OC4CC4)c(Cl)c3)ncn2)[nH]o1] | 330.726 | [M + H]+ = 331/333, 100% @ rt = 4.30 min |

Example 7

Reaction Scheme 7

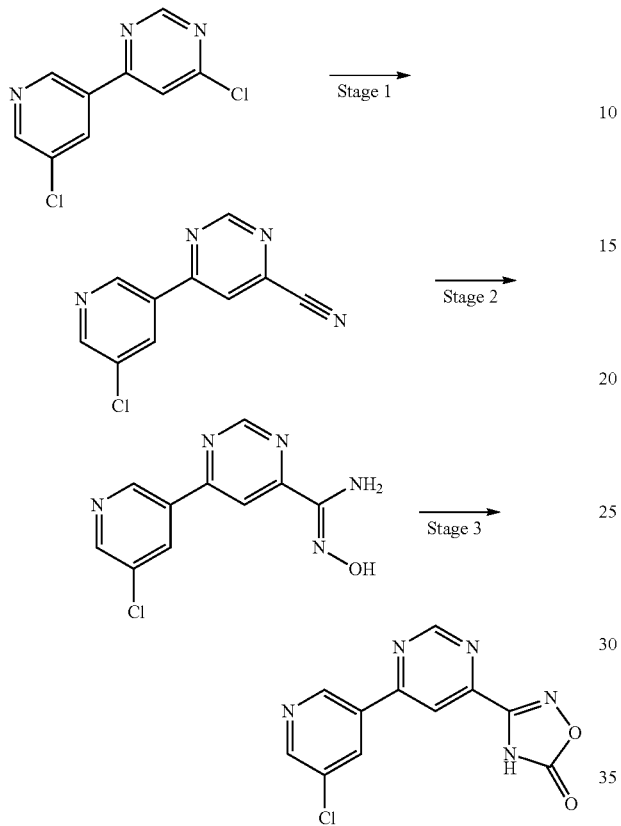

Referring to Reaction Scheme 7, Stage 1, to a solution of 4-chloro-6-(5-chloro-pyridin-3-yl)-pyrimidine (1 eq) in degassed DMF (20 vol) was added Pd(PPh3)4 (0.05 eq) followed by zinc cyanide (1 eq). The reaction mixture was heated at 100° C. until completion of the reaction by LCMS whereupon it was cooled to room temperature. Water (37.5 vol) was added to the reaction mixture, which was extracted with EtOAc (150 vol). The organic layer was washed with water (1000 vol), followed by saturated aqueous NaCl solution (200 vol), dried over MgSO4, filtered and concentrated in vacuo. Purification by flash column chromatography (eluent: EtOAc:heptane) afforded the target compound.

Referring to Reaction Scheme 7, Stage 2, to a stirred solution of 6-(5-chloro-pyridin-3-yl)-pyrimidine-4-carbonitrile (1 eq) in ethanol (25 vol) was added hydroxylamine hydrochloride (1.05 eq), followed by diisopropylethylamine (1.05 eq). The reaction mixture was heated at 70° C. with stirring for 1 hour. It was allowed to cool to room temperature and diluted with EtOAc (750 vol). The organic layer was washed with water (2500 vol) and with a saturated aqueous NaCl solution (2500 vol), dried with MgSO4, filtered and the solvent removed in vacuo to give the desired intermediate as a yellow powder, which was used without any further purification in the next stage.

Referring to Reaction Scheme 7, Stage 3, to a stirred solution of 6-(5-chloro-pyridin-3-yl)-N-hydroxy-pyrimidine-4-carboxamidine (1 eq) in 1,4-dioxane (16 vol) was added 1,1'-carbonyldiimidazole (1.24 eq), 1,8-diazabicyclo[5.4.0]undec-7-ene (1.07 eq) and the reaction mixture was stirred at 110° C. for 5 hours. The flask was recharged 3 times with 1,1'-carbonyldiimidazole (0.24 eq), 1,8-diazabicyclo[5.4.0]undec-7-ene (0.07 eq) and the reaction monitored by LCMS until it reached completion. The reaction was allowed to cool to room temperature and the solvent removed in vacuo. The resulting residue was dissolved in water and EtOAc. The aqueous layer was isolated and washed with EtOAc (3×). It was then acidified to pH1 with a 2M HCl solution and extracted with EtOAc (3×). The organic phases were combined and washed with a saturated aqueous NaCl solution (50 vol), dried over MgSO4, filtered and concentrated in vacuo to furnish the desired target compound.

The following compounds were prepared substantially as described above.

| Structure | Molecular Weight | Mass Spec Result |
|---|---|---|
| (structure shown) | 275.66 | $[M + H]^+$ = 275, 100% @ rt = 3.41 min |

Example 8

Reaction Scheme 8

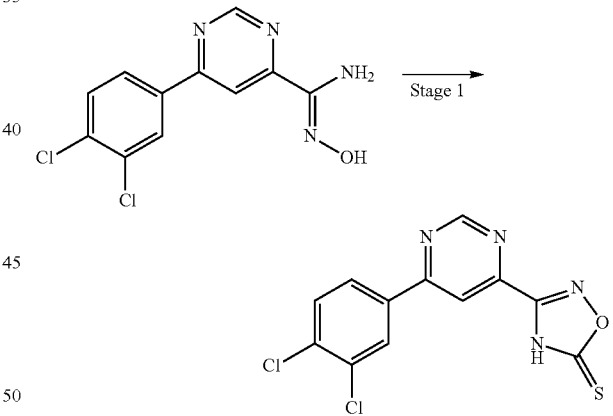

Referring to Reaction Scheme 8, Stage 1, to a stirred solution of N-hydroxy-6-(3,4-dichloro-phenyl)-pyrimidine-4-carboxamidine (1 eq) in acetonitrile (25 vol) was added 1,1'-thiocarbonyldiimidazole (1.5 eq), 1,8-diazabicyclo[5.4.0]undec-7-ene (4 eq) and the reaction mixture was stirred at ambient for 2 hours. The solvent was removed in vacuo and the resulting residue was triturated with a 2M HCl solution. The intermediate was collected by filtration, dried under air suction and suspended in THF (18 vol). Boron trifluoride-diethyl etherate (5 eq) was added to the previous suspension, which was stirred at ambient temperature for 16 hours. The solvent was removed in vacuo and the resulting residue was triturated with water and filtered. The desired target compound was further purified by passing it through a short pad of resin MP-TsOH(65) (3.37 mmol/g) eluting with methanol.

The following compounds were prepared substantially as described above.

| Structure | Molecular Weight | Mass Spec Result |
|---|---|---|
| 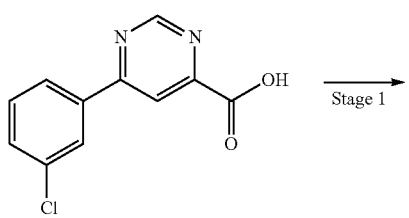 | 325.18 | $[M + H]^+$ = 324, 94% @ rt = 4.96 min |

Example 9

Reaction Scheme 9

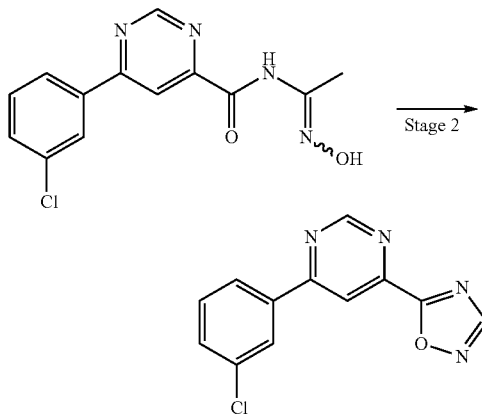

Referring to Reaction Scheme 9, Stage 1, to a stirred solution of 6-(3-chloro-phenyl)-pyrimidine-4-carboxylic acid (1 eq) in DMF (6 vol) was added EDC (1.5 eq), HOBt (1.1) and the reaction mixture was stirred at ambient temperature for 1 hour. Acetamide oxime (1.2 eq) was added to the reaction mixture, which was stirred at ambient temperature for 16 hours. The reaction mixture was poured into water, provoking the formation of a precipitate, which was collected by filtration. Purification by flash column chromatography (eluent: EtOAc) afforded the required intermediate.

Referring to Reaction Scheme 9, Stage 1, to a stirred solution of 6-(3-chloro-phenyl)-pyrimidine-4-carboxylic acid [1-(hydroxyimino)-ethyl]-amide (1 eq) in DCM (130 vol) was added potassium tert-butoxide (6 eq) and the reaction mixture was stirred at ambient temperature for 1.5 hours. Water (170 vol) was added to the reaction mixture and the aqueous phase was separated and extracted with DCM (2×). The organic layers were combined, dried with Na2SO4, filtered and the solvent removed in vacuo to furnish the desired target compound, which was purified by prep HPLC.

The following compounds were prepared substantially as described above.

| Structure | Molecular Weight | Mass Spec Result |
|---|---|---|
| 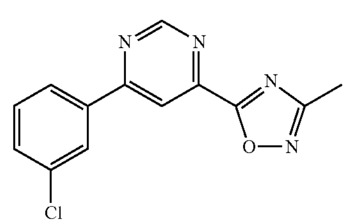 [SMILES: Cc1noc(-c2cc(-c3cccc(Cl)c3)ncn2)n1] | 272.7 | $[M + H]^+$ = 273, 100% @ rt = 4.30 min |

Example 10

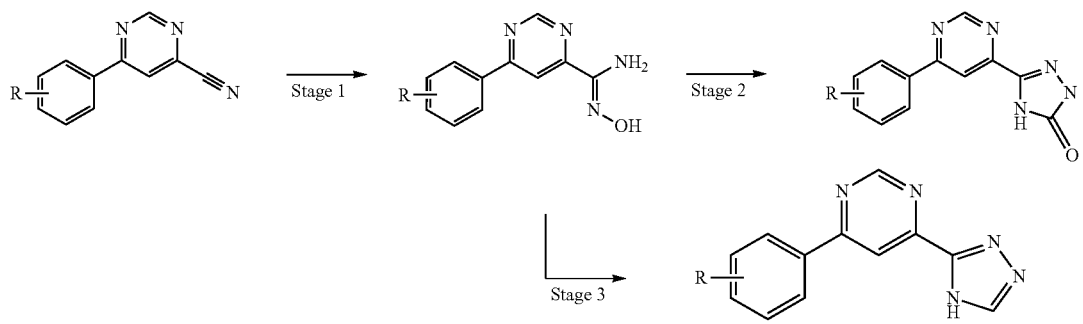

Referring to Reaction Scheme 10, Stage 1, to a stirred solution of 6-(substituted-phenyl)-pyrimidine-4-carbonitrile (1 eq) in ethanol (10 vol) was added hydrazine monohydrate (2 eq) and the reaction mixture was heated at 100° C. with stirring for 2 hours. The reaction mixture was allowed to cool to room temperature and the precipitate thus formed was filtered and washed with methanol to give an off-white solid, which was used in the next stage without further purification.

Referring to Reaction Scheme 10, Stage 2, to a stirred solution of the intermediate obtained in Stage 1 (1 eq) in 1,4-dioxane (16 vol) was added 1,1'-carbonyldiimidazole (1.24 eq) followed by 1,8-diazabicyclo[5.4.0]undec-7-ene (1.07 eq) and the reaction mixture was stirred at 100° C. for 2 hours. 1,1'-Carbonyldiimidazole (0.5 eq) and 1,8-diazabicyclo[5.4.0]undec-7-ene (0.2 eq). were added to the reaction mixture, which was stirred at 100° C. for a further 2 hours. The solvent was removed in vacuo. The resulting solid was triturated with EtOAc and water. It was filtered and washed with DCM, EtOAc, DCM/Methanol, then DCM to furnish the desired compound, which was dried in a vacuum oven.

Referring to Reaction Scheme 10, Stage 3, formic acid (10 vol) was added to the intermediate obtained in Stage 1 and the reaction mixture was heated at 100° C. with stirring for 48 hours. Molecular sieves and formic acid (10 vol) were added to the reaction mixture, which was heated at 120° C. for 16 hours. The reaction mixture was allowed to cool to room temperature, filtered and the solvent was removed in vacuo. The resulting solid was washed with a saturated aqueous NaHCO$_3$ solution, water and methanol to furnish the desired target molecule.

The following compounds were prepared substantially as described above.

| Structure | Molecular Weight | Mass Spec Result NMR Result |
|---|---|---|
| 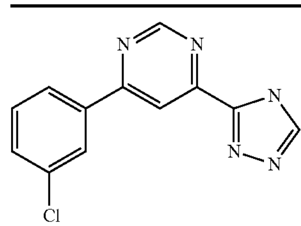 | 257.68 | [M + H]$^+$ = 257, 99% @ rt = 3.61 min |
| 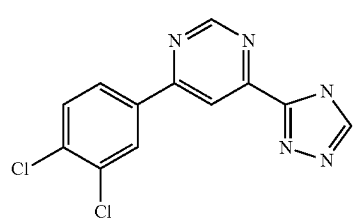 [SMILES: Clc1ccc(-c2cc(-c3nnc[nH]3)ncn2)cc1Cl] | 292.13 | [M + H]$^+$ = 291, 98% @ rt = 3.92 min |
| 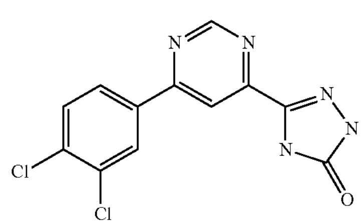 [SMILES: O=c1[nH]nc(-c2cc(-c3ccc(Cl)c(Cl)c3)ncn2)[nH]1] | 308.13 | very unsoluble compound-LCMS unobtainable $^1$H NMR (250 MHz, DMSO-d6) ppm 9.27-9.32 (1 H, m), 8.39-8.47 (2 H, m), 8.17-8.25 (1 H, m), 7.76-7.85 (1 H, m) |

Example 11

Reaction Scheme 11

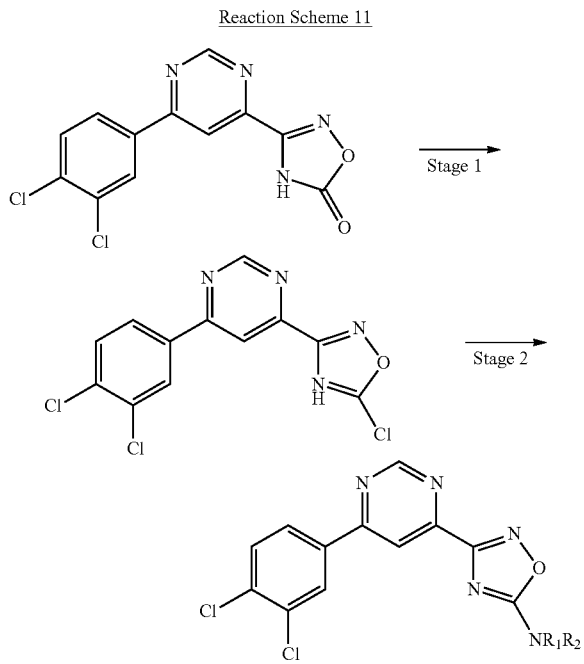

Referring to Reaction Scheme 11, Stage 1, to a stirred solution of 3-[6-(3,4-dichloro-phenyl)-pyrimidin-4-yl]-4H-[1,2,4]oxadiazol-5-one (1 eq) in phosphorus oxychloride (8 vol) was added pyridine (1 eq) and the reaction mixture was stirred at 80° C. for 16 hours. The reaction was cooled to 0° C. and poured onto ice. The aqueous phase was extracted with EtOAc. The organic phase was then washed with water and with a saturated aqueous NaCl solution, dried with MgSO4, filtered and the solvent removed in vacuo to furnish the expected intermediate, which was used without further purification in the next stage.

Referring to Reaction Scheme 11, Stage 2, to a stirred solution of the previous intermediate (1 eq) in DMF (14 vol) was added triethylamine (2.5 eq) followed by the appropriate amine (1 eq to 5 eq) and the reaction mixture was stirred at ambient temperature and monitored by LCMS until completion. The resulting precipitate was collected by filtration and washed with water. Purification by flash column chromatography (eluent: [1:9 to 1:1] EtOAc:heptane) afforded the required target compound.

The following compounds were prepared substantially as described above.

| Structure | Molecular Weight | Mass Spec Result |
|---|---|---|
| 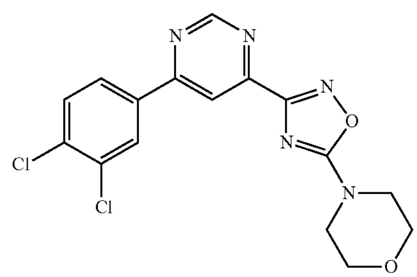 [SMILES: Clc1ccc(-c2cc(-c3noc(N4CCOCC4)n3)ncn2)cc1Cl] | 378.22 | $[M + H]^+$ = 377, 100% @ rt = 4.81 min |
| 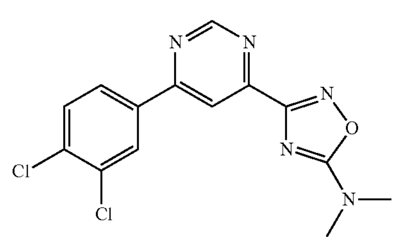 [SMILES: CN(C)c1nc(-c2cc(-c3ccc(Cl)c(Cl)c3)ncn2)no1] | 336.18 | $[M + H]^+$ = 335, 99% @ rt = 4.84 min |

Example 12

Reaction Scheme 12

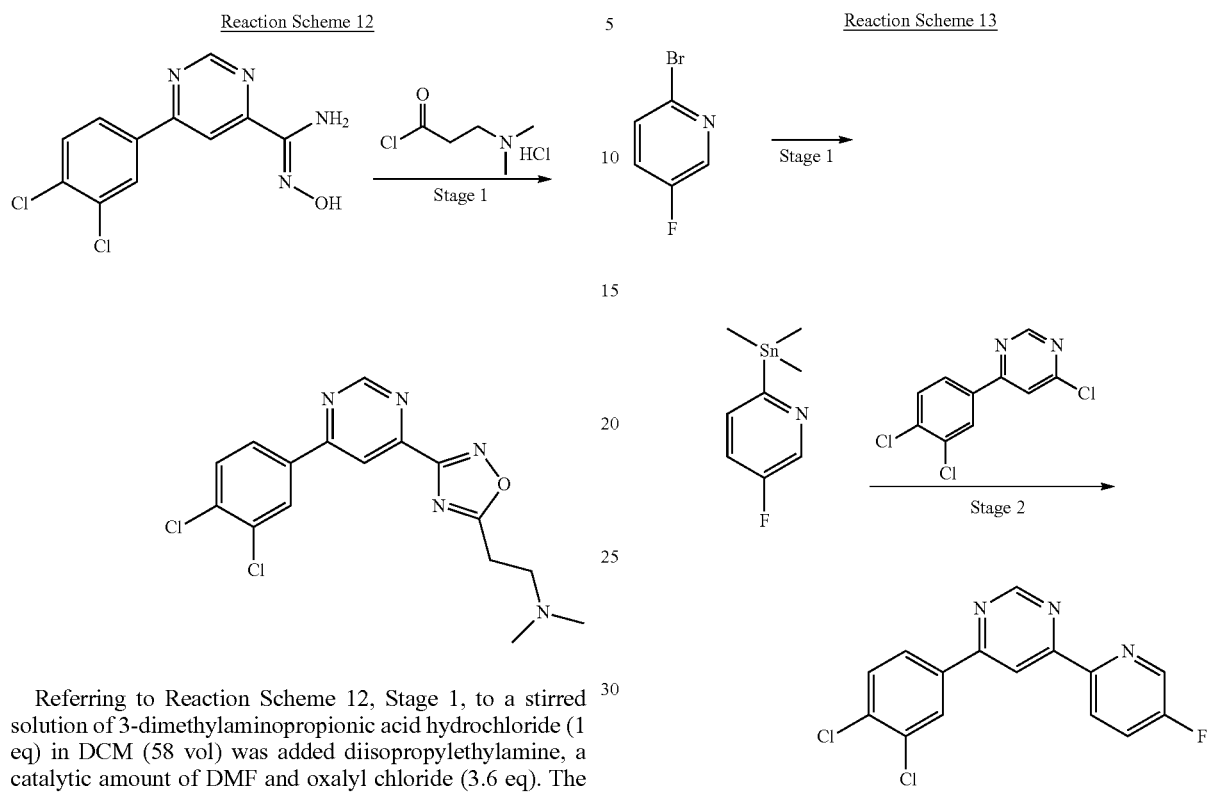

Referring to Reaction Scheme 12, Stage 1, to a stirred solution of 3-dimethylaminopropionic acid hydrochloride (1 eq) in DCM (58 vol) was added diisopropylethylamine, a catalytic amount of DMF and oxalyl chloride (3.6 eq). The reaction mixture was stirred at ambient temperature for 1 hour and the solvents removed in vacuo. The resulting residue was dissolved in DCM (25 vol) and added to a stirred solution of 6-(3,4-dichloro-phenyl)-N-hydroxy-pyrimidine-4-carboxamidine and diisopropylethylamine (1.2 eq) in DCM (33 vol). Sodium hydride (1.2 eq) was added to the reaction mixture, which was stirred at ambient temperature for 4 hours. The solvent was removed in vacuo and the resulting residue was dissolved in EtOAc, washed with water (2×) and EtOAc was removed in vacuo. Purification by flash column chromatography (eluent: [0:1 to 5:95] methanol:EtOAc) afforded the required target compound.

The following compounds were prepared substantially as described above.

Example 13

Reaction Scheme 13

Referring to Reaction Scheme 13, Stage 1, to a stirred solution of 2-bromo-5-fluoro-pyridine (1 eq) and hexamethylditin (1 eq) in degassed 1,2-dimethoxyethane (125 vol) was added $Pd(PPh_3)_4$ (0.05 eq). The reaction mixture was stirred at 80° C. for 16 hours and allowed to cool to room temperature. The resulting solution was used without further purification in the next stage.

Referring to Reaction Scheme 13, Stage 2, 4-chloro-6-(3,4-dichlorophenyl)-pyrimidine (1 eq) and $Pd(PPh_3)_4$ (0.05 eq) were added to the previous solution containing 5-fluoro-2-trimethylstannanyl-pyridine (1.5 eq) and the reaction mixture was heated to reflux for 16 hours. It was allowed to cool to room temperature and diluted with EtOAc. The organic layer was washed with water, dried with $Na_2SO_4$, filtered and the solvent removed in vacuo. The resulting residue was triturated with EtOAc and DCM to afford the desired compound.

The following compounds were prepared substantially as described above.

| Structure | Molecular Weight | Mass Spec Result |
|---|---|---|
| 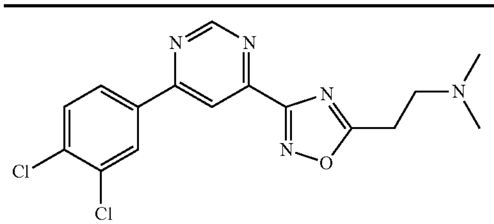 | 364.24 | $[M + H]^+$ = 365, 98% @ rt = 3.44 min |

| Structure | Molecular Weight | Mass Spec Result |
|---|---|---|
| (structure: 4-(3,4-dichlorophenyl)-6-(5-fluoropyridin-2-yl)pyrimidine) | 320.16 | [M + H]$^+$ = 319, 100% @ rt = 5.41 min |

Example 14

Reaction Scheme 14

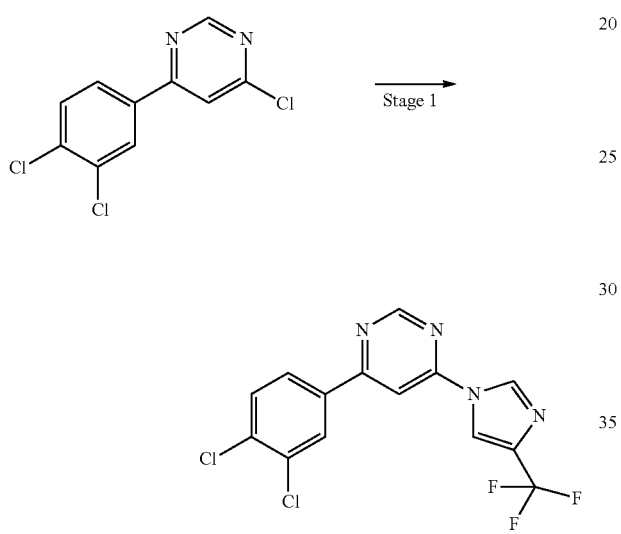

Referring to Reaction Scheme 14, Stage 1, a solution of 4-chloro-6-(3,4-dichloro-phenyl)-pyrimidine (1 eq), 4-(trifluoromethyl)-1H-imidazole (2 eq) and potassium carbonate (1.1 eq) in tert-butanol (10 vol) was heated at 150° C. in a microwave for 25 minutes. Potassium carbonate (1.1 eq) was added to the reaction mixture, which was heated at 160° C. in a microwave for 35 minutes. Water was added and the desired material was extracted with EtOAc. The organic phase was dried with MgSO$_4$, filtered and evaporated to dryness. Purification by flash column chromatography (eluent: [99.5:0.5] DCM:MeOH) afforded the target compound.

The following compounds were prepared substantially as described above.

| Structure | Molecular Weight | Mass Spec Result |
|---|---|---|
| (structure: 4-(3,4-dichlorophenyl)-6-(4-(trifluoromethyl)-1H-imidazol-1-yl)pyrimidine) | 359.14 | [M + H]$^+$ = 359/361, 98% @ rt = 5.04 min |

Example 15

Reaction Scheme 15

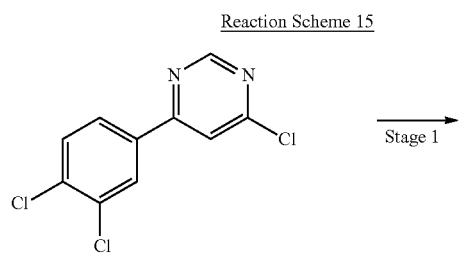

to dryness. Purification by flash column chromatography and trituration using an adequate solvent afforded the target compound.

Referring to Reaction Scheme 15, Stage 2, to a solution of 1-[6-(3,4-dichloro-phenyl)-pyrimidin-4-yl]-1,3-dihydro-imidazol-2-one in DMF (30 vol) was added sodium hydride (1 eq) at 5° C. and the reaction mixture was stirred for 15 minutes. Methyl iodide (2 eq) was added to the reaction mixture, which was stirred at room temperature for 3 hours and at 40° C. for 30 minutes. The reaction mixture was poured into water and extracted with EtOAc, dried with $Na_2SO_4$, filtered and evaporated to dryness. Purification by flash column chromatography (eluent: [1:2] EtOAc:heptane) afforded the target compound.

The following compounds were prepared substantially as described above.

| Structure | Molecular Weight | Mass Spec Result |
|---|---|---|
| 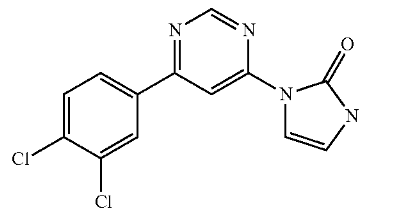 [SMILES: O=c1[nH]ccn1-c1cc(-c2ccc(Cl)c(Cl)c2)ncn1] | 307.14 | $[M + H]^+ = 307/309$, 99% @ rt = 4.26 min |
| 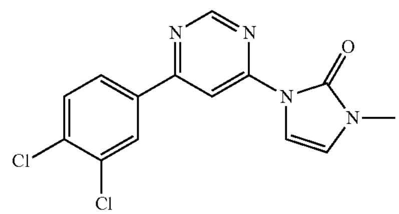 [SMILES: Cn1ccn(-c2cc(-c3ccc(Cl)c(Cl)c3)ncn2)c1=O] | 321.17 | $[M + H]^+ = 321/323$, 99% @ rt = 4.56 min |

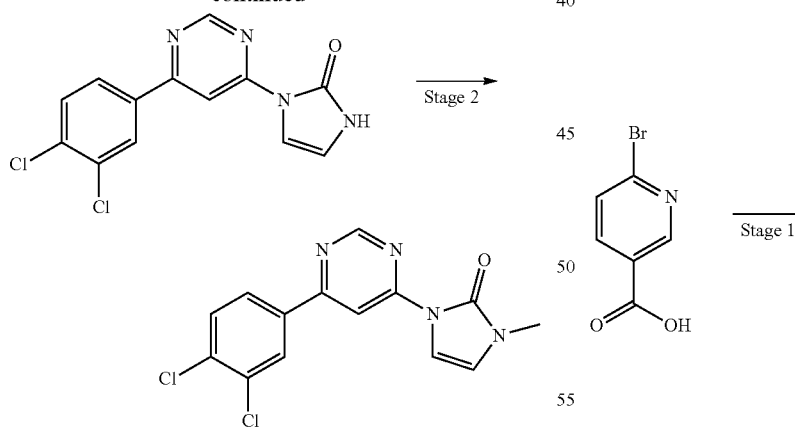

-continued

Referring to Reaction Scheme 15, Stage 1, to a solution of 4-chloro-6-(3,4-dichloro-phenyl)-pyrimidine (1 eq) in DMF (20 vol) was added sodium hydride (1.5 eq) and imidazolone (1.5 eq). The reaction mixture was heated at 90° C. in a microwave for 5 minutes. To the cool mixture were added dichloromethane and a saturated solution of $NaHCO_3$. The organic layer was separated and the aqueous layer was extracted further with dichloromethane. The organic layers were combined, dried with $Na_2SO_4$, filtered and evaporated

Example 16

Reaction Scheme 16

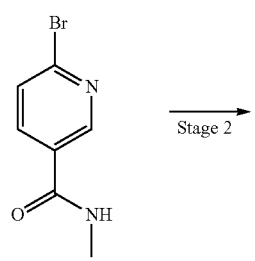

Example 17

Reaction Scheme 17

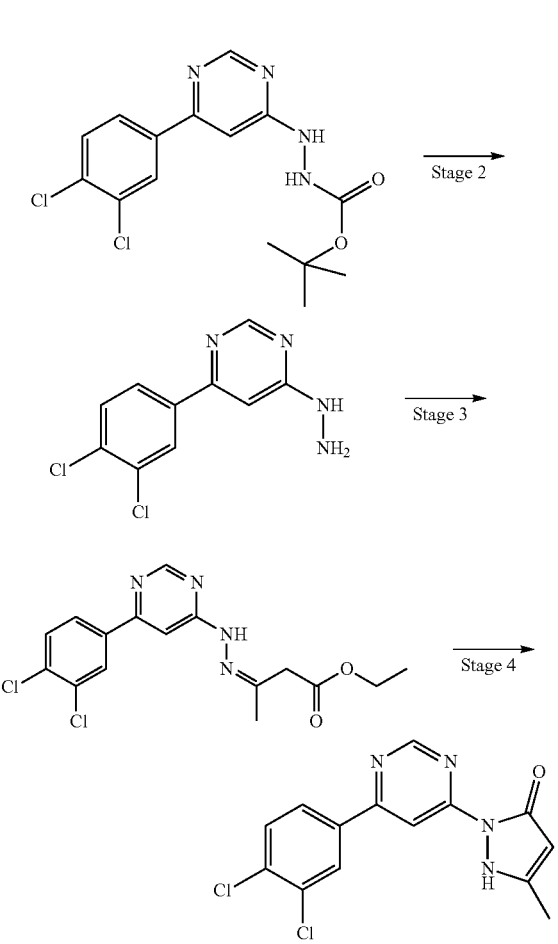

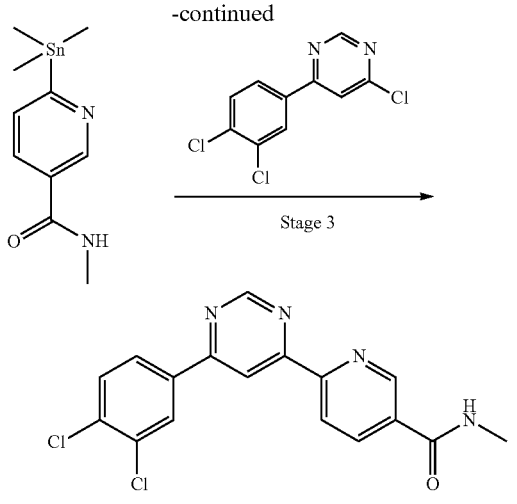

Referring to Reaction Scheme 16, Stage 1, 6-bromo-nicotinic acid (1 eq), HOBt (1.4 eq) and HATU (1.3 eq) were dissolved in DMF (25 vol) and the reaction mixture was stirred 1 hour at ambient temperature. Methylamine hydrochloride (1.5 eq) and triethylamine (1.1 eq) were added and the reaction mixture was stirred 16 hours at ambient temperature. DMF was removed in vacuo and water and EtOAc were added to the residue. The organic phase was separated and washed with a saturated aqueous solution of $NaHCO_3$, dried with $MgSO_4$, filtered and the solvent removed in vacuo. The residue was triturated with EtOAc/heptane (1/1) to furnish the desired intermediate.

Referring to Reaction Scheme 16, Stage 2, to a stirred solution of 6-bromo-N-methyl-nicotinamide (1 eq) and hexamethylditin (1 eq) in degassed 1,2-dimethoxyethane (125 vol) was added $Pd(PPh_3)_4$ (0.05 eq). The reaction mixture was stirred at 80° C. for 16 hours and allowed to cool to room temperature. The resulting solution was used without further purification in the next stage.

Referring to Reaction Scheme 16, Stage 3, 4-chloro-6-(3,4-dichlorophenyl)-pyrimidine (1 eq) and $Pd(PPh_3)_4$ (0.05 eq) were added to the previous solution containing N-methyl-6-trimethylstannanyl-nicotinamide (1.5 eq) and the reaction mixture was heated to reflux for 16 hours. It was allowed to cool to room temperature and diluted with EtOAc. The organic layer was washed with water, dried with $Na_2SO_4$, filtered and the solvent removed in vacuo. Purification by flash column chromatography (eluent: [2:1] EtOAc:heptane) afforded the target compound.

The following compounds were prepared substantially as described above.

| Structure | Molecular Weight | Mass Spec Result |
|---|---|---|
| 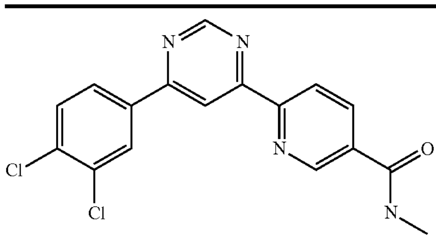 | 359.22 | $[M + H]^+$ = 359/361, 100% @ rt = 4.48 min |

Referring to Reaction Scheme 17, Stage 1, 4-chloro-6-(3,4-dichloro-phenyl)-pyrimidine (1 eq) and tert-butyl carbazate (2.1 eq) were dissolved in 1,4-dioxane (10 vol). The reaction mixture was stirred and heated at reflux under an atmosphere of nitrogen for 6 hours. The reaction mixture was evaporated in vacuo, treated with a saturated aqueous solution of NaHCO$_3$ and filtered to furnish the desired intermediate, which was dried in vacuo.

Referring to Reaction Scheme 17, Stage 2, N'-[6-(3,4-dichloro-phenyl)-pyrimidin-4-yl]-hydrazinecarboxylic acid tert-butyl ester (1 eq) was dissolved in MeOH (120 vol) and treated with 4M HCl in 1,4-dioxane (100 vol) and kept at room temperature for 4 hours while stirring. The reaction mixture was filtered and the precipitate was dissolved in hot water. A saturated aqueous solution of NaHCO$_3$ was added to the aqueous solution and the reaction mixture was stirred for 1 hour while cooling to room temperature. The precipitate was filtered off and dried in vacuo to give the desired intermediate.

Referring to Reaction Scheme 17, Stage 3, a mixture of [6-(3,4-dichloro-phenyl)-pyrimidin-4-yl]-hydrazine (1 eq), ethyl acetoacetate (1.2 eq) and ethanol (100 vol) was heated to reflux for 2 hours. The reaction mixture was evaporated in vacuo and the residue was triturated with hexane to furnish the desired intermediate, which was used in the next step without further purification.

Referring to Reaction Scheme 17, Stage 4, 3-{[6-(3,4-dichloro-phenyl)-pyrimidin-4-yl]-hydrazono}-butyric acid ethyl ester (1 eq) was stirred in a solution of sodium hydroxide (2M, 1.1 eq) at ambient temperature for 45 minutes and then refluxed with stirring for 45 minutes. To the cooled reaction mixture acetic acid was added followed by ethanol (1 mL) and the reaction mixture was stirred vigorously at ambient temperature. The precipitate was filtered and washed with ethanol and water to furnish the desired compound, which was dried in vacuo.

The following compounds were prepared substantially as described above.

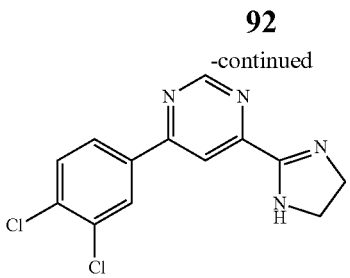

Stage 2

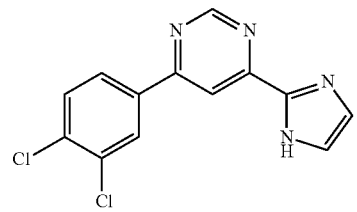 [SMILES: Clc1ccc(-c2cc(-c3ncc[nH]3)ncn2)cc1Cl]

Referring to Reaction Scheme 18, Stage 1, to a solution of 6-(3,4-dichloro-phenyl)-pyrimidine-4-carbonitrile (1 eq) and ethylene-1,2-diamine (1 eq) in toluene (12 vol) was added phosphorus pentasulfide. The reaction mixture was stirred and heated at reflux for 3.5 hours. The reaction mixture was poured into water and extracted with DCM (×3). The organic layers were combined and washed with a saturated aqueous solution of NaCl, dried with Na$_2$SO$_4$, filtered and the solvent removed in vacuo. Purification by flash column chromatography (eluent: [1:1] to [1:0] EtOAc:heptane) afforded the target compound.

| Structure | Molecular Weight | Mass Spec Result |
|---|---|---|
| 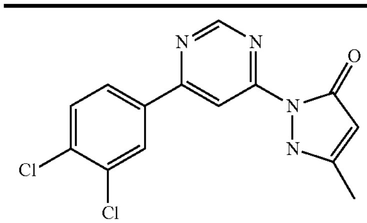 | 321.17 | [M + H]$^+$ = 321, 100% @ rt = 4.32 min |

Example 18

Reaction Scheme 18

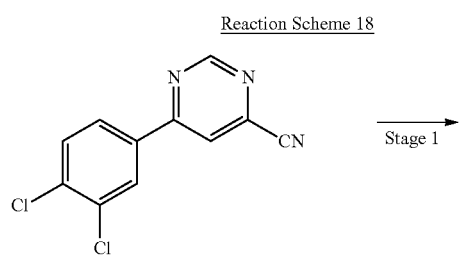

Stage 1

Referring to Reaction Scheme 18, Stage 2, to a suspension of 4-(3,4-dichloro-phenyl)-6-(4,5-dihydro-1H-imidazol-2-yl)-pyrimidine (1 eq) in acetonitrile (40 vol) was added permanganate potassium (2.5 eq) and silica gel (8.5 eq). The reaction mixture was stirred at room temperature for 3 hours. The reaction mixture was poured into water and extracted with DCM (2×). The organic layers were combined and evaporated to dryness in vacuo. Purification by flash column chromatography (eluent: [99:1] DCM:MeOH) followed by SCX column (eluent: [100:0] to [80:20] MeOH: 0.880 ammonia) afforded the target compound.

The following compounds were prepared substantially as described above.

| Structure | Molecular Weight | Mass Spec Result |
|---|---|---|
| 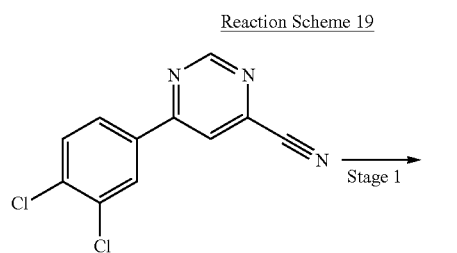 (top structure) | 293.16 | [M + H]⁺ = 294, 100% @ rt = 2.85 min |
| (bottom structure) | 291.14 | [M + H]⁺ = 292, 99% @ rt = 3.64 min |

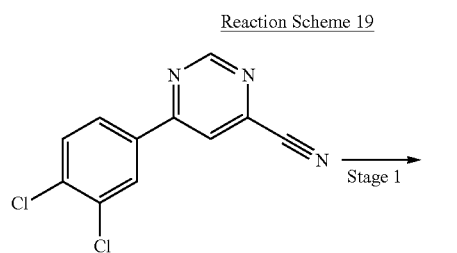

Example 19

Reaction Scheme 19

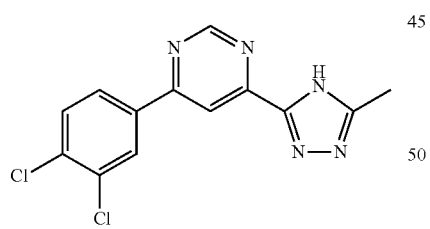

Referring to Reaction Scheme 19, Stage 1, to a stirred suspension of acetic hydrazide (1.2 eq) in anhydrous toluene (30 vol) was added triethylaluminium (1M in hexanes, 2.5 eq) at 0° C. The reaction mixture was stirred at ambient temperature for 40 minutes under an atmosphere of nitrogen. 6-(3,4-dichloro-phenyl)-pyrimidine-4-carbonitrile (1 eq) was added to the previous reaction mixture, which was stirred at 85° C. for 6 hours, then at 170° C. for 2 hours. The reaction mixture was then irradiated in the microwave at 180° C. for 30 minutes. The solvents were removed in vacuo and the residue was further purified by flash column chromatography (eluent [5:95] ammonia in MeOH:DCM) and trituration with acetonitrile/water (1/1) to afford the desired molecule.

The following compounds were prepared substantially as described above.

| Structure | Molecular Weight | Mass Spec Result |
|---|---|---|
| 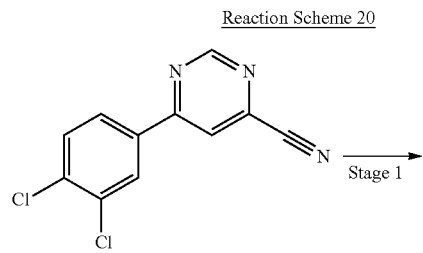 | 306.16 | [M + H]⁺ = 306/308, 98% @ rt = 4.02 min |

Example 20

Reaction Scheme 20

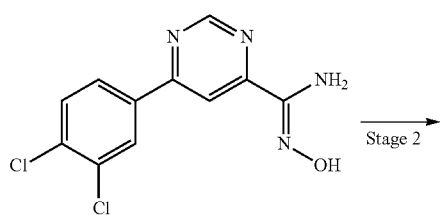

-continued

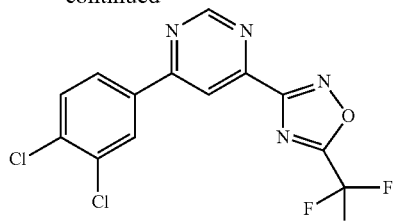

Referring to Reaction Scheme 20, Stage 1, to a stirred solution of 6-(3,4-dichloro-phenyl)-pyrimidine-4-carbonitrile (1 eq) in ethanol (25 vol) was added hydroxylamine hydrochloride (1.05 eq), followed by diisopropylethylamine (1.05 eq). The reaction mixture was heated at 70° C. for 1 hour. It was allowed to cool to room temperature and diluted with water (60 vol). The precipitate was filtered off and washed with water to furnish the desired intermediate, which was used without any further purification in the next stage.

Referring to Reaction Scheme 20, Stage 2, to a stirred solution of N-hydroxy-6-(3,4-dichloro-phenyl)-pyrimidine-4-carboxamidine (1 eq) in DCM (25 vol) was added trifluoroacetic anhydride (8 eq) and the reaction mixture was stirred at room temperature for 2 hours after which time diisopropylethylamine (2 eq) was added. The reaction mixture was partitioned between DCM and a 1M aqueous solution Na$_2$CO$_3$ and the organic layer was collected, dried with Na$_2$SO$_4$, filtered and the solvent removed in vacuo. Purification by flash column chromatography (eluent: [1:9] EtOAc: heptane) followed by recrystallisation from ethanol afforded the target compound.

The following compounds were prepared substantially as described above.

| Structure | Molecular Weight | Mass Spec Result |
|---|---|---|
| 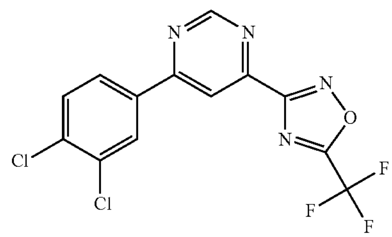 [SMILES: FC(F)(F)c1nc(-c2cc(-c3ccc(Cl)c(Cl)c3)ncn2)no1] | 361.11 | [M + H]$^+$ = 361/363, 100% @ rt = 5.28 min |

Example 21

Reaction Scheme 21

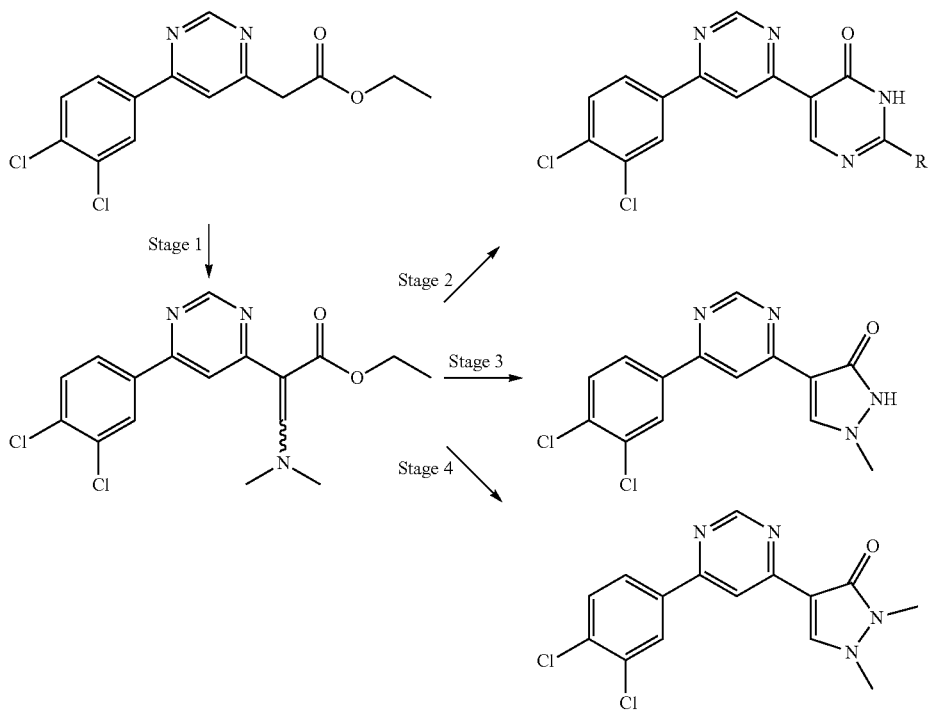

Referring to Reaction Scheme 21, Stage 1, a mixture of [6-(3,4-dichloro-phenyl)-pyrimidin-4-yl]-acetic acid ethyl ester (1 eq) and dimethylformamide dimethyl acetal (20 vol) was stirred at reflux under nitrogen for 8 h. When cool, the solution was evaporated and the residue purified by flash chromatography on a silica gel cartridge. Elution with ethyl acetate afforded impurities followed by the product (89% yield) as a beige solid.

Referring to Reaction Scheme 21, Stage 2, a mixture of 2-[6-(3,4-dichloro-phenyl)-pyrimidin-4-yl]-3-dimethylamino-acrylic acid ethyl ester (1 eq), DMF (20 vol), and formamidine acetate (4 eq) was stirred at 100° C. for 16 hours in a sealed tube flushed with nitrogen. The mixture was evaporated in vacuo, treated with aqueous saturated sodium bicarbonate (100 vol) and extracted with ethyl acetate (4000 vol, then 1000 vol). The combined, dried (Na₂SO₄) organic extracts were evaporated in vacuo. The residue was dissolved in hot methanol and absorbed onto silica gel (20 vol). This was applied to an Isolute silica gel cartridge, and eluted with dichloromethane-ethanol (100:0, then 98:2, then 95:5, then 93:7) to give an impurity followed by the product as an off-white solid (41% yield).

In a similar reaction in which guanidine carbonate was used (replacing formamidine acetate), the work-up procedure was as follows:

Water (140 vol) was added, the precipitate collected, and washed consecutively with water (280 vol), heptane, ether, and dried in vacuo. The product was washed with acetonitrile/water to remove DMF. The resultant solid was stirred in methanol, the supernatant discarded, and this repeated five times. The resultant solid was stirred in acetonitrile, the supernatant discarded, and this repeated three times. The solid was suspended in acetonitrile, evaporated in a Genevac at 40° C., then dried overnight in vacuo at 40° C. to give the product.

Referring to Reaction Scheme 21, Stage 3, a mixture of 2-[6-(3,4-dichloro-phenyl)-pyrimidin-4-yl]-3-dimethylamino-acrylic acid ethyl ester (1 eq) in dioxane (10 vol) was treated with methylhydrazine (1 eq) and heated at 80° C. for 14 hours in a sealed tube with stirring under nitrogen. When cool, the precipitate was filtered off, washed with dioxane (40 vol) and dried in vacuo. The precipitate was treated with methanol (200 vol) and stirred at reflux for 20 minutes. When cool, the precipitate was filtered off and dried in vacuo to give the product as an orange powder (47% yield).

Referring to Reaction Scheme 21, Stage 4, a mixture of 2-[6-(3,4-dichloro-phenyl)-pyrimidin-4-yl]-3-dimethylamino-acrylic acid ethyl ester (1 eq), N,N'-dimethylhydrazine dihydrochloride (1 eq), and dioxane (25 vol) was stirred at room temperature under nitrogen whilst N,N-diisopropylethylamine (2.5 eq) was added dropwise. The stirred mixture was heated at 80° C. for 16 hours. When cool, the mixture was evaporated in vacuo and then adsorbed from hot methanol onto silica gel (20 vol). The resultant silica gel was purified on an Isolute cartridge (silica gel) eluting with ethyl acetate-methanol (88:12 to 84:16) to give the product as a light beige solid (45% yield).

The following compounds were prepared substantially as described above.

| Structure | Molecular Weight | Mass Spec Result 1H NMR Result |
|---|---|---|
| (structure) | 319.15 | [M + H]⁺ = 319/321, 100% @ rt = 3.92 min |
| (structure) | 321.17 | Compound is insufficiently soluble in any acceptable solvent in order to obtain a meaningful LCMS 1H NMR (500 MHz, DMSO-d6) d ppm 8.88 (1 H, s), 8.44 (1 H, br. s.), 8.26 (1 H, br. s.), 8.19 (1 H, d), 8.06 (1 H, br. s.), 7.85 (1 H, d), 3.45 (3 H, s) |
| (structure) | 334.17 | [M + H]⁺ = 334/336, 100% @ rt = 3.70 min |
| (structure) | 335.2 | [M + H]⁺ = 335/337, 100% @ rt = 3.88 min |

Example 22

Reaction Scheme 22

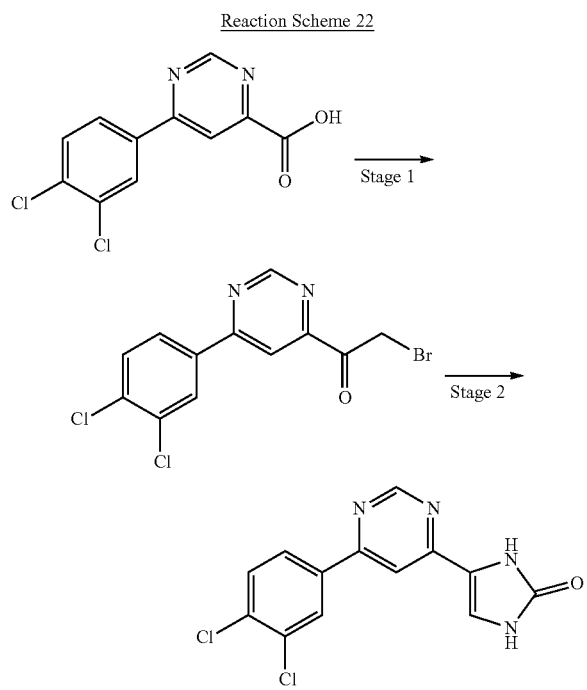

Referring to Reaction Scheme 22, Stage 1, a solution of 6-(3,4-dichloro-phenyl)-pyrimidine-4-carboxylic acid (1 eq) in dichloromethane (20 vol) was treated with DMF (catalytic amount), followed by the dropwise addition of oxalyl chloride (3 eq). After stirring for 2 hours, the mixture was evaporated in vacuo, treated with toluene (9 vol), and cooled to 0° C. Trimethylsilydiazomethane (5 eq) was added dropwise and stirring continued for 16 hours. 1,4-Dioxane (10 vol) was added at 0° C., followed by 48% hydrobromic acid (10 eq) in 1,4-dioxane (5 vol). After 1 hour, the pH was adjusted to 8-9 with aqueous saturated sodium bicarbonate, and the mixture twice extracted with ethyl acetate. The combined, dried (Na$_2$SO$_4$) organic extracts were evaporated and the residue purified on an Isolute cartridge (silica gel). Elution with ethyl acetate-heptane (1:10) gave a crude product which was crystallised from ethyl acetate-heptane. The resultant crystals were further purified by repeating the chromatography, whereupon the product crystallised out from the eluent (80% pure by NMR).

Referring to Reaction Scheme 22, Stage 2, acetic acid (3 eq) was added to a mixture of 2-bromo-1-[6-(3,4-dichloro-phenyl)-pyrimidin-4-yl]-ethanone (1 eq), urea (1 eq), ammonium acetate (3 eq), and this heated at reflux for 36 hours. Ethyl acetate and water were added, the organic layer separated, and the aqueous layer further extracted with ethyl acetate. The combined organic extracts were evaporated and the residue purified by silica gel chromatography, eluting with ethyl acetate, then dichloromethane-methanol (98:2, then 95:5, then 9:1) to give the product (5%).

The following compounds were prepared substantially as described above.

| Structure | Molecular Weight | Mass Spec Result |
|---|---|---|
| 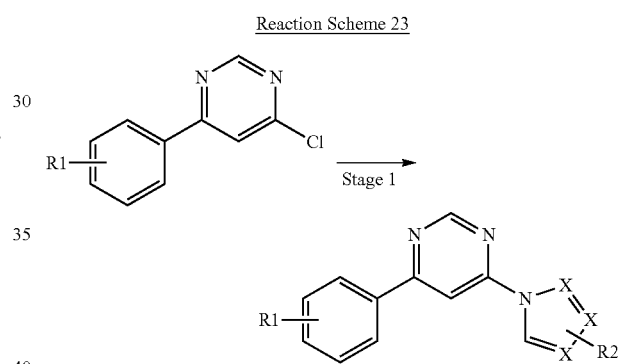 | 307.14 | [M + H]$^+$ = 307/309, 100% @ rt = 3.81 min |

Example 23

Reaction Scheme 23

Referring to Reaction Scheme 23, stage 1, a solution of 4-chloro-6-(substituted-phenyl)-pyrimidine (1 eq) and the appropriate amine (4 eq) in ethanol (10 vol) or tert-butanol (10 vol) was heated between 130° C. and 160° C. in a microwave for 40 to 60 minutes. In the case of 3-(trifluoromethyl) pyrazole, potassium carbonate (1.1 eq) was added to the reaction mixture prior heating. Acetonitrile/water (1/1) was added to the reaction mixture provoking the precipitation of the desired product, which was filtered and washed with acetonitrile/water (1/1) (3×) The product was dried under air suction and when necessary it was further purified by flash column chromatography (eluent: [1:3 to 0:1] heptane:DCM).

The following compounds were prepared substantially as described above.

| Structure | Molecular Weight | Mass Spec Result |
|---|---|---|
| 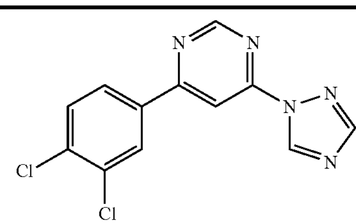 | 292.13 | [M + H]$^+$ = 291, 99% @ rt = 4.73 min |

-continued

| Structure | Molecular Weight | Mass Spec Result |
|---|---|---|
| 3-chlorophenyl-pyrimidine-triazole | 257.68 | [M + H]⁺ = 257, 99% @ rt = 4.32 min |
| 3,4-dichlorophenyl-pyrimidine-imidazole | 291.14 | [M + H]⁺ = 290, 100% @ rt = 4.18 min |
| 3,4-dichlorophenyl-pyrimidine-pyrazole | 291.14 | [M + H]⁺ = 290, 100% @ rt = 5.42 min |
| 3-chlorophenyl-pyrimidine-imidazole | 256.7 | [M + H]⁺ = 256, 99% @ rt = 3.72 min |
| 3-chlorophenyl-pyrimidine-pyrazole | 256.7 | [M + H]⁺ = 256, 96% @ rt = 4.86 min |
| 3,4-dichlorophenyl-pyrimidine-(trifluoromethyl)pyrazole | 359.14 | [M + H]⁺ = 360, 99% @ rt = 5.59 min |

Example 24

Reaction Scheme 24

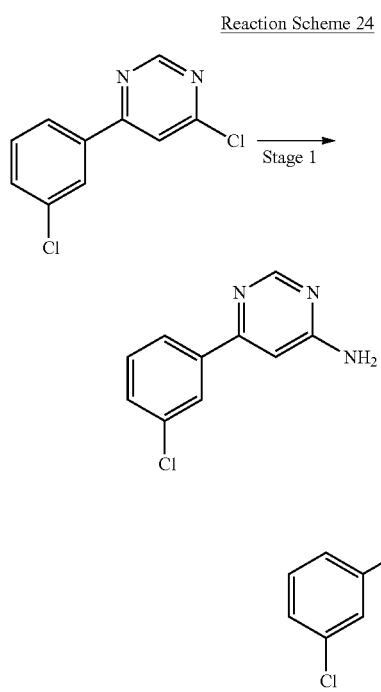

Referring to Reaction Scheme 24, stage 1, to a stirred suspension of 4-chloro-6-(3-chloro-phenyl)-pyrimidine (1 eq) in ethanol/1,4-dioxane (1/4) (5 vol) was added ammonium hydroxide solution (1 vol). The reaction mixture was heated in a sealed tube at 100° C. with stirring for 24 hours. Precipitation occurred upon cooling and the resulting solid was filtered off, washed with acetonitrile/water (1/1) (10 vol) to furnish the desired amine.

Referring to Reaction Scheme 24, stage 2, to a stirred suspension of 6-(3-chloro-phenyl)-pyrimidin-4-ylamine (1 eq) in acetic acid (4 vol) was added triethylorthoformate (4.6 eq) followed by sodium azide (1.2 eq). The reaction mixture was heated at reflux for 2.5 hours with stirring and was the allowed to cool to room temperature. The solvent was removed in vacuo and the resulting residue was triturated with acetonitrile/water (3/1), filtered and dried under air suction to afford the desired target compound.

The following compounds were prepared substantially as described above.

| Structure | Molecular Weight | Mass Spec Result |
| --- | --- | --- |
| 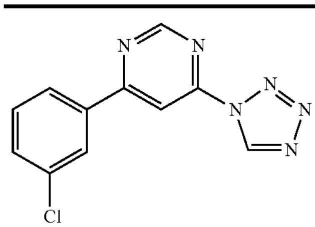 | 258.67 | [M + H]⁺ = 258, 98% @ rt = 4.27 min |

Example 25

Reaction Scheme 25

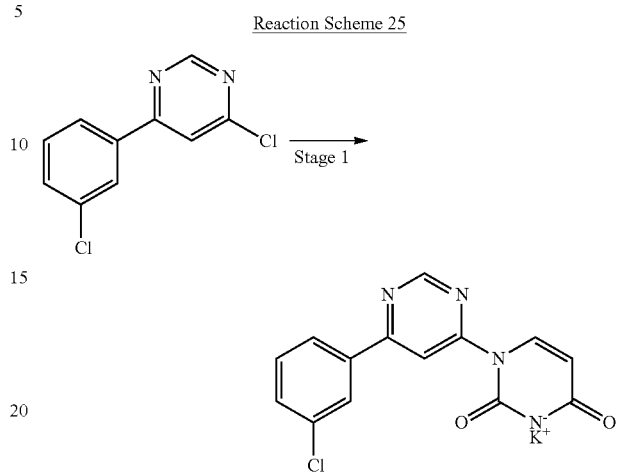

Referring to Reaction Scheme 25, stage 1, to a stirred solution of 4-chloro-6-(3-chlorophenyl)-pyrimidine (1 eq) in DMSO (20 vol) was added 1H-pyrimidine-2,4-dione (1 eq) and potassium carbonate (2 eq) and the reaction mixture was heated at 100° C. for 16 hours with stirring. The reaction mixture was then allowed to cool to room temperature, diluted with water (200 vol) and stirred at ambient temperature for 1 hour. The solid residue was filtered and washed with water (200 vol) and tert-butylmethylether (200 vol) to furnish the desired compound, which was further dried in a vacuum oven at 40° C. for 16 hours.

The following compounds were prepared substantially as described above.

| Structure | Molecular Weight | Mass Spec Result |
| --- | --- | --- |
| 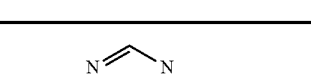 | 338.8 | [M + H]⁺ = 300, 100% @ rt = 3.90 min |

Example 26

Reaction Scheme 26

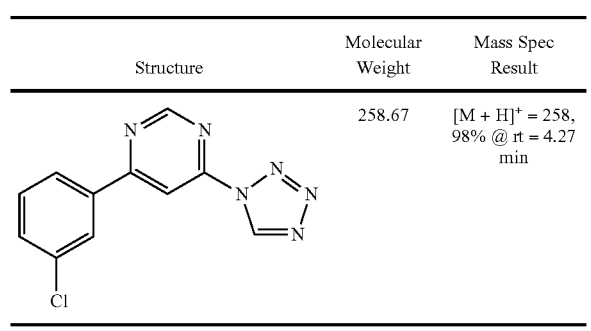

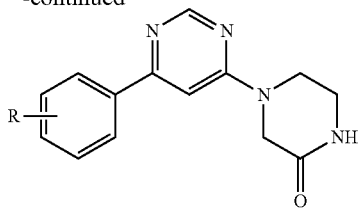

Referring to Reaction Scheme 26, stage 1, 1 solution of 4-chloro-6-(substituted-phenyl)-pyrimidine (1 eq) and piperazin-2-one (4 eq) in tert-butanol (10 vol) was heated at 150° C. with stirring in a microwave for 40 min. The solvent was removed in vacuo and trituration of the residue with acetonitrile/water (1/1) furnished the desired compound.

The following compounds were prepared substantially as described above.

| Structure | Molecular Weight | Mass Spec Result |
|---|---|---|
|  | 323.18 | [M + H]$^+$ = 324, 100% @ rt = 3.51 min |
|  | 323.18 | [M + H]$^+$ = 322, 99.6% @ rt = 3.77 min |

Example 27

Reaction Scheme 27

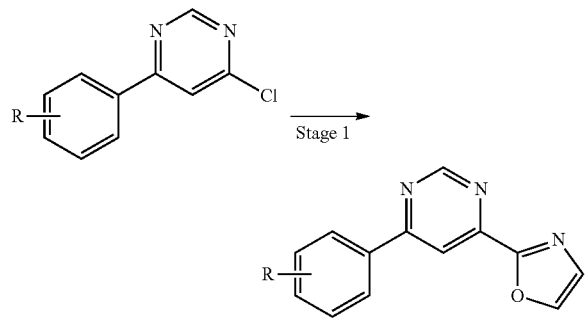

Referring to Reaction Scheme 27, stage 1, to a stirred solution of 1,3-oxazole (1.3 eq) in THF (10 vol) at −78° C. was added n-butyl lithium (1.4 eq) dropwise, the reaction was stirred at this temperature for 30 min before zinc chloride (3 eq) was added and the reaction warmed to room temperature with stirring over 1 hour. To the mixture was added palladium (tetrakis)triphenyl phosphine (0.05 eq) and 4-chloro-6-(substituted-phenyl)-pyrimidine (1 eq) and the mixture was heated to reflux with stirring for 2 hours. The reaction mixture was cooled to room temperature, poured onto HCl (1M, 20 vol) and extracted with diethyl ether (3×). The organic layers were combined, dried with MgSO$_4$, filtered and evaporated to dryness in vacuo. Purification by preparative HPLC afforded the desired compound.

The following compounds were prepared substantially as described above.

| Structure | Molecular Weight | Mass Spec Result |
|---|---|---|
| 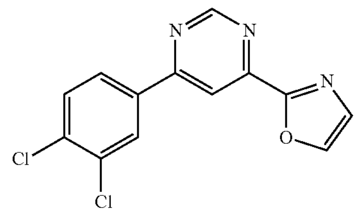 [SMILES: Clc1ccc(-c2cc(-c3ncco3)ncn2)cc1Cl] | 292.13 | [M + H]$^+$ = 292/294, 100% @ rt = 4.68 min |
| 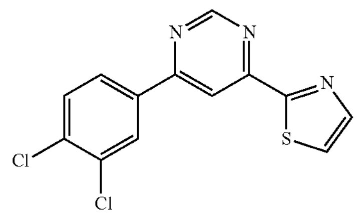 [SMILES: Clc1ccc(-c2cc(-c3nccs3)ncn2)cc1Cl] | 308.19 | [M + H]$^+$ = 308/310, 100% @ rt = 5.34 min |
| 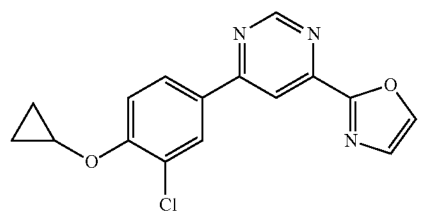 [SMILES: Clc1cc(-c2cc(-c3ncco3)ncn2)ccc1OC1CC1] | 313.75 | [M + H]+ = 314/315, 100% @ rt = 4.70 min |

Example 28

Reaction Scheme 28

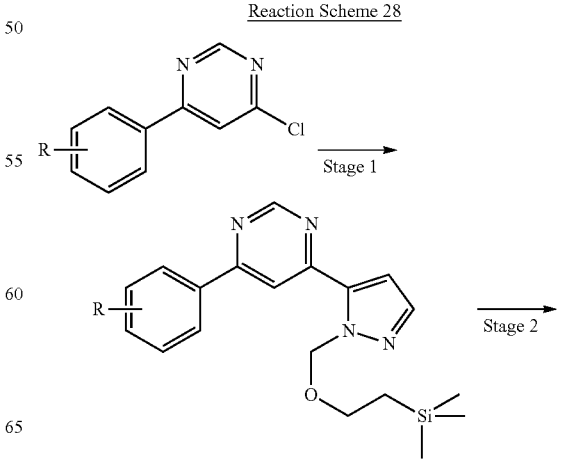

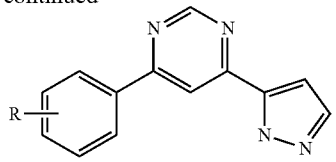

Referring to Reaction Scheme 28, stage 1, to a stirred solution of 4-chloro-6-(3,4-dichloro-phenyl)-pyrimidine (1 eq) and 5-(4,4,5,5-tetramethyl-[1,3,2]dioxaborolan-2-yl)-1-(2-trimethylsilanyl-ethoxymethyl)-1H-pyrazole (1.1 eq) in dioxane (10 vol) was added potassium carbonate (4 eq), the reaction was degassed with nitrogen, palladium (tetrakis) triphenyl phosphine (0.05 eq) was added and the mixture heated to reflux with stirring for 16 hours. The reaction mixture was cooled to room temperature, poured onto water (20 vol) and extracted with ethyl acetate (3×). The organic layers were combined, washed with brine (10 vol), dried with MgSO₄, filtered and evaporated to dryness in vacuo. Purification by flash column chromatography (eluent: [80:20] EtOAc:Heptane) afforded the desired compound.

Referring to Reaction Scheme 28, Stage 2, HCl in dioxane (4M, 10 eq) was added in one portion to a stirred solution of 4-(3,4-dichloro-phenyl)-6-[2-(2-trimethylsilanyl-ethoxymethyl)-2H-pyrazol-3-yl]-pyrimidine (1 eq) in dioxane (2 vol) and the mixture stirred at room temperature for 20 hours. The solvent was removed in vacuo, the residue was triturated with diethyl ether and the resulting precipitate was collected by filtration and dried under vacuum to afford the desired compound.

The following compounds were prepared substantially as described above.

| Structure | Molecular Weight | Mass Spec Result |
|---|---|---|
| (structure shown) | 291.14 | [M + H]⁺ = 291/293, 100% @ rt = 4.35 min |

Example 29

Reaction Scheme 29

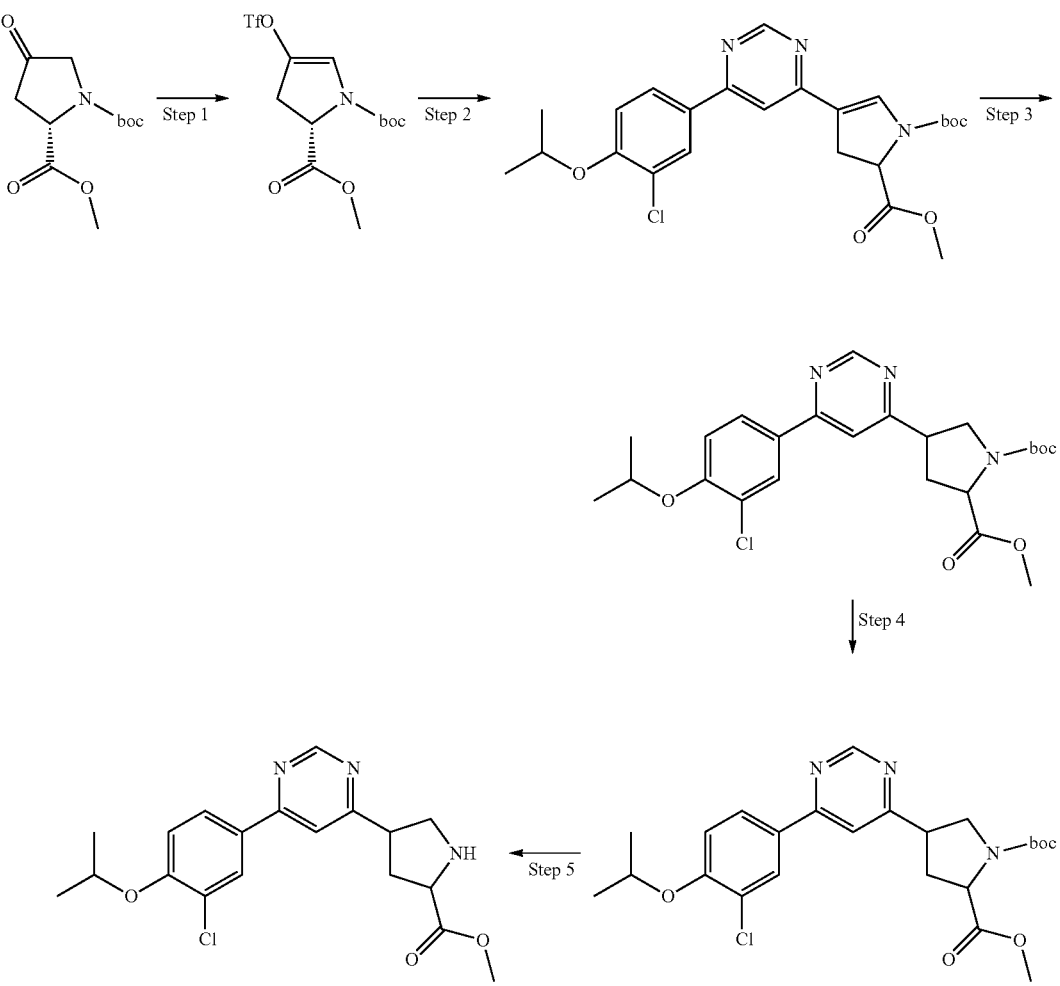

Example 29A

4-[6-(3-Chloro-4-isopropoxy-phenyl)-pyrimidin-4-yl]-pyrrolidine-2-carboxylic acid 4-Trifluoromethanesulfonyloxy-2,3-dihydro-pyrrole-1,2-dicarboxylic acid 1-tert-butyl ester 2-methyl ester

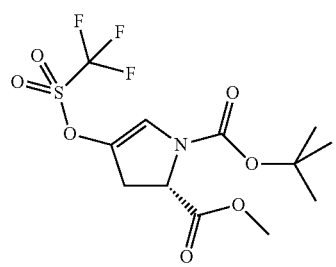 [SMILES: COC(=O)[C@@H]1CC(OS(=O)(=O)C(F)(F)F)=CN1C(=O)OC(C)(C)C]

Sodium hexamethyldisilazanide (2.3 ml of a 1M solution in THF, 2.26 mmol) was added drop wise to a cold (−78° C.), solution of 4-oxo-pyrrolidine-1,2-dicarboxylic acid 1-tert-butyl ester 2-methyl ester (0.5 g, 2.1 mmol) in THF (2 ml) and the mixture was stirred at this temperature for 1 hour. After this time, 1,1,1-trifluoro-N-phenyl-N-[(trifluoromethyl)sulfonyl]methanesulfonamide (0.89 g, 2.47 mmol) was added dropwise and the reaction stirred for a further 30 minutes. After this time the reaction mixture was allowed to warm to room temperature and the mixture was stirred overnight. The mixture was then partitioned between EtOAc (30 ml) and saturated ammonium chloride (10 ml), the organic layer was separated, dried (MgSO$_4$), filtered and concentrated. The resulting residue was purified by flash column chromatography (elution: 20% Ethyl Acetate, 80% heptane) to give the title compound (0.27 g, 36% yield) as a colourless oil. δ$_H$ (500 MHz, CDCl$_3$) 5.68-5.79 (m, 1H), 4.99-5.10 (m, 1H), 4.24-4.45 (m, 2H), 3.78 (s, 3H), 1.40-1.53 (m, 9H). Tr=3.58 min m/z (ES$^+$) (M+Na$^+$) 398.

4-[6-(3-Chloro-4-isopropoxy-phenyl)-pyrimidin-4-yl]-2,3-dihydro-pyrrole-1,2-dicarboxylic acid 1-tert-butyl ester 2-methyl ester

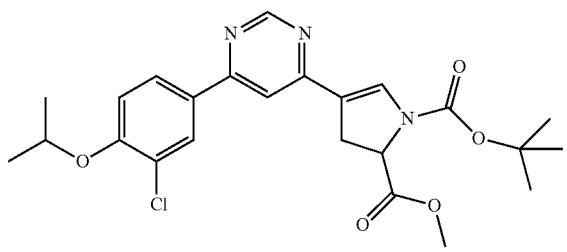 [SMILES: COC(=O)C1CC(c2cc(-c3ccc(OC(C)C)c(Cl)c3)ncn2)=CN1C(=O)OC(C)(C)C]

Hexamethyldistannane (5.6 ml, 2.7 mmol) and lithium chloride (0.34 g, 7.8 mmol) were added sequentially in one portion to a stirred solution of, 4-chloro-6-(3-chloro-4-isopropoxy-phenyl)-pyrimidine (0.75 g, 2.7 mmol) and 4-trifluoromethanesulfonyloxy-2,3-dihydro-pyrrole-1,2-dicarboxylic acid 1-tert-butyl ester 2-methyl ester (1.0 g, 2.7 mmol) in THF (40 ml). The mixture was degassed with nitrogen for 5 minutes, after which time palladium tetrakis(triphenylphosphine) (0.31 g, 0.26 mmol) was added in one portion, the mixture was then heated to 70° C. and stirred at this temperature for 16 hours under a nitrogen atmosphere. After this time the reaction mixture was cooled to room temperature and partitioned between ethyl acetate (200 ml) and saturated potassium fluoride (50 ml). The organic layer was separated, washed sequentially with water (100 ml) then brine (100 ml) before being dried (MgSO$_4$), filtered and concentrated. The resulting red gum was purified by flash column chromatography (elution: 80% EtOAc, 20% Heptane) to give the title compound (0.1 g, 9% yield) as a colourless oil. Tr=2.69 min m/z (ES$^+$) (M+H$^+$) 474.

4-[6-(3-Chloro-4-isopropoxy-phenyl)-pyrimidin-4-yl]-pyrrolidine-1,2-dicarboxylic acid 1-tert-butyl ester 2-methyl ester

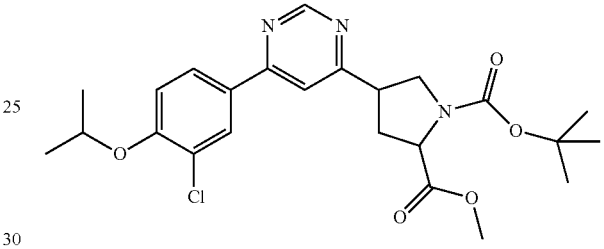

10% Palladium on carbon (0.22 g, 0.21 mmol) was added in one portion to a stirred solution of 4-[6-(3-chloro-4-isopropoxy-phenyl)-pyrimidin-4-yl]-2,3-dihydro-pyrrole-1,2-dicarboxylic acid 1-tert-butyl ester 2-methyl ester (0.03 g, 0.06 mmol) in EtOAc (15 ml) and the mixture was stirred at room temperature under a hydrogen atmosphere for 24 hours. After this time, the mixture was filtered through celite and the resulting filtrate concentrated to give the title compound (0.03 g, 22% yield) as a colourless oil. Tr=2.61 min m/z (ES$^+$) (M+H$^+$) 476.

4-[6-(3-Chloro-4-isopropoxy-phenyl)-pyrimidin-4-yl]-pyrrolidine-1,2-dicarboxylic acid 1-tert-butyl ester

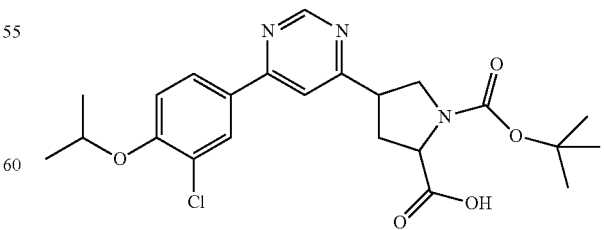

NaOH (2M solution, 0.16 ml, 0.33 mmol) was added in one portion to a stirred solution of 4-[6-(3-chloro-4-isopropoxy-phenyl)-pyrimidin-4-yl]-pyrrolidine-1,2-dicarboxylic acid 1-tert-butyl ester 2-methyl ester 2-methyl ester (0.03 g, 0.06 mmol) in THF (2 ml) and the mixture was stirred at room temperature for 16 hours. After this time, the mixture was acidified to pH 3 with HCl (1M solution), extracted with EtOAc (3×20 ml), the organic layers were separated and combined before being dried (MgSO$_4$), filtered, and concentrated to give the title compound (0.02 g, 48% yield) as a yellow oil. Tr=2.19 min m/z (ES$^+$) (M+H$^+$) 462.

4-[6-(3-Chloro-4-isopropoxy-phenyl)-pyrimidin-4-yl]-pyrrolidine-2-carboxylic acid

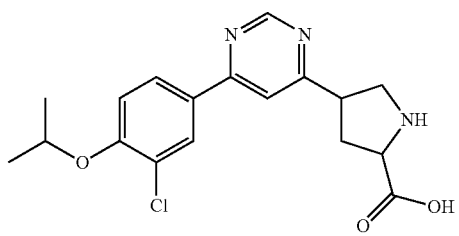 [SMILES: CC(C)Oc1ccc(-c2cc(C3CNC(C(=O)O)C3)ncn2)cc1Cl]

1M HCl in diethyl ether solution (2 ml) was added in one portion to a stirred solution of 4-[6-(3-chloro-4-isopropoxy-phenyl)-pyrimidin-4-yl]-pyrrolidine-1,2-dicarboxylic acid 1-tert-butyl ester (0.02 g, 0.03 mmol) in diethyl ether (1 ml) and the mixture was stirred at room temperature overnight. After this time the reaction mixture was concentrated and the resulting residue was purified by prep HPLC to give the title compound (0.005 g, 38% yield) as a cream solid.

Example 29A

4-[6-(3-Chloro-4-isopropoxy-phenyl)-pyrimidin-4-yl]-pyrrolidine-2-carboxylic acid δ$_H$ (500 MHz, MeOD) 9.04-9.14 (m, 1H) 8.20-8.32 (m, 1H) 8.04-8.17 (m, 1H) 7.85-7.97 (m, 1H) 7.24 (d, J=8.83 Hz, 1H) 4.76-4.83 (m, 1H) 4.08-4.28 (m, 1H) 3.64-3.84 (m, 3H) 2.25-2.93 (m, 2H) 1.42 (d, J=5.99 Hz, 6H). Tr=3.30 min m/z (ES$^+$) (M+H$^+$) 362.

The following compounds were prepared substantially as described above.

Example 30

Reaction Scheme 30

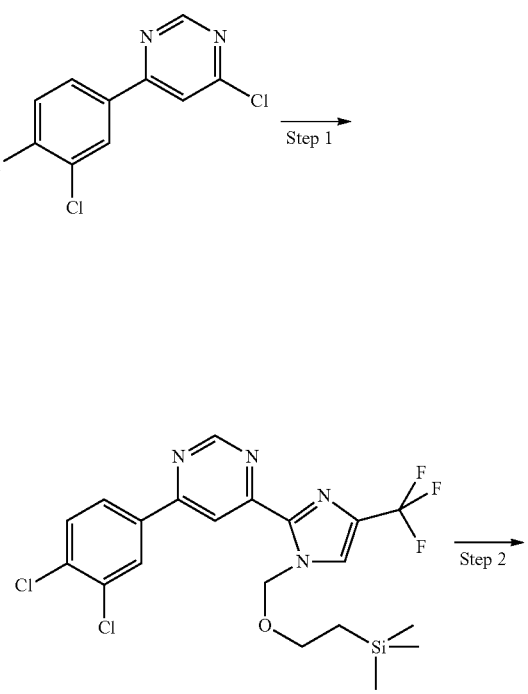

| Structure | Molecular Weight | Mass Spec Result |
|---|---|---|
| 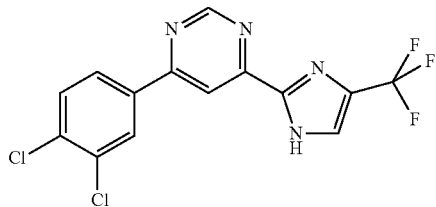 | 361.83 | [M + H]$^+$ = 362, 95% @ rt = 3.25/3.30 min |

Example-1

4-(3,4-Dichloro-phenyl)-6-(4-trifluoromethyl-1H-imidazol-2-yl)-pyrimidine 4-(3,4-Dichloro-phenyl)-6-[4-trifluoromethyl-1-(2-trimethylsilanyl-ethoxymethyl)-1H-imidazol-2-yl]-pyrimidine

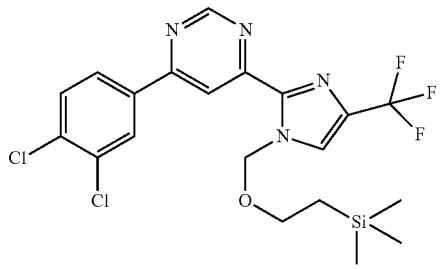 [SMILES: C[Si](C)(C)CCOCn1cc(C(F)(F)F)nc1-c1cc(-c2ccc(Cl)c(Cl)c2)ncn1]

n-Butyl lithium (2.5M solution in hexane, 0.11 ml, 0.27 mmol) was added dropwise to a cold (−78° C.) stirred solution of 4-trifluoromethyl-1-(2-trimethylsilanyl-ethoxymethyl)-1H-imidazole (0.067 g, 0.25 mmol) in THF (5 ml) and the mixture was stirred at this temperature under a nitrogen atmosphere for 30 minutes. After this time, $ZnCl_2$ (1M solution in $Et_2O$, 0.58 ml, 0.58 mmol) was added in one portion and the solution was allowed to warm to room temperature. 4-Chloro-6-(3,4-dichloro-phenyl)-pyrimidine (0.05 g, 0.19 mmol) and $Pd(PPh_3)_4$ (0.045 g, 0.01 mol) were added sequentially and the resulting mixture was heated to reflux and stirred for a further 4 hours. After this time the mixture was diluted with TBME (100 ml) and washed with 1M HCl (50 ml). The layers were separated and the aqueous extracted with TBME (50 ml). The organic layers were combined, dried ($MgSO_4$), filtered and concentrated. The resulting residue was purified using a Biotage Isolera (10 g silica column eluting with 100% heptane to 20% ethyl acetate/80% heptane) to afford the title compound (0.064 g, 68% yield) as a white solid. $\delta_H$ (250 MHz, $CDCl_3$) 9.26 (d, J=1.22 Hz, 1H), 8.60 (d, J=1.37 Hz, 1H), 8.37 (d, J=2.13 Hz, 1H), 8.06 (dd, J=2.13, 8.53 Hz, 1H), 7.52-7.75 (m, 2H), 6.13 (s, 2H), 3.65 (dd, J=7.77, 8.68 Hz, 2H), 0.79-1.05 (m, 2H), −0.03 (s, 9H). Tr=2.66 min m/z ($ES^+$) ($M+H^+$) 489, 491.

4-(3,4-Dichloro-phenyl)-6-(4-trifluoromethyl-1H-imidazol-2-yl)-pyrimidine

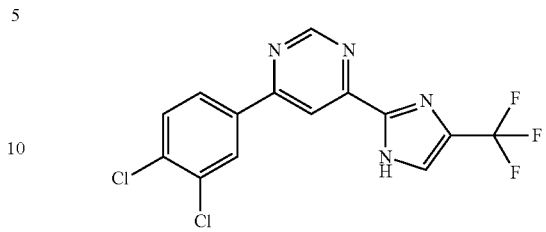

Boron trifluoride diethyl etherate (0.16 ml, 1.3 mmol) was added dropwise to a cool (0° C.), stirred solution of 4-(3,4-dichloro-phenyl)-6-[4-trifluoromethyl-1-(2-trimethylsilanyl-ethoxymethyl)-1H-imidazol-2-yl]-pyrimidine (0.064 g, 0.13 mmol) in DCM (2 ml) under a nitrogen atmosphere. The mixture was stirred at this temperature for 10 minutes before being allowed to warm to room temperature and stirred overnight. The solution was diluted with heptane (5 ml) and the resulting precipitate was collected by filtration and dried under vacuum before being purified by prep HPLC to give the title compound (0.05 g, 15% yield) as a white powder.

Example-1

4-(3,4-Dichloro-phenyl)-6-(4-trifluoromethyl-1H-imidazol-2-yl)-pyrimidine $\delta_H$ (500 MHz, DMSO) 14.02 (br. s, 1H), 9.36 (d, J=1.26 Hz, 1H), 8.59 (d, J=1.26 Hz, 1H), 8.57 (d, J=2.05 Hz, 1H), 8.32 (dd, J=2.21, 8.51 Hz, 1H), 8.09 (d, J=0.63 Hz, 1H), 7.85 (d, J=8.51 Hz, 1H). Tr=4.94 min m/z ($ES^+$) ($M+H^+$) 359, 361.

The following compounds were prepared substantially as described above.

| Structure | Molecular Weight | Mass Spec Result |
|---|---|---|
| Example 31 | 359.14 | [M + H]+ = 359/361, 99% @ rt = 4.94 min |

Reaction Scheme 31

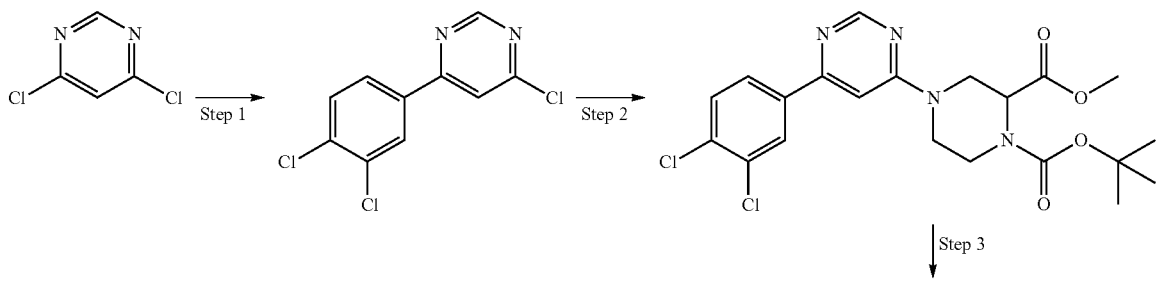

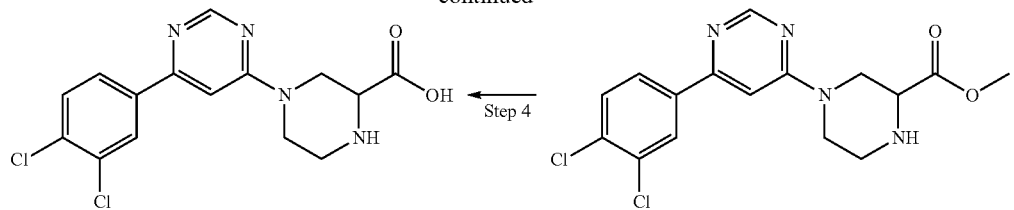

Step 4

Example 31A

4-{6-[3-chloro-4-(propan-2-yloxy)phenyl]pyrimidin-4-yl}pyrrolidine-2-carboxylic acid 4-Chloro-6-(3,4-dichloro-phenyl)-pyrimidine

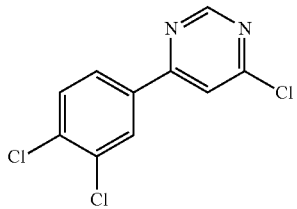 [SMILES: Clc1cc(-c2ccc(Cl)c(Cl)c2)ncn1]

Potassium carbonate (2M solution, 200 ml, 400.0 mmol) was added in one portion to a stirred solution of 3,4-dichlorophenyl boronic acid (38.5 g, 201.4 mmol) and 4,6-dichloropyrimidine (50.0 g, 335.6 mmol) in dioxane (600 ml). The mixture was degassed with nitrogen for 5 minutes, after which time palladium tetrakis triphenylphosphine (7.78 g, 6.71 mmol) was added in one portion, the mixture was then heated to 90° C. and stirred at this temperature for 16 hours under a nitrogen atmosphere. After this time the reaction mixture was cooled to room temperature and concentrated. The resulting residue was dissolved in DCM (500 ml), washed sequentially with water (200 ml) then brine (200 ml) before being dried (MgSO₄), filtered and concentrated to give the title compound (47.8 g, 91% yield) as a white solid which was used without further purification. Tr=2.32 min m/z (ES⁺) (M+H⁺) 258, 260.

4-[6-(3,4-Dichloro-phenyl)-pyrimidin-4-yl]-piperazine-1,2-dicarboxylic acid 1-tert-butyl ester 2-methyl ester

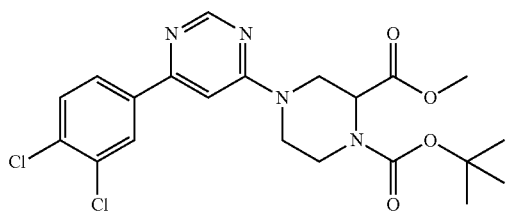 [SMILES: COC(=O)C1CN(c2cc(-c3ccc(Cl)c(Cl)c3)ncn2)CCN1C(=O)OC(C)(C)C]

4-Chloro-6-(3,4-dichloro-phenyl)-pyrimidine (0.11 g, 0.4 mmol) was added in one portion to a suspension of piperazine-1,2-dicarboxylic acid 1-tert-butyl ester 2-methyl ester (0.21 g, 0.85 mmol) and in tert-butanol (2 ml) in a microwave reactor tube. The tube was sealed and heated to 150° C. in a microwave for 40 minutes at a pressure of 250 psi. After this time the reaction mixture was cooled to room temperature and the solvent was removed. The resulting residue was purified by flash column chromatography (elution: 20% EtOAc, 80% Heptane) to give the title compound (0.36 g, 75% yield) as a colourless oil. δ$_H$ (500 MHz, DMSO) 8.59 (s, 1H) 8.43 (d, J=2.05 Hz, 1H) 8.17 (dd, J=8.51, 2.05 Hz, 1H) 7.74-7.81 (m, 1H) 7.42 (d, J=7.88 Hz, 1H) 4.88-5.09 (m, 1H) 4.60-4.76 (m, 1H) 4.24-4.46 (m, 1H) 3.76-3.88 (m, 1H) 3.56 (d, J=13.08 Hz, 3H) 3.38-3.51 (m, 1H) 3.10-3.28 (m, 2H) 1.31-1.47 (m, 9H). Tr=3.71 min m/z (ES⁺) (M+H⁺) 283, 285.

4-[6-(3,4-Dichloro-phenyl)-pyrimidin-4-yl]-piperazine-2-carboxylic acid methyl ester

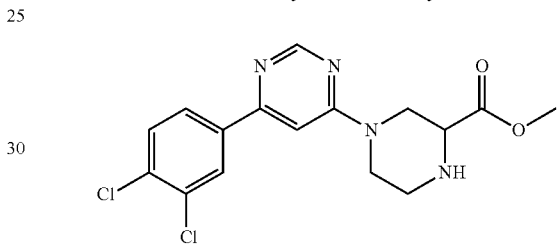

4M HCl in dioxane solution (8 ml) was added in one portion to a stirred solution of 4-[6-(3,4-Dichloro-phenyl)-pyrimidin-4-yl]-piperazine-1,2-dicarboxylic acid 1-tert-butyl ester 2-methyl ester (0.36 g, 0.75 mmol) in dioxane (2 ml) and the mixture was stirred at room temperature overnight. After this time the reaction mixture was concentrated and the resulting residue was partitioned between DCM (100 ml) and saturated sodium bicarbonate (75 ml) and stirred at room temperature for 10 minutes. The mixture was then extracted with DCM (3×100 ml), the organic layers were combined, separated and washed with brine (50 ml). The organic layer was removed, dried (MgSO₄) filtered and concentrated to give the title compound (0.27 g, 87% yield) as a yellow solid. δ$_H$ (500 MHz, CDCl₃) 8.70 (s, 1H) 8.11 (d, J=2.05 Hz, 1H) 7.84 (dd, J=8.35, 2.05 Hz, 1H) 7.55 (d, J=8.35 Hz, 1H) 6.89 (s, 1H) 4.35 (d, J=11.51 Hz, 1H) 3.99 (d, J=12.93 Hz, 1H) 3.79 (s, 3H) 3.53-3.66 (m, 2H) 3.48 (ddd, J=12.65, 9.10, 3.15 Hz, 1H) 3.14-3.21 (m, 1H) 2.92 (ddd, J=12.10, 8.87, 3.31 Hz, 1H) 2.36 (br. s, 1H). Tr=1.48 min m/z (ES⁺) (M+H⁺) 367, 369.

4-[6-(3,4-Dichloro-phenyl)-pyrimidin-4-yl]-piperazine-2-carboxylic acid

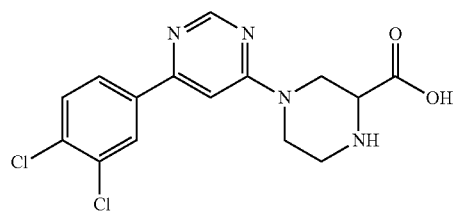 [SMILES: O=C(O)C1CN(c2cc(-c3ccc(Cl)c(Cl)c3)ncn2)CCN1]

NaOH (2M solution, 0.12 ml, 0.24 mmol) was added in one portion to a stirred solution of 6-(3,4-dichloro-phenyl)-pyrimidine-4-carboxylic acid methyl ester (0.1 g, 0.27 mmol) in THF (10 ml) and the mixture was stirred at room temperature for 16 hours. After this time, the resulting precipitate was collected by filtration, washed with water (1 ml) and DCM (20 ml) before being dried under vacuum to give the sodium salt of the title compound (0.05 g, 49% yield) as a white solid.

Example-1

4-{6-[3-chloro-4-(propan-2-yloxy)phenyl]pyrimidin-4-yl}pyrrolidine-2-carboxylic acid $\delta_H$ (500 MHz, D$_2$O) 8.25 (s, 1H) 7.59 (d, J=2.05 Hz, 1H) 7.46 (dd, J=8.51, 2.05 Hz, 1H) 7.35 (d, J=8.35 Hz, 1H) 6.62 (s, 1H) 4.21 (br. s, 1H) 4.01 (d, J=11.51 Hz, 1H) 3.32 (dd, J=10.01, 3.39 Hz, 1H) 3.05-3.19 (m, 3H) 2.72-2.84 (m, 1H). Tr=2.80 min m/z (ES$^+$) (M+H$^+$) 353, 355.

Example 31B

1-[6-(3,4-Dichloro-phenyl)-pyrimidin-4-yl]-piperazine-2-carboxylic acid $\delta_H$ (500 MHz, D$_2$O) 9.48 (s, 1H) 8.64 (s, 1H) 8.30-8.49 (m, 2H) 8.01 (s, 1H) 6.56 (br. s, 1H) 5.20-5.50 (m, 1H) 4.78-4.87 (m, 1H) 3.90-4.45 (m, 4H). Tr=2.94 min m/z (ES$^+$) (M+H$^+$) 353

The following compounds were prepared substantially as described above.

| Structure | Molecular Weight | Mass Spec Result |
|---|---|---|
| 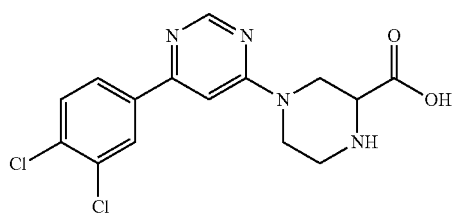 [SMILES: O=C(O)C1CN(c2cc(-c3ccc(Cl)c(Cl)c3)ncn2)CCN1] | 353.2 | [M + H]+ = 353/354, 100% @ rt = 2.90 min |
| 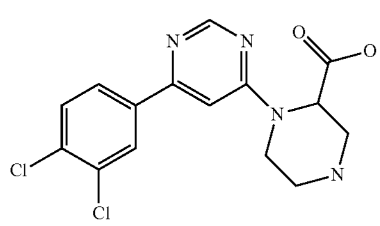 [SMILES: O=C(O)C1CNCCN1c1cc(-c2ccc(Cl)c(Cl)c2)ncn1] | 353.21 | [M + H]+ = 353, 100% @ rt = 2.94 min |

Example 32

Reaction Scheme 32

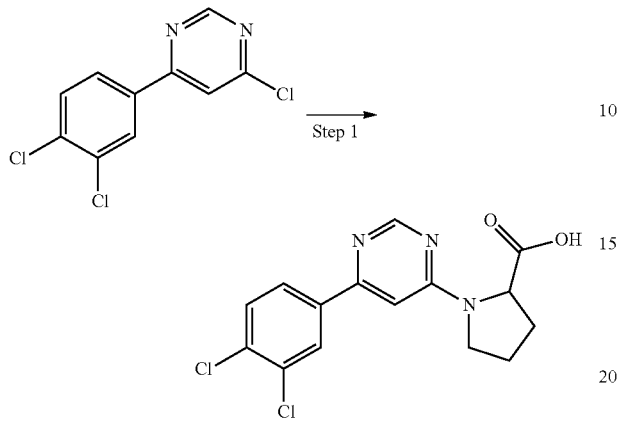

Example-1

1-[6-(3,4-Dichloro-phenyl)-pyrimidin-4-yl]-pyrrolidine-2-(R)-carboxylic acid

1-[6-(3,4-Dichloro-phenyl)-pyrimidin-4-yl]-pyrrolidine-2-(R)-carboxylic acid

4-Chloro-6-(3,4-dichloro-phenyl)-pyrimidine (0.3 g, 1.2 mmol) and D-proline (0.13 g, 1.2 mmol) were added in one portion to a pressure vessel containing a solution of copper (I) Iodide (0.02 g, 0.16 mmol) and potassium carbonate (0.24 g, 1.8 mmol) in DMA (5 ml). The vessel was sealed and heated at 90° C. for 16 hours before being cooled to room temperature. The mixture was cooled to room temperature, diluted with ethyl acetate (10 ml) and acidified to pH 1 with concentrated HCl. The mixture was extracted with ethyl acetate (3×30 ml) and the organic layers were combined, dried (MgSO$_4$), filtered, concentrated and the resulting residue was purified by prep HPLC to give the title compound (0.17 g, 43% yield) as a white solid.

Example-1

1-[6-(3,4-Dichloro-phenyl)-pyrimidin-4-yl]-pyrrolidine-2-(R)-carboxylic acid $\delta_H$ (250 MHz, DMSO) 8.54 (s, 1H) 8.32 (d, J=2.13 Hz, 1H) 8.08 (dd, J=8.45, 2.06 Hz, 1H) 7.72 (d, J=8.53 Hz, 1H) 7.03 (s, 1H) 4.62 (dd, J=8.68, 2.89 Hz, 1H) 3.59-3.72 (m, 2H) 1.95-2.41 (m, 4H). Tr=3.64 min m/z (ES$^+$) (M+H$^+$) 338.

Example-2

1-[6-(3,4-Dichloro-phenyl)-pyrimidin-4-yl]-pyrrolidine-2-(R)-carboxylic acid $\delta_H$ (250 MHz, DMSO) 8.54 (d, J=0.76 Hz, 1H) 8.31 (d, J=1.98 Hz, 1H) 8.08 (dd, J=8.45, 2.06 Hz, 1H) 7.71 (d, J=8.38 Hz, 1H) 7.02 (s, 1H) 4.62 (dd, J=8.68, 2.89 Hz, 1H) 3.65 (t, J=6.24 Hz, 2H) 1.94-2.42 (m, 4H). Tr=3.55 min m/z (ES$^+$) (M+H$^+$) 338.

Example-3

1-[6-(3,4-Dichloro-phenyl)-pyrimidin-4-yl]-pyrrolidine-3-carboxylic acid $\delta_H$ (500 MHz, DMSO) 8.55 (s, 1H) 8.37-8.48 (m, 1H) 8.11-8.24 (m, 1H) 7.75 (d, J=8.51 Hz, 1H) 7.12 (br. s, 1H) 3.47-3.82 (m, 5H) 2.22 (br. s, 2H). Tr=3.38 min m/z (ES$^+$) (M+H$^+$) 338.

The following compounds were prepared substantially as described above.

| Structure | Molecular Weight | Mass Spec Result |
|---|---|---|
| 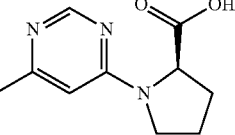 | 338.2 | [M + H]+ = 338, 97% @ rt = 3.64 min |
| 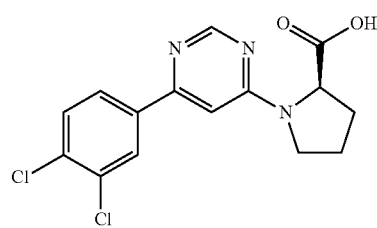 [SMILES: O=C(O)[C@H]1CCCN1c1cc(-c2ccc(Cl)c(Cl)c2)ncn1] | 338.2 | [M + H]+ = 338, 100% @ rt = 3.55 min |

-continued
| Structure | Molecular Weight | Mass Spec Result |
|---|---|---|
| 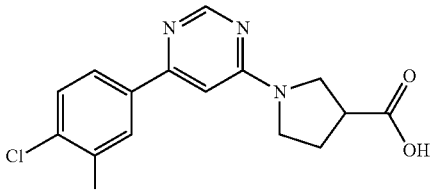 | 338.2 | [M + H]+ = 338, 99% @ rt = 3.38 min |
Example 33
Reaction Scheme 33
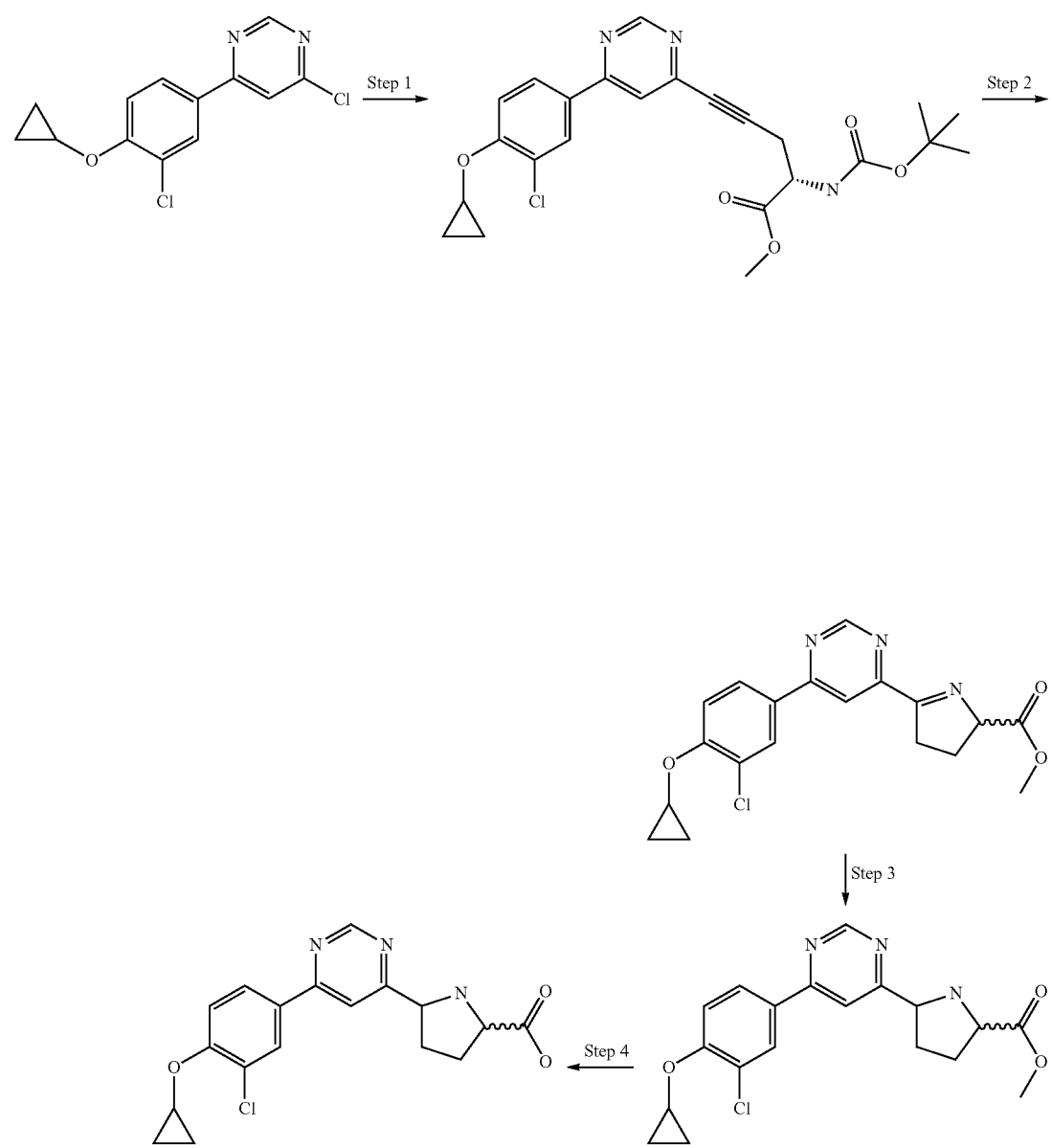

Example-1

5-[6-(3-chloro-4-cyclopropoxyphenyl)pyrimidin-4-yl]pyrrolidine-2-carboxylic acid Methyl (2S)-2-{[(tert-butoxy)carbonyl]amino}-5-[6-(3-chloro-4-cyclopropoxyphenyl)pyrimidin-4-yl]pent-4-ynoate

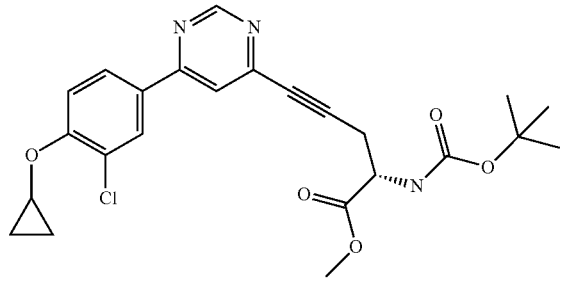 [SMILES: COC(=O)[C@H](CC#Cc1cc(-c2ccc(OC3CC3)c(Cl)c2)ncn1)NC(=O)OC(C)(C)C]

Diisopropyl ethylamine (10 ml) triethylamine (5 ml) were added portion wise to a pressure vessel containing (2S)-2-{[tert-butoxy)carbonyl]amino}pent-4-ynoate (2.4 g, 21.3 mmol), 4-chloro-6-(3-chloro-4-cyclopropoxyphenyl)pyrimidine (2.0 g, 7.11 mmol), copper (I) iodide (0.07 g, 0.36 mmol) and triphenylphosphine (0.09 g, 0.71 mmol). The mixture was degassed with nitrogen for 10 minutes, Pd(Cl$_2$) (dppO$_2$) (0.25 g, 0.3 mmol) was added, the vessel was sealed and heated to 100° C. for 30 minutes in a microwave reactor. After this time, the reaction mixture was cooled to room temperature concentrated, the resulting residue was dissolved in ethyl acetate (30 ml) and washed with brine (20 ml). The organic layer was separated, dried (MgSO$_4$), filtered and concentrated. The resulting residue was purified using a Biotage Isolera (25 g silica column eluting with 12% ethyl acetate/78% heptane to 100% ethyl acetate) to afford the title compound (2.26 g, 67% yield) as a yellow solid. Tr=2.43 min m/z (ES$^+$) (M+H$^+$) 471, 472.

Methyl (2S)-2-amino-5-[6-(3-chloro-4-cyclopropoxyphenyl)pyrimidin-4-yl]pent-4-ynoate

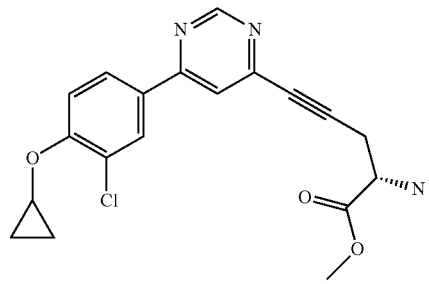 [SMILES: COC(=O)[C@@H](N)CC#Cc1cc(-c2ccc(OC3CC3)c(Cl)c2)ncn1]

Trifluoroacetic acid (6 ml) was added dropwise to a stirred solution of methyl (2S)-2-{[(tert-butoxy)carbonyl]amino}-5-[6-(3-chloro-4-cyclopropoxyphenyl)pyrimidin-4-yl]pent-4-ynoate (2.26 g, 4.8 mmol) in dichloromethane (20 ml) and the mixture was stirred at room temperature overnight. After this time the reaction mixture was concentrated and the resulting residue redissolved in DCM (20 ml) before being washed with saturated sodium bicarbonate. The organic layer was separated, dried (MgSO$_4$), filtered and concentrated to give the title compound (1.64 g, 92% yield) as a brown oil. Tr=1.63 min m/z (ES$^+$) (M+H$^+$) 372, 373.

Methyl 5-[6-(3-chloro-4-cyclopropoxyphenyl)pyrimidin-4-yl]pyrrolidine-2-carboxylate

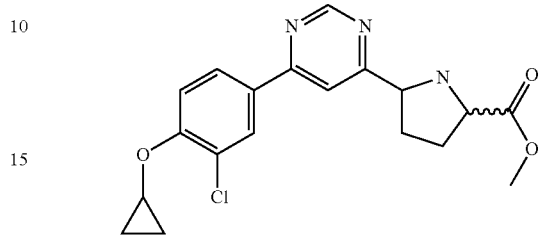

Silver triflate (0.17 g, 0.67 mmol) was added portion wise to a stirred solution of methyl (2S)-2-amino-5-[6-(3-chloro-4-cyclopropoxyphenyl)pyrimidin-4-yl]pent-4-ynoate (0.5 g, 1.3 mmol) in methanol (10 ml) and the mixture was stirred at room temperature overnight. After this time the solid precipitate was removed by filtration and the filtrate concentrated. The resulting residue was dissolved in methanol (5 ml), cooled to 0° C., treated with sodium borohydride (0.2 g, 5.0 mmol) and stirred at 0° C. for 2 hours. After this time the reaction mixture was quenched by the careful addition of saturated sodium bicarbonate (1 ml), the mixture was concentrated and the resulting residue partitioned between ethyl acetate (20 ml) and water (10 ml). The organic layer was removed, dried (MgSO$_4$), filtered and concentrated. The residue was purified by prep HPLC to give the title compound (0.03 g, 5% yield) as a brown oil. Tr=2.22 min m/z (ES$^+$) (M+H$^+$) 373.

5-[6-(3-chloro-4-cyclopropoxyphenyl)pyrimidin-4-yl]pyrrolidine-2-carboxylic acid

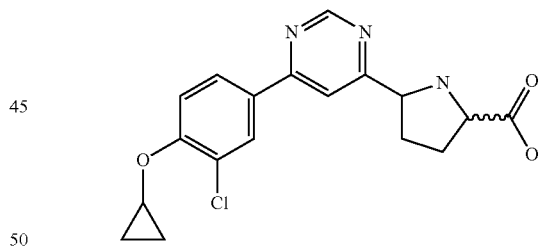

NaOH (2M solution, 0.04 ml, 0.073 mmol) was added in one portion to a stirred solution of methyl 5-[6-(3-chloro-4-cyclopropoxyphenyl)pyrimidin-4-yl]pyrrolidine-2-carboxylate (0.008 g, 0.02 mmol) in THF (2 ml) and the mixture was stirred at room temperature for 16 hours. After this time, the mixture was concentrated and the resulting residue purified by prep HPLC to give the title compound (0.001 g, 5% yield) as a white solid.

Example-1

5-[6-(3-chloro-4-cyclopropoxyphenyl)pyrimidin-4-yl]pyrrolidine-2-carboxylic acid δ$_H$ (500 MHz, MeOD) 8.93-9.06 (m, 1H), 8.12-8.18 (m, 1H), 8.05 (dd, J=2.29, 8.75 Hz, 1H), 7.89-7.98 (m, 1H), 7.46

(d, J=8.67 Hz, 1H), 4.66 (t, J=7.25 Hz, 1H), 3.84-3.97 (m, 2H), 2.31-2.39 (m, 1H), 2.22-2.31 (m, 1H), 1.95-2.04 (m, 1H), 1.85-1.95 (m, 1H), 0.63-0.84 (m, 4H). Tr=3.26 min m/z (ES$^+$) (M+H$^+$) 360, 362.

The following compounds were prepared substantially as described above.

| Structure | Molecular Weight | Mass Spec Result |
|---|---|---|
| 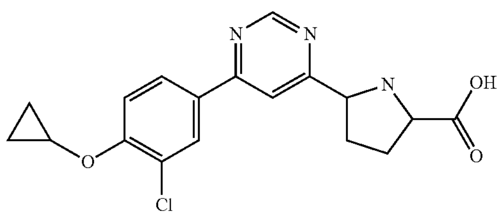 [SMILES: O=C(O)C1CCC(c2cc(-c3ccc(OC4CC4)c(Cl)c3)ncn2)N1] | 359.81 | [M + H]+ = 360/362 100% @ rt = 3.26 min |

Example 34

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 μl in 96 well cell plate
Substrate: L-Kynurenine (Sigma: Cat# K3750, stock concentration: 10 mM in 100 mM potassium phosphate buffer, pH 7.4)

Assay Conditions:
Medium: OptiMem (Reduced Serum Medium 1×, +L-Glutamine+HEPES—Phenol Red; GIBCO: Cat#11058)
Assay Volume: 200 μl
Plate Format: 96 well plate, transparent (Corning)
Read-Out: product (3OH-KYN) quantification using product specific MRM
Reader: LC/MS/MS
Assay Protocol:
  prepare serial dilution (factor 3) of compound in 100% DMSO (top concentration=6.67 mM, 100% DMSO)
    [8 points: 6.67 mM; 2.22 mM; 0.74 mM; 0.247 mM; 0.082 mM; 0.027 mM; 0.009 mM; 0.003 mM]
  prepare 300-fold concentrated solution of each compound concentration (top concentration 22.22 μM, 0.3% DMSO) in OptiMem medium
    [22.2 μM; 7.41 μM; 2.47 μM; 0.82 μM; 0.27 μM; 0.09 μM; 0.03 μM; 0.01 μM]
  prepare substrate (10 mM) at concentration of 1.1 mM in medium
  medium of cell plate is drawed off
  cells are washed with OptiMem (100 μl/well) and drawed off again
  assay mix: 90 μl OptiMem/well+90 μl compound/well of each concentration
    [final compound top concentration: 10 μM; 0.15% DMSO]
    [final compound bottom concentration: 0.004 μM; 0.15% DMSO]
  pre-incubation: 30 min at 37° C.
  add 20 μl/well of the 1.1 mM substrate solution (final assay concentration: 100 μM)
  positive control: 200 μl OptiMem
  negative control: 180 μl OptiMem+20 μl 1.1 mM substrate
  incubate ~24 h at 37° C.
  transfer 100 μl of each well in a transparent 96 well plate (Corning)
  add 100 μl/well 10% trichloro acetic acid (TCA) in water
  centrifugate plate for 3 min at 4000 rpm
  detect product by LC/MS (injection of 50 μl/well; 2.5 fold overfill of the 20 μl sample loop)
Data analysis: IC$_{50}$'s are calculated using automated fitting algorithm (A+ Analysis).

Example 35

A method of monitoring L-Kynurenine (KYN) hydroxylation to form product 3-Hydroxy-Kynurenine (3OH-KYN) by LC/MS is described below. Product is quantified by multiple reaction monitoring.

Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat# K3750)
  [stock concentration: 10 mM in 100 mM potassium phosphate buffer, pH 7.4]

Assay Conditions:
Buffer: 100 mM potassium phosphate, pH 7.4, 200 μM NADPH,
  0.4 U/ml G6P-DH (Glucose 6-phosphate dehydrogenase), 3 mM G6P (D-Glucose 6-phosphate)
Assay Volume: 40 μl
Plate Format: 384 well plate, transparent (Matrix)
Read-Out: product (3OH-KYN) quantification using product specific
  MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 μM, 3% DMSO) in assay buffer
    [concentrations: 300 μM; 100 μM; 33.3 μM; 11.1 μM; 3.70 μM; 1.23 μM; 0.41 μM; 0.137 μM]
  prepare substrate (10 mM) at concentration of 1 mM in assay buffer
  assay mix: 4 μl compound/well of each concentration+24 μl assay buffer/well+8 μl KMO human enzyme+4 μl 1 mM substrate (final concentration=100 μM)
    [final compound top concentration: 30 μM; 0.3% DMSO]

[final compound bottom concentration: 0.0137 µM; 0.3% DMSO]

positive control: 4 µl 50 µM FCE28833 in assay buffer [0.5% DMSO] (final assay concentration=5 µM)+24 µl assay buffer/well+8 µl KMO human enzyme+4 µl 1 mM substrate (final concentration=100 µM)

negative control: 28 µl assay buffer/well+8 µl KMO human enzyme+4 µl 1 mM substrate (final concentration=100 µM)

incubate 400 min at RT add 40 µl/well 10% trichloro acetic acid in water to stop the assay and precipitate protein centrifuge plate for 3 min at 4000 rpm product detection by LC/MS (injection of 50 µl/well; 2.5 fold overfill of the 20 µl sample loop)

Data analysis: $IC_{50}$'s are calculated using automated fitting algorithm (A+ Analysis).

Example 36

A method of monitoring L-Kynurenine (KYN) hydroxylation to form 3-Hydroxy-Kynurenine (3OH-KYN) by LC/MS is described. Product is quantified by multiple reaction monitoring (MRM method).

Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration:
  10 mM in 100 mM potassium phosphate buffer, pH 7.4)
Assay Conditions:
Buffer: 100 mM potassium phosphate, pH 7.4, 200 µM NADPH,
  0.4 U/ml G6P-DH (Glucose 6-phosphate Dehydrogenase), 3 mM
  G6P (D-Glucose 6-phosphate)
Assay Volume: 40 µl
Plate Format: 384 well plate, transparent (Matrix)
Read-Out: product (3OH-KYN) quantification using product specific
  MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
    [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO mouse enzyme+4 µl 1 mM substrate (final concentration=100 µM)
    [final compound top concentration: 30 µM; 0.3% DMSO]
    [final compound bottom concentration: 0.0137 µM; 0.3% DMSO]
  positive control: 4 µl 50 µM FCE28833 in assay buffer, 0.5% DMSO [final assay concentration=5 µM]+24 µl assay buffer/well+8 µl KMO mouse enzyme+4 µl 1 mM substrate [final concentration=100 µM]
  negative control: 28 µl assay buffer/well+8 µl KMO mouse enzyme+4 µl 1 mM substrate [final concentration=100 µM]
  incubate 40 min at RT
  add 40 µl/well 10% trichloro acetic acid in water to stop the assay and precipitate protein
  centrifuge plate for 3 min at 4000 rpm
  product detection by LC/MS (injection of 20 µl/well, 2 fold overfill of the 10 µl sample loop)
Data analysis: $IC_{50}$'s are calculated using automated fitting algorithm (A+ Analysis).

Example 37

Using procedures similar to those described herein, the following compounds were assayed for activity.

| IUPAC Name | INH.Mouse @ 10 µM |
| --- | --- |
| 2-[6-(3,4-dichlorophenyl)pyrimidin-4-yl]-1H-benzimidazole | 49.74 |
| 2-[6-(3-chlorophenyl)pyrimidin-4-yl]-1,3-benzoxazole | 54.41 |
| 2-[6-(3-chlorophenyl)pyrimidin-4-yl]-1H-benzimidazole | 102.1 |
| 3-[6-(3,4-dichlorophenyl)pyrimidin-4-yl]-4H-1,2,4-oxadiazol-5-one | 101.78 |
| 3-[6-(3,4-dichlorophenyl)pyrimidin-4-yl]-4H-1,2,4-oxadiazol-5-one | 101.2 |
| 3-[6-(3,4-dichlorophenyl)pyrimidin-4-yl]-4H-1,2,4-oxadiazole-5-thione | 102.13 |
| 3-[6-(3,4-Difluoro-phenyl)-pyrimidin-4-yl]-4H-[1,2,4]oxadiazol-5-one | 100 |
| 3-[6-(3-Chloro-4-fluoro-phenyl)-pyrimidin-4-yl]-4H-[1,2,4]oxadiazol-5-one | 100 |
| 3-[6-(3-Chloro-4-isopropoxy-phenyl)-pyrimidin-4-yl]-4H-[1,2,4]oxadiazol-5-one | 96 |
| 3-[6-(3-Chloro-4-methyl-phenyl)-pyrimidin-4-yl]-4H-[1,2,4]oxadiazol-5-one | 98 |
| 3-[6-(3-Chloro-4-trifluoromethoxy-phenyl)-pyrimidin-4-yl]-4H-[1,2,4]oxadiazol-5-one | 99 |
| 3-[6-(3-chlorophenyl)pyrimidin-4-yl]-4H-1,2,4-oxadiazol-5-one | 96.28 |
| 3-[6-(3-Fluoro-4-methyl-phenyl)-pyrimidin-4-yl]-4H-[1,2,4]oxadiazol-5-one | 100 |
| 3-[6-(5-chloropyridin-3-yl)pyrimidin-4-yl]-4H-1,2,4-oxadiazol-5-one | 65.18 |
| 4-(3,4-dichlorophenyl)-2-methyl-6-(4-methyl-1,3-oxazol-2-yl)pyrimidine | 46.84 |
| 4-(3,4-dichlorophenyl)-6-(1,2,4-oxadiazol-3-yl)pyrimidine | 68.52 |
| 4-(3,4-dichlorophenyl)-6-(1H-imidazol-2-yl)pyrimidine | 99 |
| 4-(3,4-Dichloro-phenyl)-6-(1H-pyrazol-3-yl)-pyrimidine | 19 |
| 4-(3,4-dichlorophenyl)-6-(1H-tetrazol-5-yl)pyrimidine | 102.49 |
| 4-(3,4-dichlorophenyl)-6-(1-methyltetrazol-5-yl)pyrimidine | 92.72 |

-continued

| IUPAC Name | INH.Mouse @ 10 μM |
|---|---|
| 4-(3,4-dichlorophenyl)-6-(2-methyltetrazol-5-yl)pyrimidine | 97.57 |
| 4-(3,4-dichlorophenyl)-6-(4,5-dihydro-1H-imidazol-2-yl)pyrimidine | 95.45 |
| 4-(3,4-dichlorophenyl)-6-(4H-1,2,4-triazol-3-yl)pyrimidine | 100.29 |
| 4-(3,4-dichlorophenyl)-6-(4-methyl-1,3-oxazol-2-yl)pyrimidine | 100.65 |
| 4-(3,4-dichlorophenyl)-6-(4-methyl-1H-imidazol-2-yl)pyrimidine | 92.3 |
| 4-(3,4-dichlorophenyl)-6-(5-methyl-1,2,4-oxadiazol-3-yl)pyrimidine | 51.01 |
| 4-(3,4-dichlorophenyl)-6-(5-methyl-4H-1,2,4-triazol-3-yl)pyrimidine | 79.99 |
| 4-(3,4-dichlorophenyl)-6-[3-(trifluoromethyl)pyrazol-1-yl]pyrimidine | 56.68 |
| 4-(3,4-dichlorophenyl)-6-[4-(trifluoromethyl)imidazol-1-yl]pyrimidine | 64.41 |
| 4-(3,4-dichlorophenyl)-6-[5-(trifluoromethyl)-1,2,4-oxadiazol-3-yl]pyrimidine | 87.01 |
| 4-(3,4-Dichloro-phenyl)-6-oxazol-2-yl-pyrimidine | 93 |
| 4-(3,4-Dichloro-phenyl)-6-thiazol-2-yl-pyrimidine | 48 |
| 4-(3,4-difluorophenyl)-6-(1H-tetrazol-5-yl)pyrimidine | 101.01 |
| 4-(3-chloro-4-fluorophenyl)-6-(1H-tetrazol-5-yl)pyrimidine | 102.51 |
| 4-(3-Chloro-4-isopropoxyphenyl)-6-(1H-tetrazol-5-yl)-pyrimidine | 100 |
| 4-(3-Chloro-4-trifluoromethoxy-phenyl)-6-(1H-tetrazol-5-yl)-pyrimidine | 100 |
| 4-(3-chlorophenyl)-6-(1H-tetrazol-5-yl)pyrimidine | 102.87 |
| 4-(3-chlorophenyl)-6-(1-methyltetrazol-5-yl)pyrimidine | 65.57 |
| 4-(3-chlorophenyl)-6-(2-methyltetrazol-5-yl)pyrimidine | 91.16 |
| 4-(3-chlorophenyl)-6-(3-methyl-1,2,4-oxadiazol-5-yl)pyrimidine | 90.97 |
| 4-(3-chlorophenyl)-6-(4H-1,2,4-triazol-3-yl)pyrimidine | 102.37 |
| 4-(3-chlorophenyl)-6-(4-methyl-1,3-oxazol-2-yl)pyrimidine | 100.91 |
| 4-(3-Fluoro-4-methyl-phenyl)-6-(1H-tetrazol-5-yl)-pyrimidine | 100 |
| 4-[6-(3,4-dichlorophenyl)pyrimidin-4-yl]-1,3-dihydroimidazol-2-one | 105.15 |
| 4-[6-(3,4-dichlorophenyl)pyrimidin-4-yl]-2-methyl-1H-pyrazol-3-one | 73.63 |
| 5-[6-(3,4-dichlorophenyl)pyrimidin-4-yl]-2,4-dihydro-1,2,4-triazol-3-one | 58.11 |
| 6-(3,4-dichlorophenyl)pyrimidine-4-carbonitrile | 68.36 |
| 6-[6-(3,4-dichlorophenyl)pyrimidin-4-yl]-N-methylpyridine-3-carboxamide | 39.11 |
| 6-chloro-2-[6-(3-chlorophenyl)pyrimidin-4-yl]-1H-benzimidazole | 39.06 |
| 4-(6-(3-chloro-4-isopropoxyphenyl)pyrimidin-4-yl)pyrrolidine-2-carboxylic acid | 71 |
| 4-(3,4-dichlorophenyl)-6-(4-(trifluoromethyl)-1H-imidazol-2-yl)pyrimidine | 0 |
| 4-(6-(3,4-dichlorophenyl)pyrimidin-4-yl)piperazine-2-carboxylic acid | 0 |
| (R)-1-(6-(3,4-dichlorophenyl)pyrimidin-4-yl)pyrrolidine-2-carboxylic acid | 7 |
| (S)-1-(6-(3,4-dichlorophenyl)pyrimidin-4-yl)pyrrolidine-2-carboxylic acid | 11 |
| 1-(6-(3,4-dichlorophenyl)pyrimidin-4-yl)pyrrolidine-3-carboxylic acid | 14 |
| 2-(6-(3-chloro-4-cyclopropoxyphenyl)pyrimidin-4-yl)oxazole | 71 |
| 1-(6-(3,4-dichlorophenyl)pyrimidin-4-yl)piperazine-2-carboxylic acid | 30 |
| 5-(6-(3-chloro-4-cyclopropoxyphenyl)pyrimidin-4-yl)pyrrolidine-2-carboxylic acid | 84 |
| 4-(3-chloro-4-cyclopropoxyphenyl)-6-(1H-1,2,3,4-tetrazol-5-yl)pyrimidine | 100 |
| 3-[6-(3-chloro-4-cyclopropoxyphenyl)pyrimidin-4-yl]-4,5-dihydro-1,2,4-oxadiazol-5-one | 93 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. At least one chemical entity chosen from compounds of Formula I

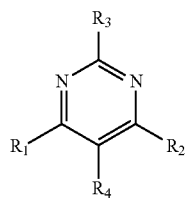

Formula I and pharmaceutically acceptable salts thereof wherein:

$R_1$ is chosen from optionally substituted aryl and optionally substituted heteroaryl;

$R_2$ is tetrazolyl;

$R_3$ is chosen from hydrogen and optionally substituted lower alkyl and $R_4$ is chosen from hydrogen, halo, optionally substituted lower alkyl, hydroxyl, optionally substituted lower alkoxy, and optionally substituted amino, or $R_1$ and $R_4$, taken together with intervening atoms form a bicyclic ring of the formula

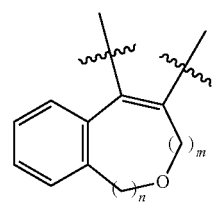

which is optionally substituted where m is 0 or 1 and n is 0 or 1, provided that at least one of m and n is 1, provided that
1) when $R_3$ and $R_4$ are hydrogen, then $R_1$ is not 5-chloropyridin-3-yl, 3,5-dichlorophenyl, or

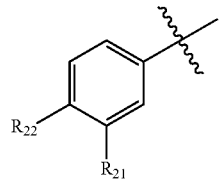

where $R_{21}$ is halo and $R_{22}$ is hydrogen, halo, trifluoromethoxy, methyl, or isopropoxy.

2. At least one chemical entity of claim 1 wherein $R_1$ is phenyl optionally substituted with one, two, or three groups chosen from heteroaryl, heterocycloalkyl, cycloalkyl, optionally substituted cycloalkoxy, optionally substituted amino, halo, optionally substituted lower alkyl, optionally substituted lower alkoxy, and hydroxy.

3. At least one chemical entity of claim 2 wherein $R_1$ is phenyl optionally substituted with one, two, or three groups chosen from heteroaryl, heterocycloalkyl, cycloalkyl, cycloalkoxy optionally substituted with lower alkyl, lower alkoxy, or lower alkyl substituted with halo, optionally substituted amino, halo, lower alkyl optionally substituted with amino, alkylamino, dialkylamino, or heterocycloalkyl, trifluoromethyl, trifluoromethoxy, lower alkoxy, and hydroxy.

4. At least one chemical entity of claim 3 wherein $R_1$ is phenyl optionally substituted with one, two, or three groups chosen from furan-2-yl, 1H-pyrrol-2-yl, 1H-imidazol-2-yl, pyrrolidin-3-yl, pyrrolidin-1-yl, oxetan-3-yl optionally substituted with lower alkyl, halo, lower alkyl, cyclopropyl optionally substituted with lower alkyl, lower alkoxy, or lower alkyl substituted with halo, optionally substituted amino, lower alkyl optionally substituted with amino, alkylamino, dialkylamino, or heterocycloalkyl, trifluoromethoxy, cyclopropoxy optionally substituted with lower alkoxy, lower alkoxy, or lower alkyl substituted with halo, and trifluoromethyl.

5. At least one chemical entity of claim 4 wherein $R_1$ is chosen from 3-chloro-4-cyclopropoxyphenyl, 4-tert-butyl-3-chlorophenyl, 3-chloro-4-(furan-2-yl)phenyl, 3-chloro-4-(1H-pyrrol-2-yl)phenyl, 3-chloro-4-(1H-imidazol-2-yl)phenyl, 3-chloro-4-(pyrrolidin-3-yl)phenyl, 3-chloro-4-(pyrrolidin-1-yl)phenyl, 3-chloro-4-(3-methyloxetan-3-yl)phenyl, 3-chloro-4-[1-(trifluoromethyl)cyclopropyl]phenyl, 3-chloro-4-cyclopropylphenyl, 3-chloro-4-(1-methylcyclopropyl)phenyl, 3-chloro-4-(1-methoxycyclopropyl)phenyl, 3-chloro-4-[cyclopropyl(methyl)amino]phenyl, 3-chloro-4-(cyclopropylamino)phenyl, 3-chloro-4-[(dimethylamino)methyl]phenyl, 4-(aziridin-1-ylmethyl)-3-chlorophenyl, 3-chloro-4-trifluoromethoxyphenyl, 3-chloro-4-methylphenyl, 3-fluoro-4-methylphenyl, 3-chloro-4-fluorophenyl, 3-chloro-4-isopropoxyphenyl, 3,4-difluorophenyl, 2-trifluoromethylphenyl, 3,4-dichlorophenyl, 3-chlorophenyl, 4-chlorophenyl, and 3,5-dichlorophenyl.

6. At least one chemical entity of claim 1 wherein $R_2$ is chosen from 1H-tetrazol-5-yl, 2H-tetrazol-5-yl, and tetrazol-1-yl.

7. At least one chemical entity of claim 1 wherein $R_4$ is chosen from hydrogen, methyl, fluoro, methoxy, methoxymethyl, hydroxyl, and amino.

8. At least one chemical entity of claim 7 wherein $R_4$ is hydrogen.

9. At least one chemical entity of claim 1 wherein $R_3$ is hydrogen.

10. At least one chemical entity chosen from
4-(6-(3-chloro-4-isopropoxyphenyl)pyrimidin-4-yl)pyrrolidine-2-carboxylic acid,
4-(3,4-dichlorophenyl)-6-(4-(trifluoromethyl)-1H-imidazol-2-yl)pyrimidine,
4-(6-(3,4-dichlorophenyl)pyrimidin-4-yl)piperazine-2-carboxylic acid,
(R)-1-(6-(3,4-dichlorophenyl)pyrimidin-4-yl)pyrrolidine-2-carboxylic acid,
(S)-1-(6-(3,4-dichlorophenyl)pyrimidin-4-yl)pyrrolidine-2-carboxylic acid,
1-(6-(3,4-dichlorophenyl)pyrimidin-4-yl)pyrrolidine-3-carboxylic acid,
2-(6-(3-chloro-4-cyclopropoxyphenyl)pyrimidin-4-yl)oxazole,
1-(6-(3,4-dichlorophenyl)pyrimidin-4-yl)piperazine-2-carboxylic acid,
5-(6-(3-chloro-4-cyclopropoxyphenyl)pyrimidin-4-yl)pyrrolidine-2-carboxylic acid,
4-(3-chloro-4-cyclopropoxyphenyl)-6-(1H-1,2,3,4-tetrazol-5-yl)pyrimidine,
3-[6-(3-chloro-4-cyclopropoxyphenyl)pyrimidin-4-yl]-4,5-dihydro-1,2,4-oxadiazol-5-one,
4-[3-chloro-4-(oxetan-3-yloxy)phenyl]-6-(2H-1,2,3,4-tetrazol-5-yl)pyrimidine,
3-{6-[3-chloro-4-(oxetan-3-yloxy)phenyl]pyrimidin-4-yl}-4,5-dihydro-1,2,4-oxadiazol-5-one,
4-[3-chloro-4-(cyclopropylmethoxy)phenyl]-6-(2H-1,2,3,4-tetrazol-5-yl)pyrimidine,
3-{6-[3-chloro-4-(cyclopropylmethoxy)phenyl]pyrimidin-4-yl}-4,5-dihydro-1,2,4-oxadiazol-5-one,
4-[3-chloro-4-(cyclopropoxymethyl)phenyl]-6-(2H-1,2,3,4-tetrazol-5-yl)pyrimidine,
3-{6-[3-chloro-4-(cyclopropoxymethyl)phenyl]pyrimidin-4-yl}-4,5-dihydro-1,2,4-oxadiazol-5-one,
4-[3-chloro-4-(cyclopropylmethyl)phenyl]-6-(2H-1,2,3,4-tetrazol-5-yl)pyrimidine,
3-{6-[3-chloro-4-(cyclopropylmethyl)phenyl]pyrimidin-4-yl}-4,5-dihydro-1,2,4-oxadiazol-5-one,
4-[3-chloro-4-(cyclopropylsulfanyl)phenyl]-6-(2H-1,2,3,4-tetrazol-5-yl)pyrimidine,
3-{6-[3-chloro-4-(cyclopropylsulfanyl)phenyl]pyrimidin-4-yl}-4,5-dihydro-1,2,4-oxadiazol-5-one,
4-[3-chloro-4-(cyclopropanesulfinyl)phenyl]-6-(2H-1,2,3,4-tetrazol-5-yl)pyrimidine,
3-{6-[3-chloro-4-(cyclopropanesulfinyl)phenyl]pyrimidin-4-yl}-4,5-dihydro-1,2,4-oxadiazol-5-one,
4-[3-chloro-4-(cyclopropanesulfonyl)phenyl]-6-(2H-1,2,3,4-tetrazol-5-yl)pyrimidine,
3-{6-[3-chloro-4-(cyclopropanesulfonyl)phenyl]pyrimidin-4-yl}-4,5-dihydro-1,2,4-oxadiazol-5-one,
{2-chloro-4-[6-(2H-1,2,3,4-tetrazol-5-yl)pyrimidin-4-yl]phenyl}(cyclopropyl)methanol,
3-{6-[3-chloro-4-(1-cyclopropoxyethyl)phenyl]pyrimidin-4-yl}-4,5-dihydro-1,2,4-oxadiazol-5-one,
4-(3-chloro-4-cyclopropanecarbonylphenyl)-6-(2H-1,2,3,4-tetrazol-5-yl)pyrimidine,
3-[6-(3-chloro-4-cyclopropanecarbonylphenyl)pyrimidin-4-yl]-4,5-dihydro-1,2,4-oxadiazol-5-one,
4-(3-chloro-4-cyclopropylphenyl)-6-(2H-1,2,3,4-tetrazol-5-yl)pyrimidine,
3-[6-(3-chloro-4-cyclopropylphenyl)pyrimidin-4-yl]-4,5-dihydro-1,2,4-oxadiazol-5-one,
4-[4-(aziridin-1-ylmethyl)-3-chlorophenyl]-6-(2H-1,2,3,4-tetrazol-5-yl)pyrimidine, 3-{6-[4-(aziridin-1-ylmethyl)-3-chlorophenyl]pyrimidin-4-yl}-4,5-dihydro-1,2,4-oxadiazol-5-one,
({2-chloro-4-[6-(2H-1,2,3,4-tetrazol-5-yl)pyrimidin-4-yl]phenyl}methyl)dimethylamine,
3-(6-{3-chloro-4-[(dimethylamino)methyl]phenyl}pyrimidin-4-yl)-4,5-dihydro-1,2,4-oxadiazol-5-one,
4-(7-chloro-1-benzofuran-5-yl)-6-(2H-1,2,3,4-tetrazol-5-yl)pyrimidine,
3-[6-(7-chloro-1-benzofuran-5-yl)pyrimidin-4-yl]-4,5-dihydro-1,2,4-oxadiazol-5-one,
7-chloro-5-[6-(2H-1,2,3,4-tetrazol-5-yl)pyrimidin-4-yl]-1,3-benzoxazole,
3-[6-(7-chloro-1,3-benzoxazol-5-yl)pyrimidin-4-yl]-4,5-dihydro-1,2,4-oxadiazol-5-one,
7-chloro-5-[6-(2H-1,2,3,4-tetrazol-5-yl)pyrimidin-4-yl]-1,3-benzothiazole
3-[6-(7-chloro-1,3-benzothiazol-5-yl)pyrimidin-4-yl]-4,5-dihydro-1,2,4-oxadiazol-5-one
7-chloro-5-[6-(2H-1,2,3,4-tetrazol-5-yl)pyrimidin-4-yl]-1H-1,3-benzodiazole,
3-[6-(7-chloro-1H-1,3-benzodiazol-5-yl)pyrimidin-4-yl]-4,5-dihydro-1,2,4-oxadiazol-5-one,
2-chloro-N-cyclopropyl-4-[6-(2H-1,2,3,4-tetrazol-5-yl)pyrimidin-4-yl]aniline,
3-{6-[3-chloro-4-(cyclopropylamino)phenyl]pyrimidin-4-yl}-4,5-dihydro-1,2,4-oxadiazol-5-one,
2-chloro-N-cyclopropyl-N-methyl-4-[6-(2H-1,2,3,4-tetrazol-5-yl)pyrimidin-4-yl]aniline,
3-(6-{3-chloro-4-[cyclopropyl(methyl)amino]phenyl}pyrimidin-4-yl)-4,5-dihydro-1,2,4-oxadiazol-5-one,
4-[3-chloro-4-(1-methoxycyclopropyl)phenyl]-6-(2H-1,2,3,4-tetrazol-5-yl)pyrimidine,
3-{6-[3-chloro-4-(1-methoxycyclopropyl)phenyl]pyrimidin-4-yl}-4,5-dihydro-1,2,4-oxadiazol-5-one,
4-(2,3-dihydro-1,4-benzodioxin-6-yl)-6-(2H-1,2,3,4-tetrazol-5-yl)pyrimidine,
3-[6-(2,3-dihydro-1,4-benzodioxin-6-yl)pyrimidin-4-yl]-4,5-dihydro-1,2,4-oxadiazol-5-one,
7-chloro-2-methyl-5-[6-(2H-1,2,3,4-tetrazol-5-yl)pyrimidin-4-yl]-1,3-benzoxazole,
3-[6-(7-chloro-2-methyl-1,3-benzoxazol-5-yl)pyrimidin-4-yl]-4,5-dihydro-1,2,4-oxadiazol-5-one,
7-chloro-5-[6-(2H-1,2,3,4-tetrazol-5-yl)pyrimidin-4-yl]-2,3-dihydro-1,3-benzoxazol-2-one,
7-chloro-5-[6-(5-oxo-4,5-dihydro-1,2,4-oxadiazol-3-yl)pyrimidin-4-yl]-2,3-dihydro-1,3-benzoxazol-2-one,
7-chloro-3-methyl-5-[6-(2H-1,2,3,4-tetrazol-5-yl)pyrimidin-4-yl]-2,3-dihydro-1,3-benzoxazol-2-one,
7-chloro-3-methyl-5-[6-(5-oxo-4,5-dihydro-1,2,4-oxadiazol-3-yl)pyrimidin-4-yl]-2,3-dihydro-1,3-benzoxazol-2-one,
7-chloro-2-cyclopropyl-5-[6-(2H-1,2,3,4-tetrazol-5-yl)pyrimidin-4-yl]-1,3-benzoxazole,
3-[6-(7-chloro-2-cyclopropyl-1,3-benzoxazol-5-yl)pyrimidin-4-yl]-4,5-dihydro-1,2,4-oxadiazol-5-one,
4-{8-chloroimidazo[1,2-a]pyridin-6-yl}-6-(2H-1,2,3,4-tetrazol-5-yl)pyrimidine,
3-(6-{8-chloroimidazo[1,2-a]pyridin-6-yl}pyrimidin-4-yl)-4,5-dihydro-1,2,4-oxadiazol-5-one,
4-chloro-6-[6-(2H-1,2,3,4-tetrazol-5-yl)pyrimidin-4-yl]-1,3-benzoxazole,
3-[6-(4-chloro-1,3-benzoxazol-6-yl)pyrimidin-4-yl]-4,5-dihydro-1,2,4-oxadiazol-5-one,
6-[6-(2H-1,2,3,4-tetrazol-5-yl)pyrimidin-4-yl]quinoline,
3-[6-(quinolin-6-yl)pyrimidin-4-yl]-4,5-dihydro-1,2,4-oxadiazol-5-one,
4-{pyrazolo[1,5-a]pyridin-5-yl}-6-(2H-1,2,3,4-tetrazol-5-yl)pyrimidine,
3-(6-{pyrazolo[1,5-a]pyridin-5-yl}pyrimidin-4-yl)-4,5-dihydro-1,2,4-oxadiazol-5-one,
1-cyclopropyl-5-[6-(2H-1,2,3,4-tetrazol-5-yl)pyrimidin-4-yl]-1H-indole,
3-[6-(1-cyclopropyl-1H-indol-5-yl)pyrimidin-4-yl]-4,5-dihydro-1,2,4-oxadiazol-5-one,
1-cyclopropyl-5-[6-(2H-1,2,3,4-tetrazol-5-yl)pyrimidin-4-yl]-1H-indazole,
3-[6-(1-cyclopropyl-1H-indazol-5-yl)pyrimidin-4-yl]-4,5-dihydro-1,2,4-oxadiazol-5-one,
5-chloro-7-[6-(2H-1,2,3,4-tetrazol-5-yl)pyrimidin-4-yl]quinoxaline,
3-[6-(8-chloroquinoxalin-6-yl)pyrimidin-4-yl]-4,5-dihydro-1,2,4-oxadiazol-5-one,
4-(2H-1,3-benzodioxol-5-yl)-6-(2H-1,2,3,4-tetrazol-5-yl)pyrimidine,
3-[6-(2H-1,3-benzodioxol-5-yl)pyrimidin-4-yl]-4,5-dihydro-1,2,4-oxadiazol-5-one,
4-(2,2-difluoro-2H-1,3-benzodioxol-5-yl)-6-(2H-1,2,3,4-tetrazol-5-yl)pyrimidine,
3-[6-(2,2-difluoro-2H-1,3-benzodioxol-5-yl)pyrimidin-4-yl]-4,5-dihydro-1,2,4-oxadiazol-5-one,
4-chloro-6-[6-(2H-1,2,3,4-tetrazol-5-yl)pyrimidin-4-yl]-2,1,3-benzoxadiazole,
3-[6-(7-chloro-2,1,3-benzoxadiazol-5-yl)pyrimidin-4-yl]-4,5-dihydro-1,2,4-oxadiazol-5-one,
4-(7-chloro-2,3,3a,7a-tetrahydro-1-benzofuran-5-yl)-6-(2H-1,2,3,4-tetrazol-5-yl)pyrimidine,
3-[6-(7-chloro-2,3,3a,7a-tetrahydro-1-benzofuran-5-yl)pyrimidin-4-yl]-4,5-dihydro-1,2,4-oxadiazol-5-one,
7-chloro-5-[6-(2H-1,2,3,4-tetrazol-5-yl)pyrimidin-4-yl]-1H-indole,
3-[6-(7-chloro-1H-indol-5-yl)pyrimidin-4-yl]-4,5-dihydro-1,2,4-oxadiazol-5-one,
7-chloro-1-methyl-5-[6-(2H-1,2,3,4-tetrazol-5-yl)pyrimidin-4-yl]-1H-indazole,
3-[6-(7-chloro-1-methyl-1H-indazol-5-yl)pyrimidin-4-yl]-4,5-dihydro-1,2,4-oxadiazol-5-one,
8-chloro-6-[6-(2H-1,2,3,4-tetrazol-5-yl)pyrimidin-4-yl]quinoline,
3-[6-(8-chloroquinolin-6-yl)pyrimidin-4-yl]-4,5-dihydro-1,2,4-oxadiazol-5-one,
8-chloro-6-[6-(2H-1,2,3,4-tetrazol-5-yl)pyrimidin-4-yl]quinazoline,
3-[6-(8-chloroquinazolin-6-yl)pyrimidin-4-yl]-4,5-dihydro-1,2,4-oxadiazol-5-one,
5-chloro-7-[6-(2H-1,2,3,4-tetrazol-5-yl)pyrimidin-4-yl]quinazoline,
3-[6-(5-chloroquinazolin-7-yl)pyrimidin-4-yl]-4,5-dihydro-1,2,4-oxadiazol-5-one,
5-chloro-7-[6-(2H-1,2,3,4-tetrazol-5-yl)pyrimidin-4-yl]quinoxaline,
3-[6-(8-chloroquinoxalin-6-yl)pyrimidin-4-yl]-4,5-dihydro-1,2,4-oxadiazol-5-one,
7-chloro-5-[6-(2H-1,2,3,4-tetrazol-5-yl)pyrimidin-4-yl]-1H-1,3-benzodiazole,
3-[6-(7-chloro-1H-1,3-benzodiazol-5-yl)pyrimidin-4-yl]-4,5-dihydro-1,2,4-oxadiazol-5-one,
4-[3-chloro-4-(1-methylcyclopropyl)phenyl]-6-(2H-1,2,3,4-tetrazol-5-yl)pyrimidine,
3-{6-[3-chloro-4-(1-methylcyclopropyl)phenyl]pyrimidin-4-yl}-4,5-dihydro-1,2,4-oxadiazol-5-one, 4-{3-chloro-4-[1-(trifluoromethyl)cyclopropyl]phenyl}-6-(2H-1,2,3,4-tetrazol-5-yl)pyrimidine,
3-(6-{3-chloro-4-[1-(trifluoromethyl)cyclopropyl]phenyl}pyrimidin-4-yl)-4,5-dihydro-1,2,4-oxadiazol-5-one,
4-[3-chloro-4-(3-methyloxetan-3-yl)phenyl]-6-(2H-1,2,3,4-tetrazol-5-yl)pyrimidine,
3-{6-[3-chloro-4-(3-methyloxetan-3-yl)phenyl]pyrimidin-4-yl}-4,5-dihydro-1,2,4-oxadiazol-5-one,
4-[3-chloro-4-(pyrrolidin-1-yl)phenyl]-6-(2H-1,2,3,4-tetrazol-5-yl)pyrimidine,
3-{6-[3-chloro-4-(pyrrolidin-1-yl)phenyl]pyrimidin-4-yl}-4,5-dihydro-1,2,4-oxadiazol-5-one,
4-[3-chloro-4-(pyrrolidin-3-yl)phenyl]-6-(2H-1,2,3,4-tetrazol-5-yl)pyrimidine,
3-{6-[3-chloro-4-(pyrrolidin-3-yl)phenyl]pyrimidin-4-yl}-4,5-dihydro-1,2,4-oxadiazol-5-one,
4-[3-chloro-4-(1H-imidazol-2-yl)phenyl]-6-(2H-1,2,3,4-tetrazol-5-yl)pyrimidine,
3-{6-[3-chloro-4-(1H-imidazol-2-yl)phenyl]pyrimidin-4-yl}-4,5-dihydro-1,2,4-oxadiazol-5-one,
4-[3-chloro-4-(1H-pyrrol-2-yl)phenyl]-6-(2H-1,2,3,4-tetrazol-5-yl)pyrimidine,
3-{6-[3-chloro-4-(1H-pyrrol-2-yl)phenyl]pyrimidin-4-yl}-4,5-dihydro-1,2,4-oxadiazol-5-one,
4-[3-chloro-4-(furan-2-yl)phenyl]-6-(2H-1,2,3,4-tetrazol-5-yl)pyrimidine,
3-{6-[3-chloro-4-(furan-2-yl)phenyl]pyrimidin-4-yl}-4,5-dihydro-1,2,4-oxadiazol-5-one,
4-(4-tert-butyl-3-chlorophenyl)-6-(2H-1,2,3,4-tetrazol-5-yl)pyrimidine,
3-[6-(4-tert-butyl-3-chlorophenyl)pyrimidin-4-yl]-4,5-dihydro-1,2,4-oxadiazol-5-one,
4-(3-chloro-4-cyclopropoxyphenyl)-5-methyl-6-(2H-1,2,3,4-tetrazol-5-yl)pyrimidine,
3-[6-(3-chloro-4-cyclopropoxyphenyl)-5-methylpyrimidin-4-yl]-4,5-dihydro-1,2,4-oxadiazol-5-one,
4-(3-chloro-4-cyclopropoxyphenyl)-5-fluoro-6-(2H-1,2,3,4-tetrazol-5-yl)pyrimidine,
3-[6-(3-chloro-4-cyclopropoxyphenyl)-5-fluoropyrimidin-4-yl]-4,5-dihydro-1,2,4-oxadiazol-5-one,
4-(3-chloro-4-cyclopropoxyphenyl)-5-methoxy-6-(2H-1,2,3,4-tetrazol-5-yl)pyrimidine,
3-[6-(3-chloro-4-cyclopropoxyphenyl)-5-methoxypyrimidin-4-yl]-4,5-dihydro-1,2,4-oxadiazol-5-one,
5-{7-chloro-8-cyclopropoxy-6H-isochromeno[4,3-d]pyrimidin-4-yl}-2H-1,2,3,4-tetrazole,
3-{7-chloro-8-cyclopropoxy-6H-isochromeno[4,3-d]pyrimidin-4-yl}-4,5-dihydro-1,2,4-oxadiazol-5-one,
4-(3-chloro-4-cyclopropoxyphenyl)-6-(2H-1,2,3,4-tetrazol-5-yl)pyrimidin-5-amine,
3-[5-amino-6-(3-chloro-4-cyclopropoxyphenyl)pyrimidin-4-yl]-4,5-dihydro-1,2,4-oxadiazol-5-one,
4-(3-chloro-4-cyclopropoxyphenyl)-5-(methoxymethyl)-6-(2H-1,2,3,4-tetrazol-5-yl)pyrimidine,
3-[6-(3-chloro-4-cyclopropoxyphenyl)-5-(methoxymethyl)pyrimidin-4-yl]-4,5-dihydro-1,2,4-oxadiazol-5-one,
4-(3,4-dichlorophenyl)-5-methyl-6-(2H-1,2,3,4-tetrazol-5-yl)pyrimidine,
3-[6-(3,4-dichlorophenyl)-5-methylpyrimidin-4-yl]-4,5-dihydro-1,2,4-oxadiazol-5-one,
4-(3,4-dichlorophenyl)-5-fluoro-6-(2H-1,2,3,4-tetrazol-5-yl)pyrimidine,
3-[6-(3,4-dichlorophenyl)-5-fluoropyrimidin-4-yl]-4,5-dihydro-1,2,4-oxadiazol-5-one,
4-(3,4-dichlorophenyl)-5-methoxy-6-(2H-1,2,3,4-tetrazol-5-yl)pyrimidine,
3-[6-(3,4-dichlorophenyl)-5-methoxypyrimidin-4-yl]-4,5-dihydro-1,2,4-oxadiazol-5-one,
5-{7,8-dichloro-6H-isochromeno[4,3-d]pyrimidin-4-yl}-2H-1,2,3,4-tetrazole,
3-{7,8-dichloro-6H-isochromeno[4,3-d]pyrimidin-4-yl}-4,5-dihydro-1,2,4-oxadiazol-5-one,
4-(3,4-dichlorophenyl)-6-(2H-1,2,3,4-tetrazol-5-yl)pyrimidin-5-amine,
3-[5-amino-6-(3,4-dichlorophenyl)pyrimidin-4-yl]-4,5-dihydro-1,2,4-oxadiazol-5-one,
4-(3,4-dichlorophenyl)-5-(methoxymethyl)-6-(2H-1,2,3,4-tetrazol-5-yl)pyrimidine,
3-[6-(3,4-dichlorophenyl)-5-(methoxymethyl)pyrimidin-4-yl]-4,5-dihydro-1,2,4-oxadiazol-5-one,
4-(3-chloro-4-cyclopropoxyphenyl)-6-(2H-1,2,3,4-tetrazol-5-yl)pyrimidin-5-ol,
3-[6-(3-chloro-4-cyclopropoxyphenyl)-5-hydroxypyrimidin-4-yl]-4,5-dihydro-1,2,4-oxadiazol-5-one,
4-(3,4-dichlorophenyl)-6-(2H-1,2,3,4-tetrazol-5-yl)pyrimidin-5-ol, and
3-[6-(3,4-dichlorophenyl)-5-hydroxypyrimidin-4-yl]-4,5-dihydro-1,2,4-oxadiazol-5-one,
and pharmaceutically acceptable salts thereof.

* * * * *